(12) United States Patent
Huang

(10) Patent No.: US 10,954,277 B2
(45) Date of Patent: Mar. 23, 2021

(54) MATERIALS AND METHODS FOR TREATING CANCER

(71) Applicant: Mayo Foundation for Medical Education and Research, Rochester, MN (US)

(72) Inventor: Haojie Huang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 15 days.

(21) Appl. No.: 16/301,333

(22) PCT Filed: Mar. 8, 2017

(86) PCT No.: PCT/US2017/021352
§ 371 (c)(1),
(2) Date: Nov. 13, 2018

(87) PCT Pub. No.: WO2017/196442
PCT Pub. Date: Nov. 16, 2017

(65) Prior Publication Data
US 2019/0194276 A1    Jun. 27, 2019

Related U.S. Application Data

(60) Provisional application No. 62/335,785, filed on May 13, 2016.

(51) Int. Cl.
*C07K 14/47* (2006.01)
*A61P 35/00* (2006.01)
*A61K 38/00* (2006.01)

(52) U.S. Cl.
CPC .......... *C07K 14/4702* (2013.01); *A61P 35/00* (2018.01); *A61K 38/00* (2013.01)

(58) Field of Classification Search
None
See application file for complete search history.

(56) References Cited

U.S. PATENT DOCUMENTS

| 8,628,931 B2 | 1/2014 | Liotta et al. |
| 2006/0069049 A1 | 3/2006 | Goldberg et al. |
| 2010/0292316 A1 | 11/2010 | Sanders et al. |
| 2013/0058964 A1 | 3/2013 | Unutmaz et al. |
| 2014/0212510 A1 | 7/2014 | Hickey et al. |

FOREIGN PATENT DOCUMENTS

CN    104610435    5/2015

OTHER PUBLICATIONS

Brent et al. "Structural Basis for DNA Recognition by FoxO1 and its Regulation by Post-Translational Modification," Structure. Sep. 10, 2008; 16(9): 1407-1416 (Year: 2008).*
Calnan et al. "The FoxO code," Oncogene (2008) 27, 2276-2288 (Year: 2008).*
English translation of CN 104,610,435 (Year: 2015).*
Liu et al. "Cyclin-Dependent Kinase 4 Phosphorylates and Positively Regulates PAX3-FOXO1 in Human Alveolar Rhabdomyosarcoma Cells," PLoS One 2013, 8(2): e58193, p. 1-11 (Year: 2013).*
Zhou et al. "The Roles of Cdk5-Mediated Subcellular Localization of FOXO1 in Neuronal Death," The Journal of Neuroscience, 2015, 35(6):2624-2635 (Year: 215).*
Tunnemann et al. "Live-cell analysis of cell penetration ability and toxicity of oligo-arginines," J. Pept. Sci. 2008; 14: 469-476 (Year: 2008).*
Aoki et al., "Proteasomal degradation of the FoxO1 transcriptional regulator in cells transformed by the P3k and Akt oncoproteins," Proc. Natl. Acad. Sci. USA., 101(37):13613-7, Sep. 2004.
Biggs et al., "Protein kinase B/Akt-mediated phosphorylation promotes nuclear exclusion of the winged helix transcription factor FKHR1," Proc. Natl. Acad. Sci. USA., 96(13):7421-7426, Jun. 1999.
Brunet et al., "14-3-3 transits to the nucleus and participates in dynamic nucleocytoplasmic transport," J. Cell Biol., 156(5):817-828, Mar. 2002.
Brunet et al., "Akt promotes cell survival by phosphorylating and inhibiting a Forkhead transcription factor," Cell, 96(6):857-68, Mar. 1999.
Chandarlapaty et al., "AKT inhibition relieves feedback suppression of receptor tyrosine kinase expression and activity," Cancer Cell, 19(1):58-71, Jan. 2011.
Chen et al., "Cyclin-dependent kinases regulate epigenetic gene silencing through phosphorylation of EZH2," Nat. Cell Biol., 12(11):1108-1114, Nov. 2010.
Chen et al., "IQGAP1 is overexpressed in hepatocellular carcinoma and promotes cell proliferation by Akt activation," Exp. Mol. Med., 42(7):477-483, Jul. 2010.
Dong et al., "FOXO1A is a candidate for the 13q14 tumor suppressor gene inhibiting androgen receptor signaling in prostate cancer," Cancer Res., 66(14):6998-7006, Jul. 2006.
Eng et al., "An approach to correlate tandem mass spectral data of peptides with amino acid sequences in a protein database," J. Am. Soc. Mass Spectrom, 5(11):976-989, Nov. 1994.

(Continued)

Primary Examiner — Christina Bradley
(74) Attorney, Agent, or Firm — Fish & Richardson P.C.

(57) ABSTRACT

This document provides methods and materials for treating cancer (e.g., chemotherapeutic resistant cancer). For example, compositions containing a phosphorylation-mimicking peptide (e.g., a phosphorylation-mimicking FOXO1-derived peptide) to treat a mammal having cancer (e.g., to reduce the number of cancer cells in a mammal) and methods of using such compositions are provided. This document also provides methods of treating a mammal having cancer (e.g., to reduce the number of cancer cells in a mammal) by administering a phosphorylation-mimicking FOXO1-derived peptide to the mammal.

7 Claims, 42 Drawing Sheets

Specification includes a Sequence Listing.

(56) References Cited

OTHER PUBLICATIONS

Extended European Search Report in Application No. 17796518.3 dated Jan. 21, 2019, 7 pages.
Gan et al., "Cyclin D1 promotes anchorage-independent cell survival by inhibiting FOXO-mediated anoikis," Cell Death Differ., 16(10):1408-1417, Oct. 2009.
Gan et al., "Inhibition of the androgen receptor as a novel mechanism of taxol chemotherapy in prostate cancer," Cancer Res., 69(21):8386-8394, Nov. 2009.
Genbank Accession No. AAH21981.1, "Forkhead box O1 [*Homo sapiens*]," Sep. 11, 2007, 2 pages.
Genbank Accession No. AAH67223.1, "Lactate dehydrogenase A [*Homo sapiens*]," Jul. 15, 2006, 2 pages.
Genbank Accession No. AAH70065.3, "Forkhead box O1 [*Homo sapiens*]," Jun. 26, 2007, 2 pages.
Genbank Accession No. AIC54695.1, "LDHA, partial [synthetic construct]," Mar. 19, 2015, 2 pages.
Genbank Accession No. BCO21981.2, "*Homo sapiens* forkhead box O1, mRNA (cDNA clone MGC:1750 Image:2959021), complete cds," Sep. 11, 2007, 2 pages.
Genbank Accession No. BC070065.1, "*Homo sapiens* forkhead box O1, mRNA (cDNA clone MGC:87303 Image:30345006), complete cds," Jun. 26, 2007, 2 pages.
Genbank Accession No. CAG33056.1, "LDHA [*Homo sapiens*]," Oct. 16, 2008, 2 pages.
Genbank Accession No. NM_002015.3, "*Homo sapiens* forkhead box O1 (FOXO1), mRNA," Nov. 1, 2017, 7 pages.
Genbank Accession No. NP_001128711.1, "L-lactate dehydrogenase A chain isoform 2 [*Homo sapiens*]," Oct. 2, 2017, 3 pages.
Genbank Accession No. NP_001158886.1, "L-lactate dehydrogenase A chain isoform 3 [*Homo sapiens*]," Oct. 2, 2017, 3 pages.
Genbank Accession No. NP_001158887.1, "L-lactate dehydrogenase A chain isoform 4 [*Homo sapiens*]," Oct. 2, 2017, 4 pages.
Genbank Accession No. NP_001158888.1, "L-lactate dehydrogenase A chain isoform 5 [*Homo sapiens*]," Oct. 2, 2017, 4 pages.
Genbank Accession No. NP_002006.2, "forkhead box protein O1 [*Homo sapiens*]," Nov. 1, 2017, 5 pages.
Genbank Accession No. NP_002645.3, "pyruvate kinase PKM isoform a [*Homo sapiens*]," Nov. 20, 2017, 5 pages.
Genbank Accession No. NP_005557.1, "L-lactate dehydrogenase A chain isoform 1 [*Homo sapiens*]," Oct. 2, 2017, 4 pages.
Genbank Accession No. NP_006507.2, "solute carrier family 2, facilitated glucose transporter member 1 [Homo sapiens]," Nov. 13, 2017, 4 pages.
Gilley et al., "FOXO transcription factors directly activate bim gene expression and promote apoptosis in sympathetic neurons," J. Cell Biol., 162(4):613-22, Aug. 2003.
Goto et al., "The involvement of FOXO1 in cytotoxic stress and drug-resistance induced by paclitaxel in ovarian cancers," Br. J. Cancer, 98(6):1068-1075, Mar. 2008.
Haflidadottir et al., "Upregulation of miR-96 enhances cellular proliferation of prostate cancer cells through FOXO1," PLoS One, 8(8):e72400, Aug. 2013.
Huang et al, "CDK2-dependent phosphorylation of FOXO1 as an apoptotic response to DNA damage," Science, 314(5797):294-297, Oct. 2006.
Huang et al., "PTEN induces chemosensitivity in PTEN-mutated prostate cancer cells by suppression of Bcl-2 expression," J. Biol. Chem., 276(42):38830-38836, Oct. 2001.
Huang et al., "Skp2 inhibits FOXO1 in tumor suppression through ubiquitin-Mediated degradation," Proc. Natl. Acad. Sci. USA, 102:1649-54, Feb. 2005.
International Preliminary Report on Patentability in Application No. PCT/US2017/021352 dated Nov. 13, 2018, 8 pages.
International Search Report & Written Opinion in Application No. PCT/US2017/021352 dated Jul. 19, 2017, 16 pages.
Jameson et al., "IQGAP1 scaffold-kinase interaction blockade selectively targets RAS-MAP kinase-driven tumors," Nat. Med., 19(5):626-630, May 2013.

Kalaany and Sabatini, "Tumours with PI3K activation are resistant to dietary restriction," Nature, 458(7239):725-31, Apr. 2009.
Kanao et al., "Activation of FoxO by LRRK2 induces expression of proapoptotic proteins and alters survival of postmitotic dopaminergic neuron in *Drosophila*," Human molecular genetics, 19(19):3747-58, Jul. 2010.
Kinkade et al., "Targeting AKT/mTOR and ERK MAPK signaling inhibits hormone-refractory prostate cancer in a preclinical mouse model," J. Clin. Inv., 118(9):3051-64, Sep. 2008.
Kops et al., "Forkhead transcription factor FOXO3a protects quiescent cells from oxidative stress," Nature, 419(6904):316-21, Sep. 2002.
Lin et al., "FoxO transcription factors promote AKT Ser473 phosphorylation and renal tumor growth in response to pharmacologic inhibition of the PI3K-AKT pathway," Cancer Res., 74(6):1682-1693, Mar. 2014.
Liu et al., "A transcription-independent function of FOXO1 in inhibition of androgen-independent activation of the androgen receptor in prostate cancer cells," Cancer Res., 68(24):10290-10299, Dec. 2008.
Matsuzaki et al., "Insulin-induced phosphorylation of FKHR (Foxo1) targets to proteasomal degradation," Proc. Natl. Acad. Sci. USA, 100:11285-90, Sep. 2003.
Medema et al., "AFX-like Forkhead transcription factors mediate cell-cycle regulation by Ras and PKB through p27 kip1," Nature, 404(6779):782-7, Apr. 2000.
Mehnert et al., "Rationally designed treatment for solid tumors with MAPK pathway activation: a phase I study of paclitaxel and bortezomib using an adaptive dose-finding approach," Mol. Cancer Ther., 10(8):1509-19, Aug. 2011.
Modur et al., "FOXO proteins regulate tumor necrosis factor-related apoptosis inducing ligand expression. Implications for PTEN mutation in prostate cancer," J. Biol. Chem., 277(49):47928-47937, Dec. 2002.
Moelling et al., "Regulation of Raf-Akt Cross-talk," J. Biol. Chem., 277(34):31099-31106, Aug. 2002.
Nakamura et al., "Forkhead transcription factors are critical effectors of cell death and cell cycle arrest downstream of PTEN," Mol. Cell Biol., 20(23):8969-8982, Dec. 2000.
Nemoto and Finkel, "Redox regulation of forkhead proteins through a p66shc-dependent signaling pathway," Science, 295(5564):2450-2, Mar. 2002.
Okano and Rustgi., "Paclitaxel induces prolonged activation of the Ras/MEK/ERK pathway independently of activating the programmed cell death machinery," J. Biol. Chem., 276(22):19555-19564, Jun. 2001.
Paik et al., "FoxOs are lineage-restricted redundant tumor suppressors and regulate endothelial cell homeostasis," Cell, 128(2):309-23, Jan. 2007.
Pan et al., "Abstract #: 15/3793: Cytoplasmic FOXO1 negatively regulates ERK to overcome taxol resistance in prostate cancer," Presented at AUA Annual Meeting May 15-19, 2015, New Orleans, LA.
Pan et al., "AKT-phosphorylated FOXO1 suppresses ERK activation and chemoresistance by disrupting IQGAP1-MAPK interaction," EMBO J., 36(8):995-1010, Apr. 2017.
Pan et al., "Cytoplasmic FOXO1 negatively regulates ERK to overcome taxol resistance in prostate cancer," Poster, Presented at AUA Annual Meeting May 15-19, 2015, New Orleans, LA.
Pan et al., "MP55-01 Cytoplasmic FOXO1 Negatively Regulates ERK to Overcome Taxol Resistance in Prostate Cancer," The Journal of Urology, 193(4s):e672-e673, May 2015.
Peng and Gygi, "Proteomics: the move to mixtures," J. Mass Spectrom., 36(10):1083-1091, Oct. 2001.
Plas et al., "Akt activation promotes degradation of tuberin and FOXO3a via the proteasome," J. Biol. Chem., 278:12361-6, Apr. 2003.
Ren et al., "IQGAP1 modulates activation of B-Raf," Proc. Natl. Acad. Sci. USA., 104(25):10465-10469, Jun. 2007.
Robertson et al., "Regulation of Erk1/2 activation by osteopontin in PC3 human prostate cancer cells," Mol. Cancer, 9:260, Sep. 2010.
Roy et al, "IQGAP1 binds ERK2 and modulates its activity," J. Biol. Chem., 279(17):17329-17337, Apr. 2004.

(56) References Cited

OTHER PUBLICATIONS

Roy et al, "IQGAP1 is a scaffold for mitogen-activated protein kinase signaling," Mol. Cell Biol. 25(18):7940-7952, Sep. 2005.
Serra et al, "PI3K inhibition results in enhanced HER signaling and acquired ERK dependency in HER2-overexpressing breast cancer," Oncogene 30(22):2547-2557, Jun. 2011.
Shevchenko et al, "Mass spectrometric sequencing of proteins from silver-stained polyacrylamide gels," Anal. Chem., 68(5):850-858, Mar. 1996.
Sunters et al., "Paclitaxel-induced nuclear translocation of FOXO3a in breast cancer cells is mediated by c-Jun NH2-terminal kinase and Akt," Cancer Res., 66(1):212-20, Jan. 2006.
Tan et al., "Key roles of BIM-driven apoptosis in epithelial tumors and rational chemotherapy," Cancer Cell, 7(3):227-38, Mar. 2005.
Tang et al, "Negative regulation of the forkhead transcription factor FKHR by Akt," J. Biol. Chem., 274(24):16741-16746, Jun. 1999.
Van der Horst et al, "FOXO4 transcriptional activity is regulated by monoubiquitination and USP7/HAUSP," Nat. Cell Biol., 8(10):1064-1073, Oct. 2006.
Vander Heiden et al., "Understanding the Warburg effect: the metabolic requirements of cell proliferation," Science, 324(5930):1029-33, May 2009.
Varne et al, "Conformational analysis of the GTP-binding protein MxA using limited proteolysis," FEBS Lett., 516(1-3):129-132, Apr. 2002.
Vivanco et al., "The phosphatidylinositol 3-kinase—AKT pathway in human cancer," Nature Reviews Cancer, 2(7):489-501, Jul. 2002.
Wang et al, "BRCA1 is a negative modulator of the PRC2 complex," EMBO J., 32(11):1584-1597, May 2013.
Wang et al., "Deacetylation of FOXO3 by SIRT1 or SIRT2 leads to Skp2-mediated FOXO3 ubiquitination and degradation," Oncogene, 31:1546-57, Mar. 2012.
White et al, "IQGAP1 and its binding proteins control diverse biological functions," Cellular Signal, 24(4):826-834, Apr. 2012.
Xu et al., "Enhancement of paclitaxel-induced apoptosis by inhibition of mitogen-activated protein kinase pathway in colon cancer cells," Anticancer Res., 29(1):261-70, Jan. 2009.
Yang et al., "ERK1/2-dependent phosphorylation and nuclear translocation of PKM2 promotes the Warburg effect," Nat. Cell Biol., 14(12):1295-304, Dec. 2012.
Yuan et al, "The function of FOXO1 in the late phases of the cell cycle is suppressed by PLK1-mediated phosphorylation," Cell Cycle, 13(5):807-819, Mar. 2014.
Zhang et al, "FOXO1 inhibits Runx2 transcriptional activity and prostate cancer cell migration and invasion," Cancer Res., 71(9):3257-3267, May 2011.
Zhang et al., "FoxO1 regulates multiple metabolic pathways in the liver effects on gluconeogenic, glycolytic, and lipogenic gene expression," Journal of Biological Chemistry, 281(15):10105-17, Apr. 2006.
Bechara and Segan, "Cell-penetrating peptides: 20 years later, where do we stand?," FEBS Letters, Jun. 2013, 587(12):1693-702.
Madani et al., "Mechanisms of cellular uptake of cell-penetrating peptides," Journal of biophysics, Jan. 2011, 10 pages.

\* cited by examiner

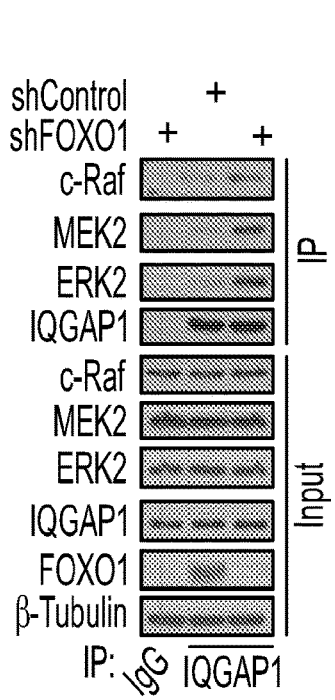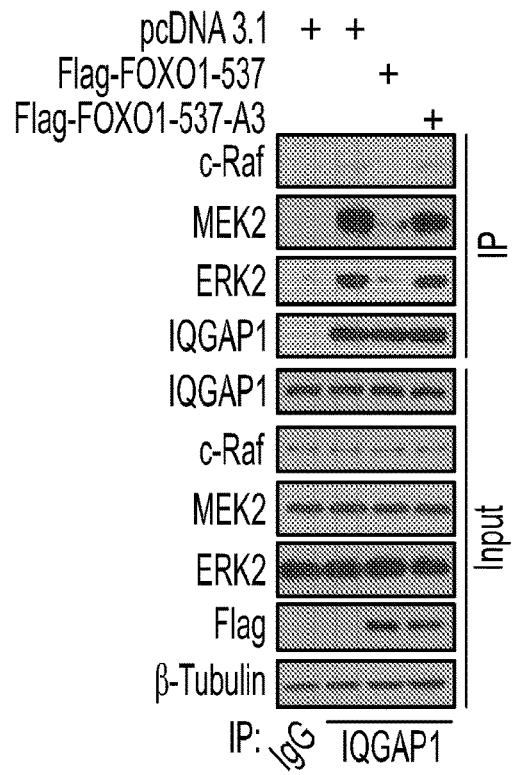
FIG. 5C
FIG. 5D
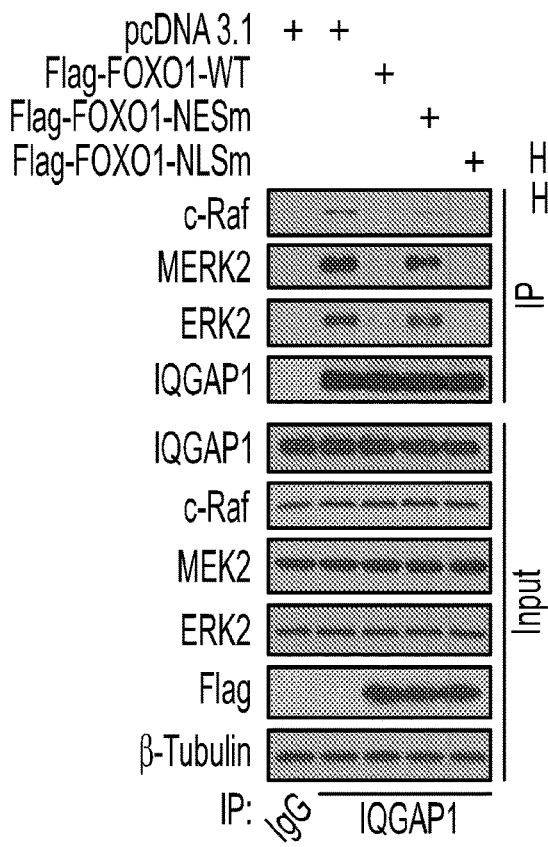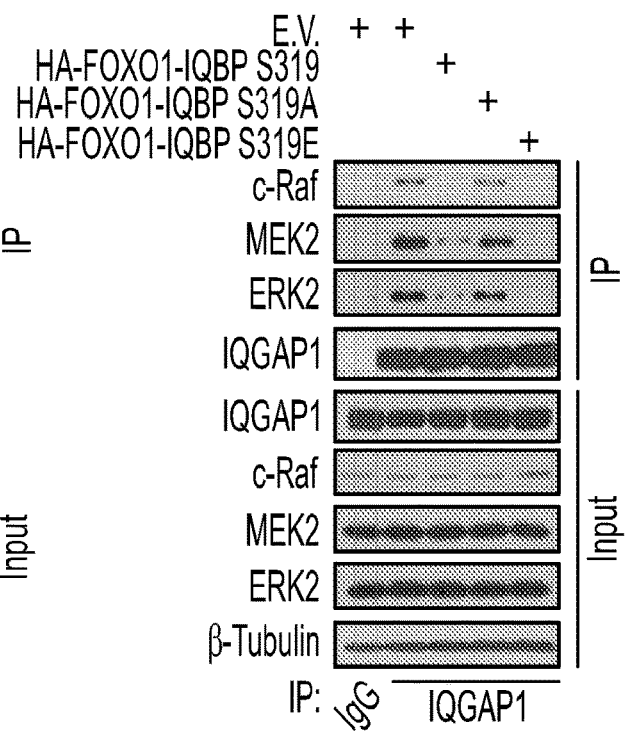
FIG. 5E
FIG. 5F

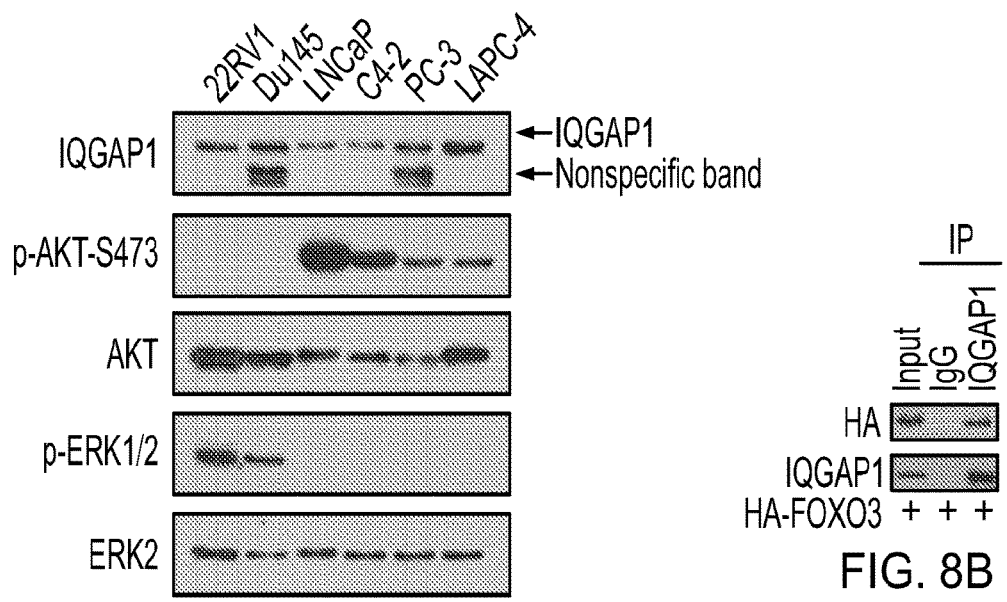
FIG. 8A
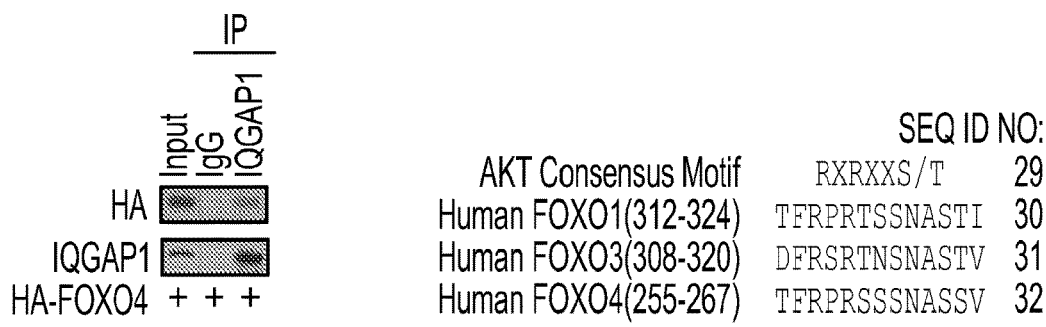
FIG. 8B
|  |  | SEQ ID NO: |
|---|---|---|
| AKT Consensus Motif | RXRXXS/T | 29 |
| Human FOXO1(312-324) | TFRPRTSSNASTI | 30 |
| Human FOXO3(308-320) | DFRSRTNSNASTV | 31 |
| Human FOXO4(255-267) | TFRPRSSSNASSV | 32 |
FIG. 8C   FIG. 8D
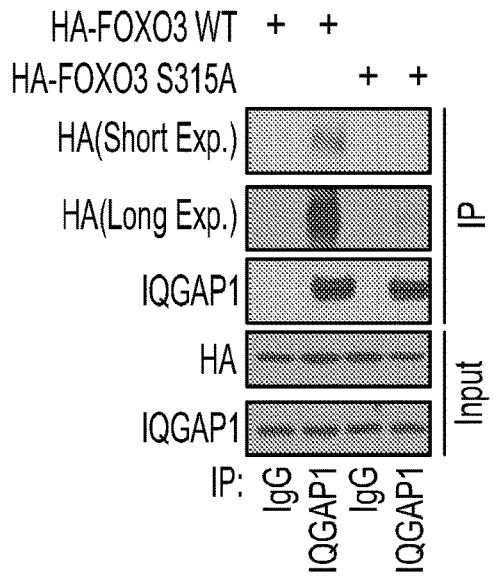
FIG. 8E
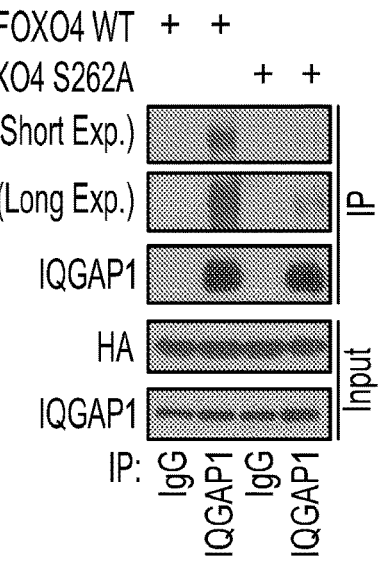
FIG. 8F

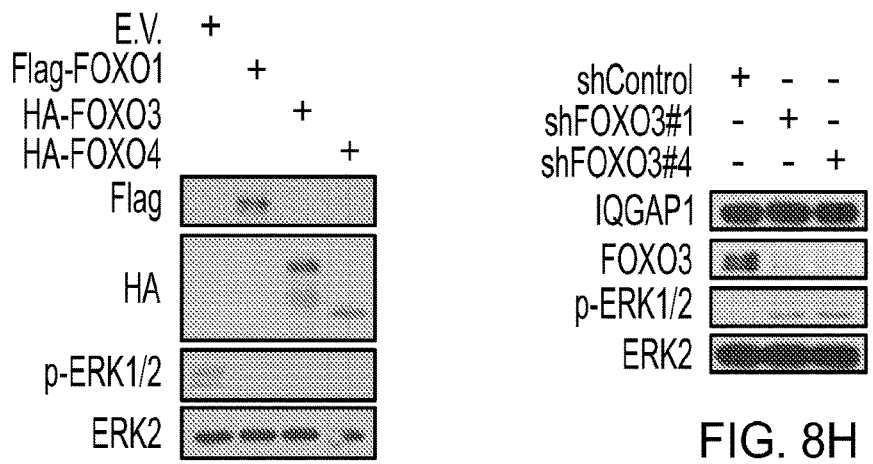
FIG. 8G
FIG. 8H
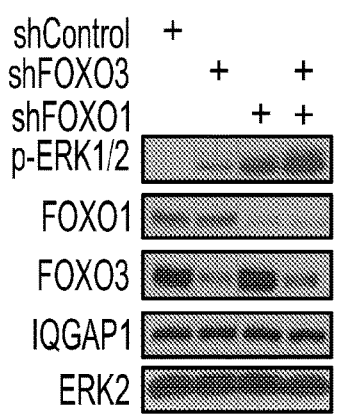
FIG. 8I
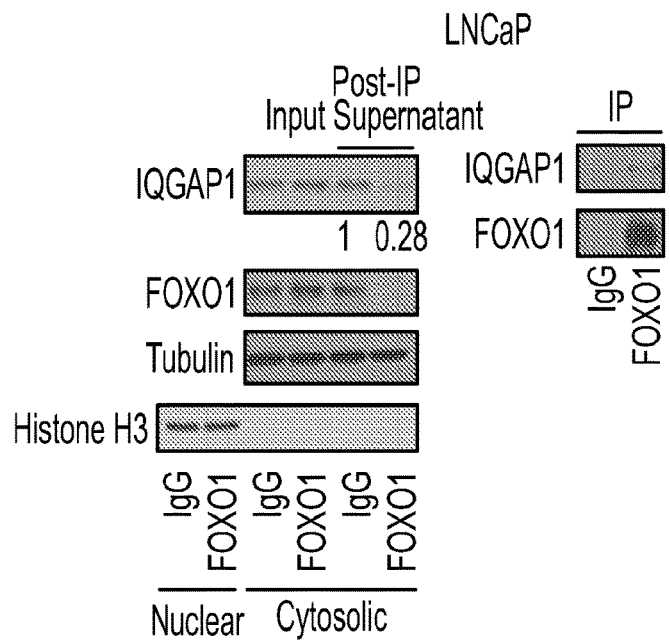
FIG. 8J
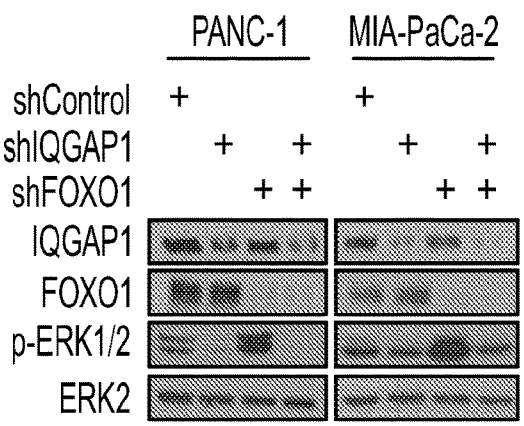
FIG. 8K Quantitative data of Fig 5B

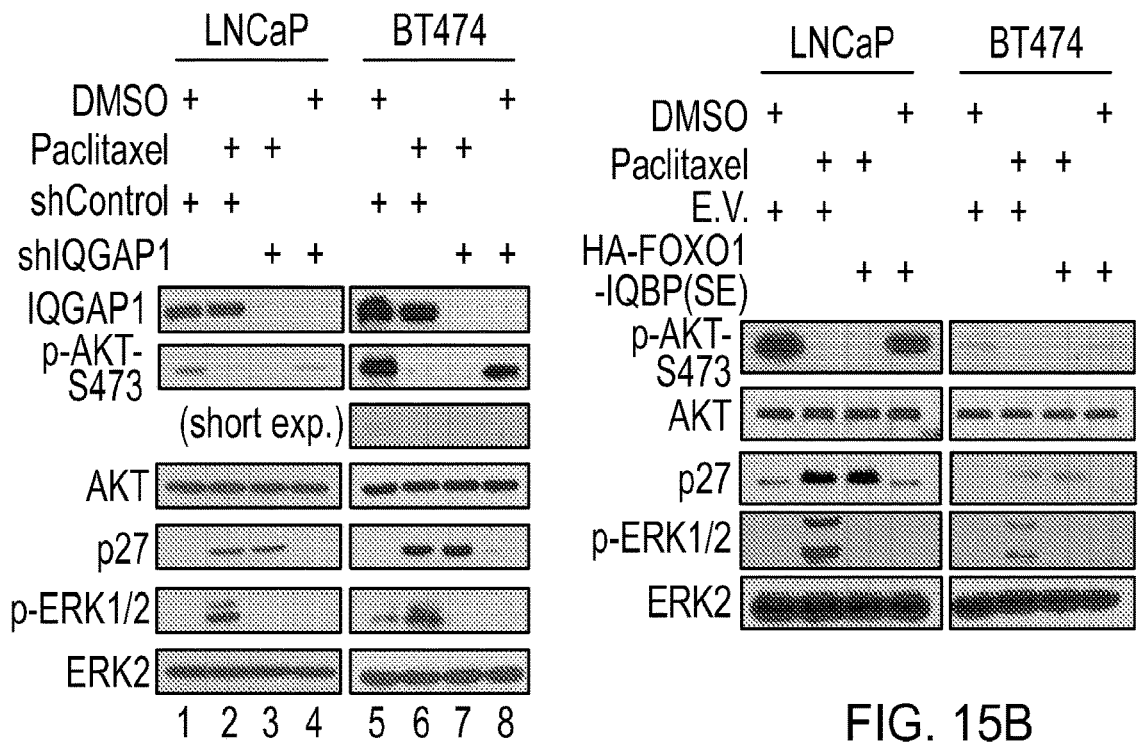
FIG. 15A
FIG. 15B
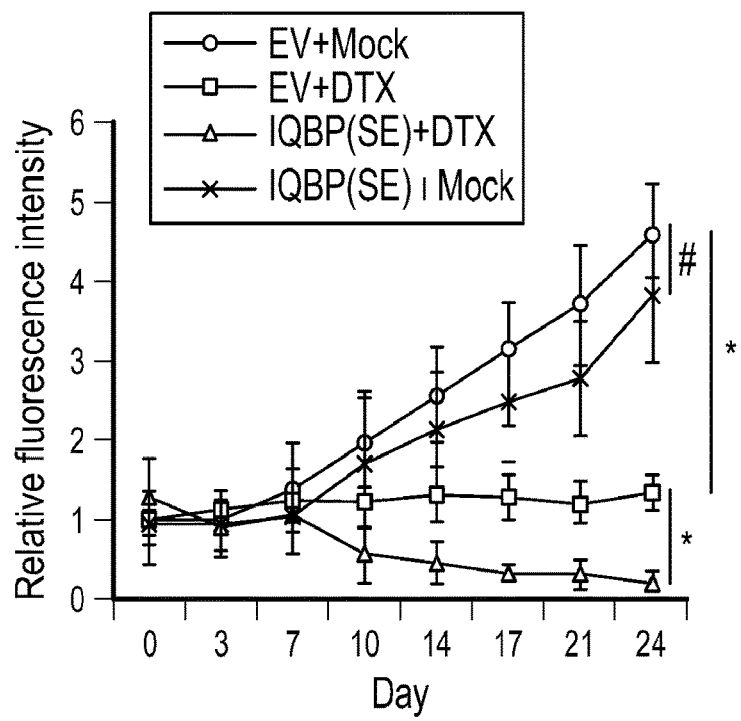
FIG. 15C

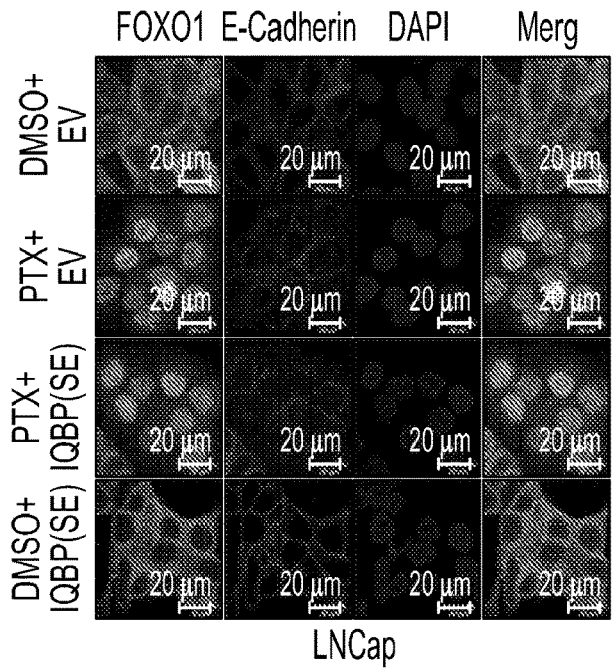
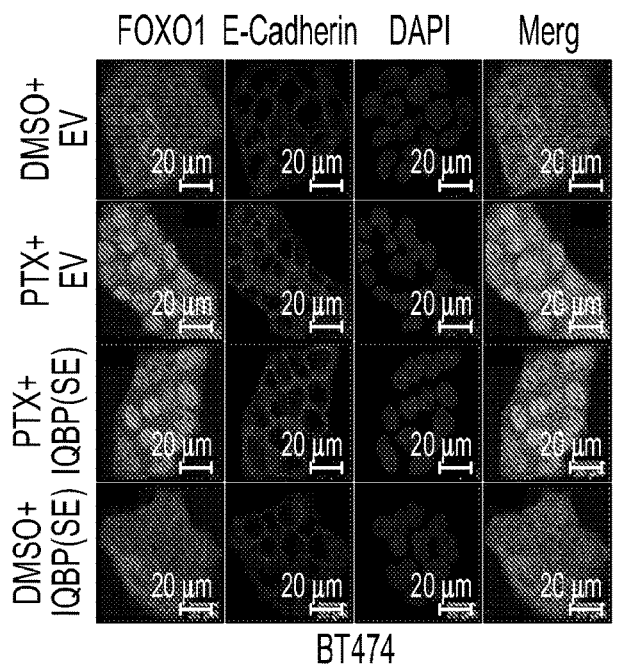
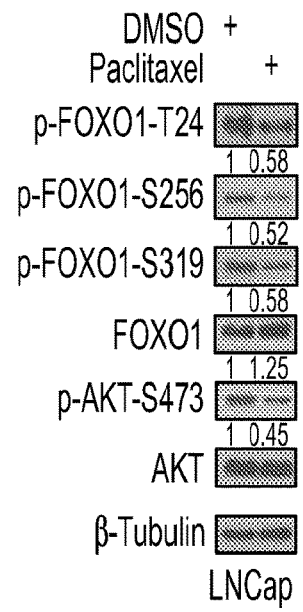
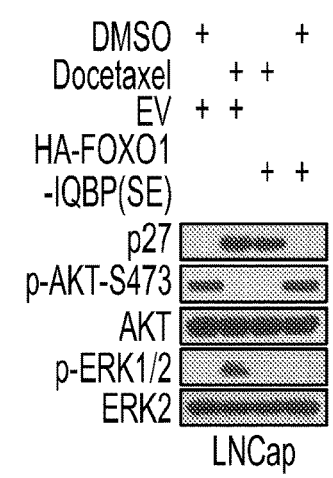
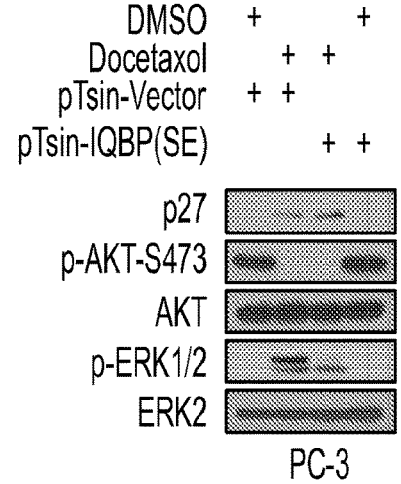
FIG. 16A
FIG. 16B
FIG. 16C
FIG. 16D

SEQUENCE LISTING

```
<160> NUMBER OF SEQ ID NOS: 32

<210> SEQ ID NO 1
<211> LENGTH: 30
<212> TYPE: PRT
<213> ORGANISM: artificial
<220> FEATURE:
<223> OTHER INFORMATION: HA-tagged FOXO1-derived IQGAP1-binding peptide

<400> SEQUENCE: 1

Asn Asp Asp Phe Asp Asn Trp Ser Thr Phe Arg Pro Arg Thr Ser Ser
1               5                   10                  15

Asn Ala Ser Thr Ile Ser Gly Arg Leu Ser Pro Ile Met Thr
            20                  25                  30

<210> SEQ ID NO 2
<211> LENGTH: 30
<212> TYPE: PRT
<213> ORGANISM: artificial
<220> FEATURE:
<223> OTHER INFORMATION: phosphorylation-mimicking FOXO1-derived peptide

<400> SEQUENCE: 2

Asn Asp Asp Phe Asp Asn Trp Ser Thr Phe Arg Pro Arg Thr Ser Glu
1               5                   10                  15

Asn Ala Ser Thr Ile Ser Gly Arg Leu Ser Pro Ile Met Thr
            20                  25                  30
```

<210> SEQ ID NO 3
<211> LENGTH: 30
<212> TYPE: PRT
<213> ORGANISM: artificial
<220> FEATURE:
<223> OTHER INFORMATION: phosphorylation-mimicking FOXO1-derived peptide

<400> SEQUENCE: 3

Asn Asp Asp Phe Asp Asn Trp Ser Thr Phe Arg Pro Arg Thr Ser Asp
1               5                   10                  15

Asn Ala Ser Thr Ile Ser Gly Arg Leu Ser Pro Ile Met Thr
            20                  25                  30

<210> SEQ ID NO 4
<211> LENGTH: 47
<212> TYPE: PRT
<213> ORGANISM: artificial
<220> FEATURE:
<223> OTHER INFORMATION: phosphorylation-mimicking FOXO1-derived peptide

<400> SEQUENCE: 4

Arg Arg Arg Arg Arg Arg Arg Arg Tyr Pro Tyr Asp Val Pro Asp Tyr
1               5                   10                  15

Ala Asn Asp Asp Phe Asp Asn Trp Ser Thr Phe Arg Pro Arg Thr Ser
            20                  25                  30

Glu Asn Ala Ser Thr Ile Ser Gly Arg Leu Ser Pro Ile Met Thr
        35                  40                  45

<210> SEQ ID NO 5
<211> LENGTH: 47
<212> TYPE: PRT
<213> ORGANISM: artificial
<220> FEATURE:
<223> OTHER INFORMATION: phosphorylation-mimicking FOXO1-derived peptide

<400> SEQUENCE: 5

Arg Arg Arg Arg Arg Arg Arg Arg Tyr Pro Tyr Asp Val Pro Asp Tyr
1               5                   10                  15

Ala Asn Asp Asp Phe Asp Asn Trp Ser Thr Phe Arg Pro Arg Thr Ser
            20                  25                  30

Asp Asn Ala Ser Thr Ile Ser Gly Arg Leu Ser Pro Ile Met Thr
        35                  40                  45

<210> SEQ ID NO 6
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: FOXO1 nuclear export signal motif

<400> SEQUENCE: 6

Met Glu Asn Leu Leu Asp Asn Leu Asn Leu
1               5                   10

<210> SEQ ID NO 7
<211> LENGTH: 10
<212> TYPE: PRT
<213> ORGANISM: artificial
<220> FEATURE:
<223> OTHER INFORMATION: mutated FOXO1 nuclear export signal motif

<400> SEQUENCE: 7

Ala Glu Asn Ala Leu Asp Asn Ala Asn Ala
1               5                   10

<210> SEQ ID NO 8
<211> LENGTH: 58
<212> TYPE: DNA
<213> ORGANISM: artificial
<220> FEATURE:
<223> OTHER INFORMATION: shRNA for human IQGAP1

<400> SEQUENCE: 8
ccgggcccac attgtgcctt tatttctcga gaaataaagg cacaatgtgg gcttttg        58

<210> SEQ ID NO 9
<211> LENGTH: 58
<212> TYPE: DNA
<213> ORGANISM: artificial
<220> FEATURE:
<223> OTHER INFORMATION: shRNA for human IQGAP1

<400> SEQUENCE: 9
ccggcctcag attcaagacc tatatctcga gatataggtc ttgaatctga ggttttg        58

<210> SEQ ID NO 10
<211> LENGTH: 58
<212> TYPE: DNA
<213> ORGANISM: artificial
<220> FEATURE:
<223> OTHER INFORMATION: shRNA for human FOXO-1

<400> SEQUENCE: 10
ccgggccgga gtttagccag tccaactcga gttggactgg ctaaactccg gcttttg        58

<210> SEQ ID NO 11
<211> LENGTH: 57
<212> TYPE: DNA
<213> ORGANISM: artificial
<220> FEATURE:
<223> OTHER INFORMATION: shRNA for human FOXO-1

<400> SEQUENCE: 11
ccggatctac gagtggatgg tcaactcgag ttgaccatcc actcgtagat cttttg        57

<210> SEQ ID NO 12
<211> LENGTH: 58
<212> TYPE: DNA
<213> ORGANISM: artificial
<220> FEATURE:
<223> OTHER INFORMATION: shRNA for human FOXO-1

<400> SEQUENCE: 12
ccggcagacc ctcaaactga cacaactcga gttgtgtcag tttgagggtc tgttttg        58

<210> SEQ ID NO 13
<211> LENGTH: 58
<212> TYPE: DNA
<213> ORGANISM: artificial
<220> FEATURE:
<223> OTHER INFORMATION: shRNA for human FOXO-1

<400> SEQUENCE: 13
ccgggtcact gcatagtcga ttcatctcga gatgaatcga ctatgcagtg acttttg        58

<210> SEQ ID NO 14
<211> LENGTH: 59
<212> TYPE: DNA

```
<213> ORGANISM: artificial
<220> FEATURE:
<223> OTHER INFORMATION: shRNA for human PKM2

<400> SEQUENCE: 14
ccgggcccga ggcttcttca agaagctcga gcttcttgaa gaagcctcgg gctttttg      59

<210> SEQ ID NO 15
<211> LENGTH: 59
<212> TYPE: DNA
<213> ORGANISM: artificial
<220> FEATURE:
<223> OTHER INFORMATION: shRNA for human PKM2

<400> SEQUENCE: 15
ccgggttcgg aggtttgatg aaatcctcga ggatttcatc aaacctccga acttttttg     59

<210> SEQ ID NO 16
<211> LENGTH: 59
<212> TYPE: DNA
<213> ORGANISM: artificial
<220> FEATURE:
<223> OTHER INFORMATION: shRNA for human PKM2

<400> SEQUENCE: 16
ccggctttcc tgtgtgtact ctgtcctcga ggacagagta cacacaggaa agttttttg     59

<210> SEQ ID NO 17
<211> LENGTH: 20
<212> TYPE: DNA
<213> ORGANISM: artificial
<220> FEATURE:
<223> OTHER INFORMATION: synthetic primer

<400> SEQUENCE: 17
gctgtgctta tgggcttctc                                                20

<210> SEQ ID NO 18
<211> LENGTH: 20
<212> TYPE: DNA
<213> ORGANISM: artificial
<220> FEATURE:
<223> OTHER INFORMATION: synthetic primer

<400> SEQUENCE: 18
cacatacatg ggcacaaagc                                                20

<210> SEQ ID NO 19
<211> LENGTH: 20
<212> TYPE: DNA
<213> ORGANISM: artificial
<220> FEATURE:
<223> OTHER INFORMATION: synthetic primer

<400> SEQUENCE: 19
tggagtggaa tgaatgttgc                                                20

<210> SEQ ID NO 20
<211> LENGTH: 20
<212> TYPE: DNA
<213> ORGANISM: artificial
<220> FEATURE:
<223> OTHER INFORMATION: synthetic primer

<400> SEQUENCE: 20
atagcccagg atgtgtagcc                                                20
```

<210> SEQ ID NO 21
<211> LENGTH: 24
<212> TYPE: DNA
<213> ORGANISM: artificial
<220> FEATURE:
<223> OTHER INFORMATION: synthetic primer

<400> SEQUENCE: 21
attatttgag gaactccgcc gcct                                          24

<210> SEQ ID NO 22
<211> LENGTH: 23
<212> TYPE: DNA
<213> ORGANISM: artificial
<220> FEATURE:
<223> OTHER INFORMATION: synthetic primer

<400> SEQUENCE: 22
attccgggtc acagcaatga tgg                                           23

<210> SEQ ID NO 23
<211> LENGTH: 27
<212> TYPE: PRT
<213> ORGANISM: artificial
<220> FEATURE:
<223> OTHER INFORMATION: FOXO1- interacting IQGAP1 peptide

<400> SEQUENCE: 23

Lys Thr Val Leu Glu Leu Met Asn Pro Glu Ala Gln Leu Pro Gln Val
1               5                   10                  15

Tyr Pro Phe Ala Ala Asp Leu Tyr Gln Lys Glu
            20                  25

<210> SEQ ID NO 24
<211> LENGTH: 20
<212> TYPE: PRT
<213> ORGANISM: artificial
<220> FEATURE:
<223> OTHER INFORMATION: FOXO1- interacting IQGAP1 peptide

<400> SEQUENCE: 24

Arg Ile Leu Ala Ile Gly Leu Ile Asn Glu Ala Leu Asp Glu Gly Asp
1               5                   10                  15

Ala Gln Lys Thr
            20

<210> SEQ ID NO 25
<211> LENGTH: 21
<212> TYPE: PRT
<213> ORGANISM: artificial
<220> FEATURE:
<223> OTHER INFORMATION: FOXO1- interacting IQGAP1 peptide

<400> SEQUENCE: 25

Lys Leu Glu Gly Val Leu Ala Glu Val Ala Gln His Tyr Gln Asp Thr
1               5                   10                  15

Ile Leu Ile Arg Ala
            20

<210> SEQ ID NO 26
<211> LENGTH: 17
<212> TYPE: PRT
<213> ORGANISM: artificial
<220> FEATURE:

<223> OTHER INFORMATION: FOXO1- interacting IQGAP1 peptide

<400> SEQUENCE: 26

Arg Ser Asn Gln Gln Leu Glu Asn Asp Leu Asn Leu Met Asp Ile Lys
1               5                   10                  15

Ile

<210> SEQ ID NO 27
<211> LENGTH: 11
<212> TYPE: PRT
<213> ORGANISM: artificial
<220> FEATURE:
<223> OTHER INFORMATION: FOXO1- interacting IQGAP1 peptide

<400> SEQUENCE: 27

Lys Leu Ile Phe Gln Met Pro Gln Asn Lys Ser
1               5                   10

<210> SEQ ID NO 28
<211> LENGTH: 27
<212> TYPE: PRT
<213> ORGANISM: artificial
<220> FEATURE:
<223> OTHER INFORMATION: FOXO1- interacting IQGAP1 peptide

<400> SEQUENCE: 28

Arg Phe Gln Pro Gly Glu Thr Leu Thr Glu Ile Leu Glu Thr Pro Ala
1               5                   10                  15

Thr Ser Glu Gln Glu Ala Glu His Gln Arg Ala
            20                  25

<210> SEQ ID NO 29
<211> LENGTH: 6
<212> TYPE: PRT
<213> ORGANISM: artificial
<220> FEATURE:
<223> OTHER INFORMATION: FOXO1 AKT phosphorylation site consensus motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: X is S or T

<400> SEQUENCE: 29

Arg Xaa Arg Xaa Xaa Xaa
1               5

<210> SEQ ID NO 30
<211> LENGTH: 13
<212> TYPE: PRT
<213> ORGANISM: artificial
<220> FEATURE:
<223> OTHER INFORMATION: FOXO1 AKT phosphorylation site

<400> SEQUENCE: 30

Thr Phe Arg Pro Arg Thr Ser Ser Asn Ala Ser Thr Ile
1               5                   10

<210> SEQ ID NO 31
<211> LENGTH: 13

```
<212> TYPE: PRT
<213> ORGANISM: artificial
<220> FEATURE:
<223> OTHER INFORMATION: FOXO1 AKT phosphorylation site

<400> SEQUENCE: 31

Asp Phe Arg Ser Arg Thr Asn Ser Asn Ala Ser Thr Val
1               5                   10

<210> SEQ ID NO 32
<211> LENGTH: 13
<212> TYPE: PRT
<213> ORGANISM: artificial
<220> FEATURE:
<223> OTHER INFORMATION: FOXO1 AKT phosphorylation site

<400> SEQUENCE: 32

Thr Arg Phe Pro Arg Ser Ser Ser Asn Ala Ser Ser Val
1               5                   10
```

MATERIALS AND METHODS FOR TREATING CANCER

CROSS-REFERENCE TO RELATED APPLICATIONS

This application is a National Stage application under 35 U.S.C. § 371 of International Application No. PCT/US2017/021352, having an International Filing Date of Mar. 8, 2017, which claims the benefit of U.S. Patent Application Ser. No. 62/335,785, filed on May 13, 2016. The disclosures of the prior applications are considered part of (and are incorporated by reference in) the disclosure of this application.

STATEMENT OF FEDERALLY SPONSORED RESEARCH

This invention was made with government support under Grant no. CA134514 awarded by the National Institutes of Health. The government has certain rights in the invention.

BACKGROUND

1. Technical Field

This document relates to methods and materials for treating cancer (e.g., chemotherapeutic resistant cancer). In some cases, this document relates to compositions containing a phosphorylation-mimicking peptide (e.g., a phosphorylation-mimicking forkhead box class O1 (FOXO1) derived peptide) to treat a mammal having cancer (e.g., to reduce the number of cancer cells in a mammal) and methods of using such compositions. For example, this document relates to treating a mammal having cancer (e.g., to reduce the number of cancer cells in a mammal) by administering a phosphorylation-mimicking FOXO1-derived peptide to the mammal.

2. Background Information

O-class forkhead factors (FOXO) including FOXO1, FOXO3, FOXO4 and FOXO6, the human orthologs of *Caenorhabditis elegans* DAF-16 and *Drosophila* dFOXO, are a family of transcription factors that activate transcription of genes involved in apoptosis, cell cycle arrest, and oxidative stress detoxification. These findings imply that FOXOs are tumor suppressors. However, many groups found that ubiquitination-dependent degradation of AKT-phosphorylated FOXO proteins is critical for cell transformation, proliferation, survival and insulin resistance (Plas et al., 2003 *J. Biol. Chem.* 278:12361-6; Aoki et al., 2004 *Proc. Natl. Acad. Sci. USA* 101:13613-7; Matsuzaki et al., 2003 *Proc. Natl. Acad. Sci. USA* 100:11285-90; Huang et al., 2005 *Proc. Natl. Acad. Sci. USA* 102:1649-54; Wang et al., 2012 *Oncogene* 31:1546-57).

Paclitaxel and its semisynthetic analogue docetaxel (DTX) are widely used chemotherapeutic agents for treatment of solid tumors. It is well documented that in both preclinical and clinical settings, activation of the Ras-Raf-MAPK pathway confers resistance to paclitaxel (Okano et al., 2001 *J. Biol. Chem.* 276:19555-64; Sunters et al., 2006 *Cancer Res.* 66:212-20; Mehnert et al., 2011 *Mol. Cancer Ther.* 10:1509-19).

SUMMARY

This document provides methods and materials for treating cancer (e.g., chemotherapeutic resistant cancer). In some cases, this document provides compositions containing a phosphorylation-mimicking peptide (e.g., a phosphorylation-mimicking FOXO1-derived peptide) to treat a mammal having cancer (e.g., to reduce the number of cancer cells in a mammal) and methods of using such compositions. For example, this document provides methods of treating a mammal having cancer (e.g., to reduce the number of cancer cells in a mammal) by administering a phosphorylation-mimicking FOXO1-derived peptide to the mammal.

As described herein, phosphorylation at serine 319 of FOXO1 activates tumor suppressor functions of FOXO1 in inhibition of ERK activation, the Warburg effect, and chemotherapy resistance in cancer. Also as described herein, a 30 amino acid phosphorylation-mimicking peptide derived from a human FOXO1 protein (in which serine 319 is engineered into glutamic acid (S319E) or aspartic acid (S319D)) can be used to treat cancer cells and overcome chemotherapy resistance.

In general, one aspect of this document features a phosphorylation-mimicking FOXO1 derived peptide having a modification (e.g., an amino acid substitution) at position 319. The substitution can be a glutamic acid (E) or aspartic acid (D) at position 319. The phosphorylation-mimicking FOXO1 derived peptide can be derived from a human FOXO1 peptide. A phosphorylation-mimicking FOXO1 derived peptide having a glutamic acid at position 319 can include the amino acid sequence NDDFDNWSTFRPRTSENASTISGRLSPIMT (SEQ ID NO:2). A phosphorylation-mimicking FOXO1 derived peptide having an aspartic acid at position 319 can include the amino acid sequence NDDFDNWSTFRPRTSDNASTISGRLSPIMT (SEQ ID NO:3). The phosphorylation-mimicking FOXO1 derived peptide can include an epitope tag (e.g., a hemagglutinin (HA) tag). The phosphorylation-mimicking FOXO1 derived peptide can include a cell-penetrating peptide. A cell-penetrating peptide can include 8 arginine residues (e.g., 8 D-arginine residues). A phosphorylation-mimicking FOXO1 derived peptide having a glutamic acid at position 319 can include the amino acid sequence RRRRRRRRYPYDVPDY-ANDDFDNWSTFRPRTSENASTISGRLSPIMT (SEQ ID NO:4), where the arginine residues at positions 1-8 can be D-arginine residues. A phosphorylation-mimicking FOXO1 derived peptide having an aspartic acid at position 319 can include the amino acid sequence RRRRRRRRYPYDVPDY-ANDDFDNWSTFRPRTSDNASTISGRLSPIMT (SEQ ID NO:5), where the arginine residues at positions 1-8 are can be D-arginine residues.

In another aspect, this document features a treating cancer in a mammal. The method includes, or consists essentially of, identifying said mammal as having cancer, and administering to the mammal a phosphorylation-mimicking FOXO1 derived peptide having a substitution (e.g., a glutamic acid or an aspartic acid) at position 319. The cancer can be a chemotherapeutic resistant cancer such as a taxane (e.g., paclitaxel or docetaxel) resistant cancer). The cancer can be prostate cancer, breast cancer, pancreatic cancer, ovarian cancer, or colorectal cancer. The cancer can be a taxane resistant prostate cancer. The mammal can be a human. The phosphorylation-mimicking FOXO1 derived peptide can be derived from a human FOXO1 peptide. The phosphorylation-mimicking FOXO1 derived peptide can include the amino acid sequence NDDFDNWSTFRPRTSENASTISGRLSPIMT (SEQ ID NO:2). The phosphorylation-mimicking FOXO1 derived peptide can include the amino acid sequence NDDFDNWSTFRPRTSDNASTISGRL-SPIMT (SEQ ID NO:3). The phosphorylation-mimicking FOXO1 derived peptide can include the amino acid sequence RRRRRRRRYPYDVPDYANDDFDNWSTFR-PRTSENASTISGRLSPIMT (SEQ ID NO:4), where the arginine residues at positions 1-8 can be D-arginine residues. The phosphorylation-mimicking FOXO1 derived peptide can include the amino acid sequence RRRRRRRRY-PYDVPDYANDDFDNWSTFRPRTSDNASTISGRL-SPIMT (SEQ ID NO:5), where the arginine residues at positions 1-8 can be D-arginine residues.

In another aspect, this document features a method for decreasing polypeptide expression in cells. The method includes, or consists essentially of, contacting the cells with a phosphorylation-mimicking FOXO1 derived peptide having a substitution (e.g., a glutamic acid or an aspartic acid) at position 319, wherein expression of one or more of GLUT1, LDHA, and/or PKM2 is decreased. The cells can be cancer cells. The cancer cells can be chemotherapeutic resistant cancer cells (e.g., taxane resistant cancer cells). The taxane resistant cancer cells can be prostate, breast, pancreatic, ovarian, or colorectal taxane resistant cancer cells. The taxane resistant cancer cells can be taxan resistant prostate cancer cells. The cells can be human cells. The phosphorylation-mimicking FOXO1 derived peptide can be derived from a human FOXO1 peptide. The phosphorylation-mimicking FOXO1 derived peptide can include the amino acid sequence NDDFDNWSTFRPRTSENASTISGRLSPIMT (SEQ ID NO:2). The phosphorylation-mimicking FOXO1 derived peptide can include the amino acid sequence NDDFDNWSTFRPRTSDNASTISGRLSPIMT (SEQ ID NO:3). The phosphorylation-mimicking FOXO1 derived peptide can include the amino acid sequence RRRRRRR-RYPYDVPDYANDDFDNWSTFRPRTSENASTISGRL-SPIMT (SEQ ID NO:4), where the arginine residues at positions 1-8 can be D-arginine residues. The phosphorylation-mimicking FOXO1 derived peptide can include the amino acid sequence RRRRRRRRYPYDVPDY-ANDDFDNWSTFRPRTSDNASTISGRLSPIMT (SEQ ID NO:5), where the arginine residues at positions 1-8 can be D-arginine residues.

In another aspect, this document features a nucleic acid encoding the phosphorylation-mimicking FOXO1 derived peptide having a substitution (e.g., a glutamic acid or an aspartic acid) at position 319. This document also features expression vectors including a nucleic acid encoding the phosphorylation-mimicking FOXO1 derived peptide having a substitution (e.g., a glutamic acid or an aspartic acid) at position 319. Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

Figure 1A:
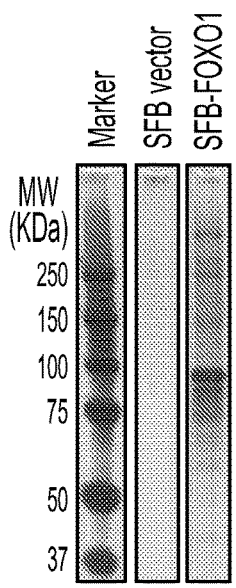
FIG. 1 shows that IQGAP1 interacts with FOXO1 in vitro and in vivo. A) SDS-PAGE and silver staining of proteins purified by tandem affinity purification using lysates of 293T cells transiently transfected with control vector and SFB-tagged FOXO1 for 24 hours. Six IQGAP1 peptides detected by mass spectrometry are shown. B and C) Western blot detection of co-immunoprecipitated endogenous FOXO1 and IQGAP1 proteins in LNCaP cells. D) Schematic diagram depicting a set of GST-FOXO1 recombinant protein constructs. E) Western blot analysis of IQGAP1 proteins in DU145 whole cell lysate pulled down by GST or GST-FOXO1 recombinant proteins. F) In vitro protein binding assay. GST and GST-FOXO1-3 (amino acids 211-419) purified from bacteria were subjected to AKT kinase assay with IgG or HA-AKT-CA immunoprecipitated from HA-AKT-CA-transfected C4-2 cells before incubating with in vitro translated Flag-IQGAP1 for protein binding assay.

(S319) and non-phosphorylatable (S319A) counterparts. 24 hours after transfection, cells were harvested and lysed for co-IP with IgG or anti-IQGAP1 antibodies and immunoprecipitated proteins were analyzed by western blotting using indicated antibodies. G) Limited proteolysis assay. Limited proteolysis of GST-IQGAP1 incubated with GST-FOXO1-IQBP S319E or GST alone using trypsin. Proteolysis was carried out on ice for the times indicated under each lane. The products of proteolysis were resolved by 13.5% acrylamide SDS-PAGE and visualized by staining with Coomassie blue. The experiments were repeated once and similar results were obtained.

FIG. 8 shows an assessment of the interaction of IQGAP1 with FOXO3 and FOXO4, their effect on ERK1/2 phosphorylation and effect of FOXO1 on ERK1/2 phosphorylation in non-prostate cancer cells. A) Western blot analysis of expression of phospho-AKT (serine 473) and ERK1/2 in prostate cancer cell lines indicated. Arrow indicates non-specific reaction protein bands. B and C) Western blot analysis of whole cell lysate (WCL) and co-immunoprecipitation (co-IP) samples of IgG or anti-IQGAP1 antibody from LNCaP cells 24 hours after transfected with HA-FOXO3 (B) or HA-FOXO4 (C). D) Comparison of S319, an AKT phosphorylation site in FOXO1 with the homologous site in FOXO3 (S315) and FOXO4 (S262) by multiple sequence alignments. E and F) Western blot analysis of WCL and co-IP samples from LNCaP cells 24 hours after transfected with indicated plasmids. G) Western blot analysis of WCL from DU145 cells 24 hours transfected with indicated plasmids. E.V., empty vector. H and I) Western blot analysis of WCL from LNCaP cells 48 hours after infected with lentivirus expressing indicated shRNAs. J) Western blot analysis of indicated proteins in cytosolic fractionation (input), the supernatant post IP and co-IP samples from LNCaP cells. Nuclear fractionation was used to indicate the effectiveness of the fractionation. K) Western blot analysis of WCL from PANC-1 and MIA-PaCa-2 cells 48 hours after infected with lentivirus expressing indicated shRNAs.

FIG. 9 shows that AKT-phosphorylated FOXO1 inhibits IQGAP1-dependent pERK1/2. A-C) Western blot analysis of whole cell lysates (WCL) from LNCaP cells 48 hours after infected with lentivirus expressing indicated shRNA and shRNA-resistant plasmids. D and E) Western blot analysis of WCL from C4-2 cells 24 hours after transfected with indicated plasmids. Cells were treated with or without 10 ng/mL of epidermal growth factor (EGF) for 10 minutes before harvested. F) Representative images of hematoxylin-eosin staining and immunohistochemical staining of anti-FOXO1 and anti-pERK1/2 antibodies on TMA (n=261) tissue sections. G and H) Heat map (G) and Waterfall diagram (H) showing the immunohistochemical staining index (IHC SI) of FOXO1 and pERK1/2 in TMA and association with tumor Gleason scores. The scale bar in (G) indicates IHC SI, any of which greater than 60 were colored in red.

FIG. 10 shows quantitative data of the western blots shown in FIG. 9. A) Western blot bands of p-ERK1/2, in cells infected with lentivirus expressing control shRNA (shControl) or two independent FOXO1-specific shRNAs (#1 and #2) as shown in FIG. 9A and the repeated experiment (replication 2), were quantified and normalized to the quantified value of total ERK2. The normalized values were further normalized to the value in cells infected with shFOXO1 #1. The data from two replicates (n=2) were used to generate the figure shown in this panel. B) Western blot bands of p-ERK1/2, in cells infected with lentivirus expressing control shRNA (shControl) or two independent FOXO1-specific shRNAs (#1 and #2) with or without shRNA-resistant Flag-tagged FOXO1 (S1R or S2R) as shown in FIG. 9B and the repeated experiment (replication 2), were quantified and normalized to the quantified value of total ERK2. The normalized values were further normalized to the value in cells infected with shFOXO1 #1. The data from two replicates (n=2) were used to generate the figure shown in this panel. C) Western blot bands of p-ERK1/2, in cells infected with lentivirus expressing control shRNA (shControl), FOXO1-specific shRNA, and/or IQGAP1-specific shRNA as shown in FIG. 9C and the repeated experiment (replication 2), were quantified and normalized to the quantified value of total ERK2. The normalized values were further normalized to the value in cells infected with shFOXO1. The data from two replicates (n=2) were used to generate the figure shown in this panel. D) Western blot bands of p-ERK1/2, in cells transfected with Myc-IQGAP1 with or without Flag-tagged transcription-deficient Flag-FOXO1-537 (can be phosphorylated by AKT) or with or without Flag-FOXO1-537-A3 (resistant to AKT phosphorylation) as shown in FIG. 9D and the repeated experiment (replication 2), were quantified and normalized to the quantified value of total ERK2. The normalized values were further normalized to the value in cells transfected with Myc-IQGAP1. The data from two replicates (n=2) were used to generate the figure shown in this panel. E) Western blot bands of p-ERK1/2, in cells transfected with empty vector (EV, pcDNA3.1), Flag-tagged transcription-deficient Flag-FOXO1-537 (can be phosphorylated by AKT) or Flag-FOXO1-537-A3 (resistant to AKT phosphorylation) and with or without EGF treatment as shown in FIG. 9E and the repeated experiment (replication 2), were quantified and normalized to the quantified value of total ERK2. The normalized values were further normalized to the value in cells transfected with EV and treated with EGF. The data from two replicates (n=2) were used to generate the figure shown in this panel.

FIG. 11 shows that AKT-phosphorylated FOXO1 inhibits PI3K/AKT inhibitor-induced ERK activation. A) Western blot analysis of whole cell lysates (WCL) of LNCaP, C4-2, and C4-2B cells 24 hours after treated with the AKT inhibitor MK2206 (0.5 µM) or the PI3K/mTOR dual inhibitor NVP-BEZ235 (50 nM). B) Western blot analysis of WCL of LNCaP cells 48 hours after transfection with indicated plasmids. Cells were treated with or without MK2206 (0.5 µM) for 24 hours prior to harvest. E.V., empty vector. C) Western blot analysis of WCL of LNCaP cells 48 hours transfected with indicated plasmids. Cells were pre-treated with or without CHX (20 µg/ml) for 30 minutes and then treated with or without MK2206 (0.5 µM) for 24 hours. D) LNCaP cells were transfected with empty vector (E.V.) or a phospho-mimicking peptide HA-FOXO1-IQBP(SE) for 24 hours and then were treated with or without MK2206 (0.5 µM) followed by MTS assay at indicated time points (means±s.d., n=6). *P=0.00014608 comparing MK2206 versus DMSO; P=4.28734E-07 comparing MK2206+EV versus MK2206+IQBP(SE) (Two-sided student t test at the 48-hour time point). E) Western blot analysis of WCL of LNCaP cells 72 hours after infected with lentivirus expressing indicated shRNAs. Cells were pre-treated with or without CHX (20 µg/ml) for 30 minutes prior to being treated with or without MK2206 (0.5 µM) for 24 h. F) LNCaP cells were infected with lentivirus expressing indicated shRNAs for 72 hours and then treated with or without MK2206 (0.5 µM) followed by MTS assay at indicated time points (means±s.d., n=6). *P=6.71297E-07 comparing shControl versus shControl+MK2206; P=1.92261E-12 comparing shIQGAP1-1 versus shIQGAP1-1+MK2206; P=6.87256E-12 comparing shIQGAP1-2 versus shIQGAP1-2+MK2206; P=1.64547E-07 comparing shIQGAP1-1 versus shControl; P=1.68294E-08 comparing shIQGAP1-2 versus shControl; P=2.91871E-14 comparing shIQGAP1-1+MK2206 versus shControl+MK2206; P=8.95133E-15 comparing shIQGAP1-2+MK2206 versus shControl+MK2206 (two-sided student t test at the 48-hour time point).

FIG. 12 shows quantitative data of the western blots shown in FIG. 11. A) Western blot bands of p-AKT-S473 (p-FOXO1-S319 or p-ERK1/2), in LNCaP cells (left panel), C4-2 cells (middle panel) or C4-2B cells (right panel) treated with vehicle (DMSO), the AKT inhibitor MK2206 or the PI3K/mTOR dual inhibitor NVP-BEZ235 as shown in FIG. 11A and the repeated experiment (replication 2), were quantified and normalized to the quantified value of total AKT (total FOXO1 or total ERK2). The normalized values were further normalized to the value in cells treated with DMSO. The data from two replicates (n=2) were used to generate the figure shown in this panel. B) Western blot bands of p-AKT-S473 (p-FOXO1-S319 or p-ERK1/2), in LNCaP cells transfected with empty vector (EV) or expression vector for small FOXO1 phospho-mimicking peptide HA-FOXO1-IQBP(SE) and treated with or without the AKT inhibitor MK2206 and/or the new protein synthesis inhibitor cycloheximide (CHX) as shown in FIG. 11B and the repeated experiment (replication 2), were quantified and normalized to the quantified value of total AKT (total FOXO1 or total ERK2). The normalized values were further normalized to the value in cells transfected with EV and treated with vehicle. The data from two replicates (n=2) were used to generate the figure shown in this panel. C) Western blot bands of p-AKT-S473 (p-FOXO1-S319 or p-ERK1/2), in LNCaP cells transfected with control vector pcDNA3.1, Flag-FOXO1-NESm or Flag-FOXO1-NLSm and treated with vehicle (DMSO) or the AKT inhibitor MK2206 as shown in FIG. 11C and the repeated experiment (replication 2), were quantified and normalized to the quantified value of total AKT (total FOXO1 or total ERK2). The normalized values were further normalized to the value in cells transfected with pcDNA3.1 and treated with vehicle. The data from two replicates (n=2) were used to generate the figure shown in this panel. D) Western blot bands of p-AKT-S473 (p-FOXO1-S319 or p-ERK1/2), in LNCaP cells transfected with control shRNA (shControl) or two independent IQGAP1-specific shRNA shIQGAP1-1 and shIQGAP1-2 and treated with or without the AKT inhibitor MK2206 and/or the new protein synthesis inhibitor cycloheximide (CHX) as shown in FIG. 11E and the repeated experiment (replication 2), were quantified and normalized to the quantified value of total AKT (total FOXO1 or total ERK2). The normalized values were further normalized to the value in cells transfected with shControl and treated with vehicle. The data from two replicates (n=2) were used to generate the figure shown in this panel.

Figure 13A:
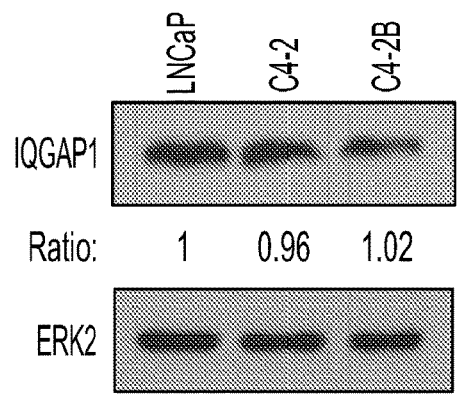

FIG. 13 shows an assessment of IQGAP1 protein expression in PCa cell lines and effect of PI3K/AKT inhibitors and CHX on cellular localization of FOXO1. A) Western blot analysis of IQGAP1 protein expression in prostate cancer cell lines LNCaP, C4-2 and C4-2B. ERK2 was used as loading control. The density of IQGAP1 was determined by normalizing to ERK2 first and then to the normalized value in LNCaP cells. B) Immunofluorescent cytochemistry using anti-FOXO1 antibody in LNCaP (PTEN-negative and FOXO1 in the cytoplasm) cells treated with DMSO, MK2206 (0.5 NVP-BEZ235 (50 nM) and CHX (20 μg/ml) for 24 hours. >100 cells in each experimental condition were analyzed. The experiment was repeated at least once and similar results were obtained.

FIG. 14 shows an assessment of effect of FOXO1 phospho-mimicking peptide on AKT inhibitor-induced cell death and pERK1/2. A and B) LNCaP cells were transfected with empty vector (E.V.) or the FOXO1 phospho-mimicking peptide HA-FOXO1-IQBP(SE) for 24 hours and then treated with or without MK2206 (0.5 μM) for 24 hours followed by immunofluorescent cytochemistry using anti-HA antibody (A) and Annexin V assay and flow cytometry analysis (B). For panel (A), >100 cells in each experimental condition were analyzed. The experiment was repeated at least once and similar results were obtained. For panel (B), data from two biological replicates were quantified (means±s.d., n=2). *P=0.001687442 comparing MK2206 versus DMSO; P=0.014293987 comparing MK2206+EV versus MK2206+IQBP(SE) (Two-sided student t test at the 48-hour time point). C) Western blot analysis of whole cell lysate from indicated cell lines 24 hours after transfected with empty vector (E.V.) and the FOXO1 phospho-mimicking peptide HA-FOXO1-IQBP(SE) and then treated with or without MK2206 (0.5 μM) for 24 hours. D) Annexin V assay and flow cytometry analysis. 72 hour infected with lentivirus expressing indicated shRNAs, LNCaP cells treated with or without MK2206 (0.5 μM) for 24 hours. Quantitative data were obtained from two biological replicates (means±s.d., n=2). *P=0.004378751 comparing shControl versus shControl+MK2206; P=0.001300305 comparing shIQGAP1-1 versus shIQGAP1-1+MK2206; P=0.000967413 comparing shIQGAP1-1 versus shControl; P=0.000363332 comparing shIQGAP1-2 versus shControl; P=0.000232676 comparing shIQGAP1-1+MK2206 versus shControl+MK2206; P=0.000180198 comparing shIQGAP1-2+MK2206 versus shControl+MK2206 (two-sided student t test at the 48-hour time point).

Figure 15D:
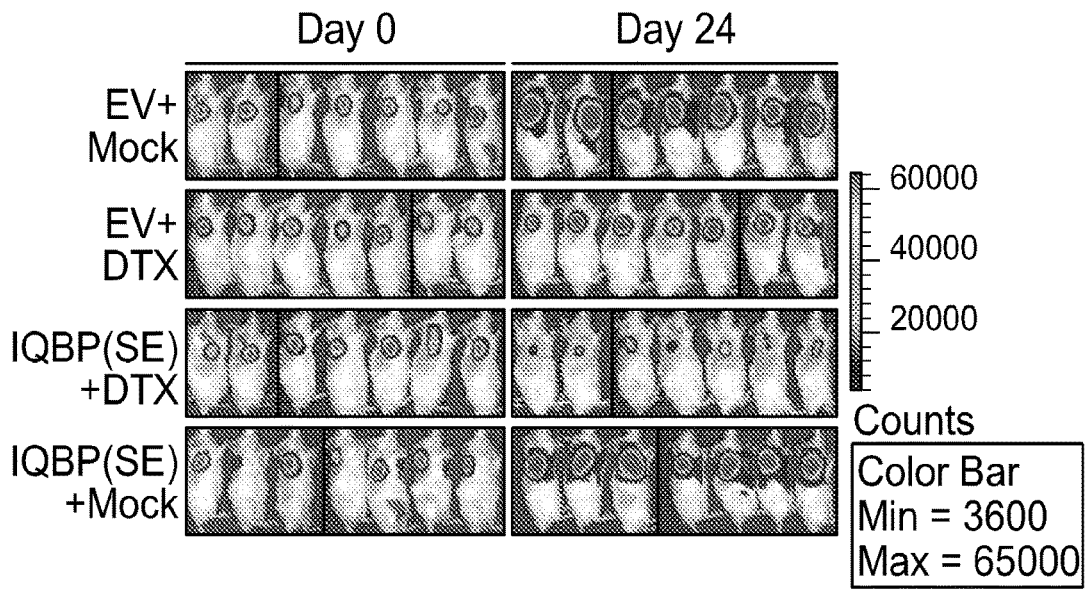
Figure 15E:
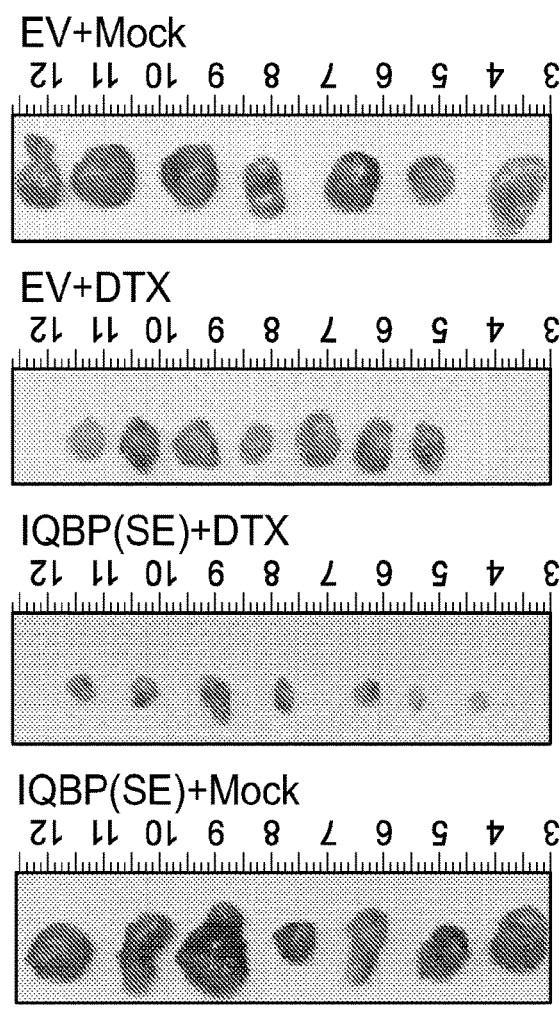
Figure 15F:
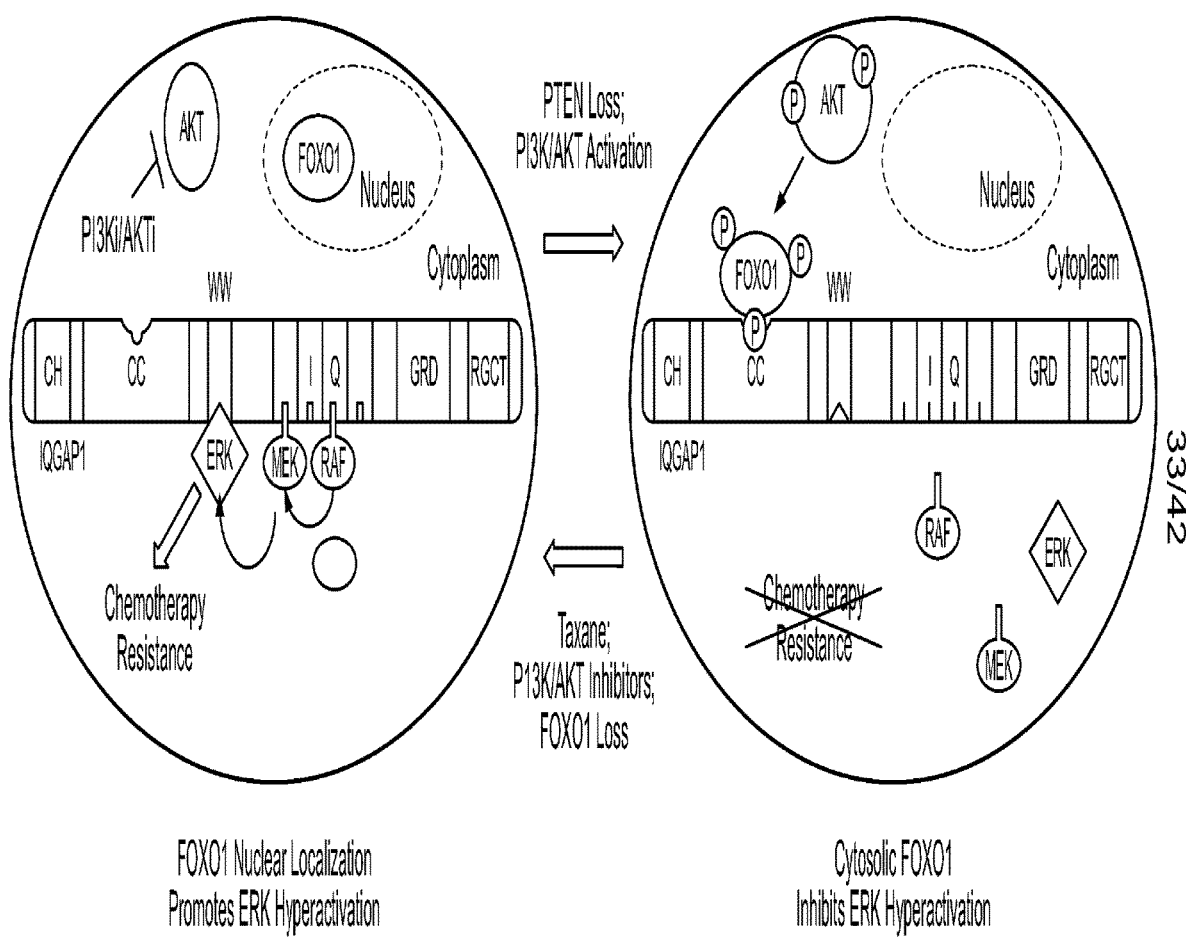

FIG. 15 shows that a small FOXO1-derived peptide inhibitor overcomes taxane-induced ERK activation and chemoresistance. A) Western blot analysis of whole cell lysates (WCL) of LNCaP and BT474 cells 72 hours after infected with lentivirus expressing indicated shRNAs. Cells were treated with or without paclitaxel (10 nM) for 24 hours before harvest. Short exp., short exposure. B) Western blot analysis of WCL of LNCaP and BT474 cells 72 hour infected with lentivirus expressing indicated plasmids. Cells were treated with or without paclitaxel (10 nM) for 24 hours prior to harvest. C-E) PC-3-Luc cells 72 h after infected with lentivirus expressing an empty vector (EV) or the small FOXO1-derived peptide FOXO1-IQBP(SE) were injected subcutaneously into the right flank of NSG mice for 10 days and mice were treated with intravenous DTX (5 mg/kg) or normal saline (mock) twice per week. Luminescent signal intensity in each xenograft at each time point (C), representative luminescent images of xenografts (D), tumors at the end of treatment (E) are shown. The data are presented as means (s.d., n=7). #P=0.18457778 comparing EV+MOCK versus IQBP(SE)+MOCK; *P=0.001033546 comparing EV+MOCK versus EV+DTX, *P=0.000356333 comparing IQBP(SE)+DTX versus EV+DTX (Two sided student t test at the 24-day time point). F) A hypothetical model depicting a rheostat role of AKT-phosphorylated FOXO1 in regulation of activation of the MAPK pathway by the PI3K-PTEN-AKT signaling axis. P in a small red circle, phosphorylation; PI3Ki/AKTi, PI3K and AKT inhibitors.

Figure 16E:
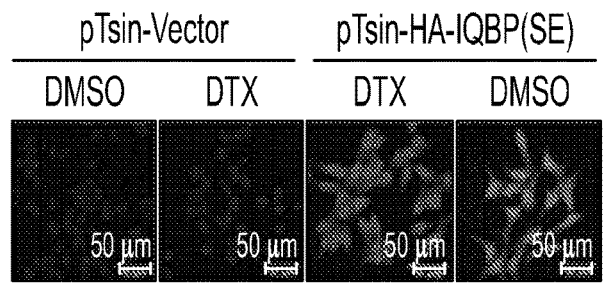

FIG. 16 shows that the FOXO1 small peptide inhibits taxol-induced ERK activation and chemoresistance. A) Immunofluorescent cytochemistry using indicated antibodies in LNCaP and BT474 cells 24 hours after transfected with empty vector (EV) or FOXO1-IQBP(SE) and then treated with or without paclitaxel (PTX) (10 nM) for 24 hours. E-Cadherin was used to mark the plasma membrane (cell boundary). >100 cells were analyzed in each experimental condition. The experiment was repeated at least once and similar results were obtained. B) Western blot analysis of whole cell lysate (WCL) from LNCaP cells treated with or without paclitaxel (10 nM) for 24 hours before harvest. C) Western blot analysis of WCL from LNCaP cells 24 hours after transfected with indicated plasmids and then treated with or without docetaxel (10 nM) for 24 hours. D) Western blot analysis of WCL from PC-3-Luc cells 72 hours after infected with lentivirus expressing empty vector (pTsin) or FOXO1-IQBP(SE). Cells were then treated with or without docetaxel (10 nM) for 24 hours prior to harvest. E) Immunofluorescent cytochemistry using anti-HA antibody in PC-3-Luc cells 72 hours after infected with lentivirus expressing indicated empty vector or HA-FOXO1-IQBP (SE). Cells were then and treated with or without docetaxel (10 nM) for 24 hours. >100 cells were analyzed in each experimental condition. The experiment was repeated at least once and similar results were obtained. F) Immunofluorescent histochemistry using anti-phospho-ERK (p-ERK) and anti-HA antibodies in frozen sections acquired from indicated mouse xenografts harvested at the end of treatment. >100 cells were analyzed in each experimental condition. Similar experiments were performed at least in samples obtained from three animals (n=3). G) MTS assay performed in PC-3-Luc cells. 72 hours after infected with lentivirus expressing empty vector (EV) or HA-IQBP(SE), cells were treated with or without docetaxel (10 nM) for 24 hours (means±s.d., n=6). *P=1.24674E-07 comparing EV+DMSO versus EV+DTX; P=3.29127E-07 comparing IQBP(SE)+DTX versus EV+DTX.

FIG. 17 shows quantitative data of the western blots shown in FIG. 15. A) Western blot bands of p-AKT-5473 (or p-ERK1/2), in LNCaP (left panel) and BT474 (right panel) cells infected with lentivirus expressing control shRNA (shControl) or IQGAP1-specific shRNA shIQGAP1 and treated with vehicle (DMSO) or paclitaxel as shown in FIG. 15A and the repeated experiment (replication 2), were quantified and normalized to the quantified value of total AKT (or total ERK2). The normalized values were further normalized to the value in cells infected with shControl and treated with DMSO. The data from two replicates (n=2) were used to generate the figure shown in this panel. B) Western blot bands of p-AKT-S473 (or p-ERK1/2), in LNCaP (left panel) and BT474 (right panel) cells transfected with empty vector (EV) or expression vector for small FOXO1 phosphomimicking peptide HA-FOXO1-IQBP(SE) and treated with vehicle (DMSO) or paclitaxel as shown in FIG. 15B and the repeated experiment (replication 2), were quantified and normalized to the quantified value of total AKT (or total ERK2). The normalized values were further normalized to the value in cells transfected with EV and treated with DMSO. The data from two replicates (n=2) were used to generate the figure shown in this panel.

FIG. 18 shows that AKT-phosphorylated FOXO1 inhibits PKM2 nuclear localization and the Warburg effect. A) Immunofluorescence of PKM2 in LNCaP cells 72 hours after infected with lentivirus expressing indicated shRNAs. B) Western blot analysis of whole cell lysate, cytosolic and nuclear extracts of LNCaP cells 72 hours after infected with lentivirus expressing indicated shRNAs. C) RT-qPCR analysis of expression of nuclear PKM2-regulated genes GLUT1, LDHA and PKM2 in DU145 cells 48 hours after transfected with indicated plasmids. *P<0.05 comparing the FOXO1-537 group with other two groups. D) Measurement of glucose consumption and L-Lactate production in the spent medium of DU145 cells 48 hours after transfected with indicated FOXO1 plasmids. *P<0.05. E) RT-qPCR analysis of expression of nuclear PKM2-regulated genes, GLUT1, LDHA and PKM2 in LNCaP cells 72 hours after infected with lentivirus expressing indicated shRNAs. *P<0.05. F) Measurement of glucose consumption and L-Lactate production in the spent medium of LNCaP cells 72 hours after infected with lentivirus expressing indicated shRNAs. *P<0.05.

Figure 19A:
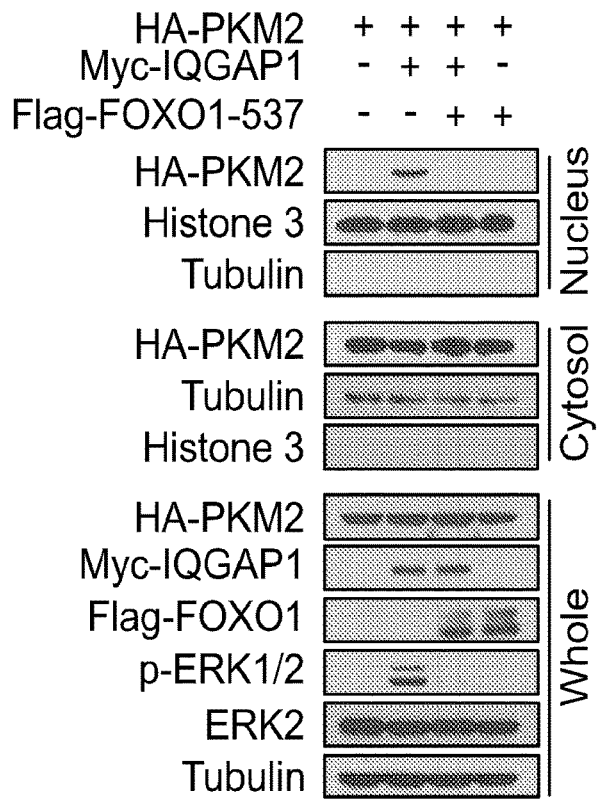

FIG. 19 shows that cytoplasmic FOXO1 inhibits IQGAP1-facilitated ERK activation and PKM2 nuclear localization. A) Western blot analysis of whole cell lysate, cytosolic or nuclear extracts of C4-2 cells 24 hours after transfected with indicated plasmids. B) Western blot analysis of whole cell lysate, cytosolic or nuclear extracts of DU145 cells 24 hours after transfected with indicated plasmids and/or 72 hours after infected with lentivirus-based shRNAs.

FIG. 20 shows that cytoplasmic FOXO1 inhibits IQGAP1-facilitated PKM2 activation and Warburg effect. A) RT-qPCR analysis of expression of nuclear PKM2-regulated downstream genes GLUT1, LDHA and PKM2 mRNAs in C4-2 cells 24 hours after transfected with indicated plasmids. B) Measurement of glucose consumption and L-Lactate concentration in the spent medium of C4-2 cells 24 hours after transfected with indicated plasmids using Glucose (GO) Assay and L-Lactate Assay Kits. C) Western blot analysis of DU145 cells 72 hours after infected with lentivirus expressing PKM2 shRNAs. D) RT-qPCR analysis of expression of nuclear PKM2-regulated downstream genes GLUT1, LDHA and PKM2 mRNAs in DU145 cells 72 hours after infected with lentivirus expressing indicated shRNAs. E) Measurement of glucose consumption and L-Lactate concentration in the spent medium of DU145 cells 72 hours after infected with lentivirus expressing indicated shRNAs using Glucose (GO) Assay and L-Lactate Assay Kits.

DETAILED DESCRIPTION

This document provides methods and materials for treating cancer in a mammal (e.g., human). For example, this document provides methods and materials for using a phosphorylation-mimicking peptide (e.g., a phosphorylation-mimicking FOXO1-derived peptide) to treat chemotherapeutic resistant cancer. In some cases, a phosphorylation-mimicking FOXO1-derived peptide can be used to reduce the number of cancer cells in a mammal (e.g., human). In some cases, a phosphorylation-mimicking FOXO1-derived peptide can be used to decrease expression of GLUT1, LDHA, and/or PKM2. In some cases, a phosphorylation-mimicking FOXO1-derived peptide can be used to decrease or inhibit glucose consumption and/or lactate production.

A phosphorylation-mimicking peptide provided herein can be derived from a forkhead box (FOX) peptide. The FOX peptide can be any class of FOX peptide (e.g., class A, class B, class D, class, D, class E, class F, class class H, class I, class J, class K, class, L, class M, class N, class O, class P, class Q, or class R). In some cases, the FOX peptide can be a class O FOX (FOXO) peptide. Examples of FOXO peptides include, without limitation, FOXO1, FOXO3, FOXO4, and FOXO6. In some cases, a phosphorylation-mimicking peptide provided herein can be derived from a FOXO1 peptide. A phosphorylation-mimicking peptide provided herein can be a fragment of a FOXO1 peptide containing a phosphorylation site (e.g., threonine 24, serine 256, or serine 319 of a human FOXO1). Examples of human FOXO1 peptides include, without limitation, amino acid sequence set forth in National Center for Biotechnology Information (NCBI) Accession Nos: AAH21981 (see, e.g., Version AAH21981.1; GI:18314375), AAH70065 (see, e.g., Version AAH70065.3; GI:145207306), and NP 002006 (see, e.g., Version NP_002006.2; GI:9257222). A phosphorylation-mimicking peptide provided herein can be a fragment of FOXO1 that binds to IQGAP1 and contains amino acid residue 319 of a human FOXO1. An exemplary fragment of FOXO1 that binds to IQGAP1 and contains amino acid residue 319 can include the amino acid sequence 304-NDDFDNWSTFRPRTSSNASTISGRLSPIMT-333 (S319 in bold; SEQ ID NO:1). A phosphorylation-mimicking peptide provided herein (e.g., a phosphorylation-mimicking FOXO1-derived peptide) can be engineered to modify a phosphorylation site in FOXO1 (e.g., modify serine 319 of FOXO1 by substitution with a glutamic acid (E) or aspartic acid (D)) to mimic the phosphorylated state. For example, a phosphorylation-mimicking peptide provided herein can have a glutamic acid at position 319 (S319E). For example, a phosphorylation-mimicking peptide provided herein can have an aspartic acid at position 319 (S319D). A phosphorylation-mimicking peptide provided herein can be a fragment of FOXO1 that is about 20 amino acids to about 250 amino acids in length (e.g., about 22 to about 200, about 25 to about 150, about 28 to about 85, or about 30 to about 50 amino acids in length) and contains amino acid residue 319 of FOXO1. In some cases, a phosphorylation-mimicking peptide provided herein can be have at least 75 percent sequence identity (e.g., at least 80%, at least 82%, at least 85%, at least 88%, at least 90%, at least 93%, at least 95%, at least 97% or at least 99% sequence identity) to a FOXO1 peptide or a fragment of FOXO1 contains amino acid residue 319 of FOXO1 provided herein. In some cases, a phosphorylation-mimicking peptide provided herein can include a 30 amino acid fragment of a human FOXO1 protein (e.g., residues 304 to 333) having a glutamic acid at position 319: NDDFDNWSTFRPRTSENASTISGRL-SPIMT (SEQ ID NO:2). In some cases, a phosphorylation-mimicking peptide provided herein can include a 30 amino acid fragment of a human FOXO1 protein (e.g., residues 304 to 333) having an aspartic acid at position 319: NDDFDNW-STFRPRTSDNASTISGRLSPIMT (SEQ ID NO:3).

A phosphorylation-mimicking peptide provided herein also can include additional peptide sequences including, for example, cell-penetrating peptides (CPPs; such as 8 arginine residues (e.g., 8 D-arginine residues)), a nuclear exportation signal (NES), a nuclear localization signal (NLS), reporter sequences (e.g., fluorescent peptides, bioluminescent peptides, or selectable markers), and epitope tags (e.g., hemagglutinin (HA), FLAG®, maltose-binding protein (MBP), cellulose-binding domain (CBD), or glutathione S-transferase (GST)). In some cases, a phosphorylation-mimicking FOXO1-derived peptide can include the amino acid sequence RRRRRRRRYPYDVPDYANDDFDNWSTFR-PRTSENASTISGRLSPIMT (SEQ ID NO:4), where residues 1-8 are 8 D-arginine residues, residues 9-17 are an HA tag, and residues 18 to 47 are a fragment of a human FOXO1 protein having a glutamic acid at position 319. In some cases, a phosphorylation-mimicking FOXO1-derived peptide can include the amino acid sequence RRRRRRRRY-PYDVPDYANDDFDNWSTFRPRTSDNASTISGRL-SPIMT (SEQ ID NO:5), where residues 1-8 are 8 D-arginine residues, residues 9-17 are an HA tag, and residues 18 to 47 are a fragment of a human FOXO1 protein having an aspartic acid at position 319.

Any method can be used to obtain a phosphorylation-mimicking peptide provided herein. In some cases, peptide synthesis methods can be used to make a phosphorylation-mimicking peptide provided herein. Examples of methods of peptide synthesis include, without limitation, liquid-phase peptide synthesis and solid-phase peptide synthesis. In some cases, protein biosynthesis methods can be used to make a phosphorylation-mimicking peptide provided herein. Methods of protein biosynthesis include, without limitation, transcription, and/or translation of nucleic acids encoding a phosphorylation-mimicking peptide provided herein. Examples of nucleic acids encoding a human FOXO1 peptide include, without limitation, nucleic acids sequence set forth in NCBI Accession Nos: BCO21981 (see, e.g., Version BCO21981.2; GI:33869892), BCO70065 (see, e.g., Version BCO70065.1; GI:4712331), and NM_002015 (see, e.g., Version NM_002015.3; GI:133930787). This document also provides nucleic acids encoding a phosphorylation-mimicking peptide provided herein as well as constructs for expressing nucleic acids encoding a phosphorylation-mimicking peptide provided herein.

In some cases, a phosphorylation-mimicking peptide provided herein can be formulated as a pharmaceutical composition. For example, a composition containing a phosphorylation-mimicking peptide provided herein can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers for oral administration. An acceptable aqueous vehicle can be, for example, any liquid solution that is capable of dissolving a phosphorylation-mimicking peptide provided herein and is not toxic to the particular individual receiving the composition. Examples of acceptable aqueous vehicles include, without limitation, saline, water, and acetic acid. Typically, acceptable aqueous vehicles are sterile. An acceptable solid vehicle can be formulated such that a composition containing a phosphorylation-mimicking peptide provided herein is suitable for oral administration. The dose supplied by each capsule or tablet can vary since an effective amount can be reached by administrating either one or multiple capsules or tablets. Any appropriate pharmaceutically acceptable material such as gelatin and cellulose derivatives can be used as an acceptable solid vehicle. In addition, an acceptable solid vehicle can be a solid carrier including, without limitation, starch, sugar, or bentonite. Further, a tablet or pill formulation of a composition containing a phosphorylation-mimicking peptide can follow conventional procedures that employ solid carriers, lubricants, and the like. In some cases, a formulation of a composition containing a phosphorylation-mimicking peptide can be formulated for controlled release.

Any appropriate method can be used to formulate a pharmaceutical composition provided herein (e.g., a pharmaceutical composition containing a phosphorylation-mimicking peptide provided herein). For example, common formulation mixing and preparation techniques can be used to make a composition having the components described herein. In addition, the compositions provided herein can be in any appropriate form. For example, a composition provided herein can be in the form of a solid, liquid, and/or aerosol including, without limitation, powders, crystalline substances, gels, pastes, ointments, salves, creams, solutions, suspensions, partial liquids, sprays, nebulae, mists, atomized vapors, tinctures, pills, capsules, tablets, and gelcaps. In some embodiments, compositions containing a phosphorylation-mimicking peptide provided herein can be prepared for oral administration by mixing the components with one or more of the following: a filler, a binder, a disintegrator, a lubricant, and a coloring agent. Lactose, corn starch, sucrose, glucose, sorbitol, crystalline cellulose, silicon dioxide, or the like can be used as the filler. Polyvinyl alcohol, polyvinyl ether, ethyl cellulose, methyl cellulose, acacia, tragacanth, gelatin, shellac, hydroxypropyl cellulose, hydroxypropylmethyl cellulose, calcium citrate, dextrin, or pectin can be used as the binder. Magnesium stearate, talc, polyethylene glycol, silica, or hardened plant oil can be used as the lubricant. A pharmaceutically acceptable coloring agent can be used as the coloring agent. Cocoa powder, mentha water, aromatic acid, mentha oil, borneol, or powdered cinnamon bark also can be added. In some cases, compositions containing a phosphorylation-mimicking peptide provided herein can be prepared for injection by mixing the components with one or more of the following: a pH adjusting agent, a buffer, a stabilizer, and a solubilizing agent.

This document also provides methods and materials for using a phosphorylation-mimicking peptide provided herein. For example, a phosphorylation-mimicking peptide provided herein (e.g., a phosphorylation-mimicking FOXO1-derived peptide) can be administered to any appropriate mammal to treat the mammal for a cancer (e.g., a chemotherapeutic resistant cancer), to decrease expression of decrease expression of GLUT1, LDHA, and/or PKM2 in cancer cells, and/or to decrease or inhibit glucose consumption and/or lactate production in cancer cells.

In some cases, a phosphorylation-mimicking peptide provided herein can be used to treat cancer in a mammal (e.g., a human). Methods for treating a mammal having cancer (e.g., chemotherapeutic resistant cancer) can include administering to the mammal a phosphorylation-mimicking peptide provided herein. A phosphorylation-mimicking peptide provided herein can be administered to any mammal (e.g., human, rat, mouse, dog, cat, horse, cow, goat, pig, or monkey). In addition, any route of administration (e.g., oral or parenteral administration) can be used to administer a phosphorylation-mimicking peptide provided herein to a mammal. For example, a phosphorylation-mimicking peptide provided herein can be administered orally or parenterally (e.g., a subcutaneous, intramuscular, intraorbital, intracapsular, intraspinal, intrasternal, or intravenous injection).

Cancer can occur in many tissues within the body. Examples of cancers that can be treated using a phosphorylation-mimicking peptide provided herein include, without limitation, prostate, breast, pancreatic, nasopharyngeal, ovarian, colon, colorectal, blood, lymph, lung, liver, brain, skin, and bone cancer. In some embodiments, the cancer treated as described herein can be a chemotherapy resistant cancer. Examples of chemotherapeutic drugs include, without limitation, alkylating agents (e.g., nitrogen mustards such as mechlorethamine, cyclophosphamide, melphalan, chlorambucil, ifosfamide and busulfan; nitrosoureas such as N-Nitroso-N-methylurea (MNU), carmustine (BCNU), lomustine (CCNU) and semustine (MeCCNU), fotemustine and streptozotocin; tetrazines such as dacarbazine, mitozolomide and temozolomide; aziridines such as thiotepa, mytomycin and diaziquone (AZQ); cisplatins and derivatives such as cisplatin, carboplatin and oxaliplatin; and non-classical alkylating agents such as procarbazine and hexamethylmelamine), anti-metabolites (e.g., anti-folates such as methotrexate and pemetrexed; fluoropyrimidines such as fluorouracil and capecitabine; deoxynucleoside analogues such as cytarabine, gemcitabine, decitabine, Vidaza, fludarabine, nelarabine, cladribine, clofarabine and pentostatin; and thiopurines such as thioguanine and mercaptopurine), anti-microtubule agents (e.g., *vinca* alkaloids such as vincristine, vinblastine, vinorelbine, vindesine, and vinflunine; and taxanes such as paclitaxel, docetaxel, and cabazitaxel; podophyllotoxin; etoposide; and teniposide), topoisomerase inhibitors (e.g., topoisomerase I inhibitors such as irinotecan and topotecan; and topoisomerase II inhibitors such as etoposide, doxorubicin, mitoxantrone, teniposide, novobiocin, merbarone, and aclarubicin), and cytotoxic antibiotics (e.g., anthracyclines such as doxorubicin, daunorubicin, epirubicin, idarubicin, pirarubicin, aclarubicin, and mitoxantrone; bleomycins; mitomycin C; mitoxantrone; and actinomycin). For example, a phosphorylation-mimicking FOXO1-derived peptide can be used to treat a taxane resistant prostate cancer.

Methods for treating a mammal having cancer using a phosphorylation-mimicking peptide provided herein can be effective to reduce the number of cancer cells in the mammal. In some cases, treating a mammal having cancer using a phosphorylation-mimicking peptide provided herein can be effective to eliminate the cancer cells in the mammal.

Methods for treating a mammal having cancer can include identifying the mammal as having cancer. Examples of methods for identifying the mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, the mammal can be administered or instructed to self-administer a phosphorylation-mimicking peptide provided herein.

Methods for treating a mammal having cancer also can include one or more additional cancer treatments such as surgery, chemotherapy, radiation therapy, immunotherapy, targeted therapy, and/or hormone therapy. In some cases, a phosphorylation-mimicking peptide provided herein can be formulated together with one or more additional cancer treatments (e.g., a chemotherapeutic such as paclitaxel or docetaxel) to form a single composition. In some cases, one or more additional cancer treatments can be provided to a mammal in a separate composition; one containing a phosphorylation-mimicking peptide provided herein, and one containing, for example, paclitaxel and/or docetaxel. In cases, where a phosphorylation-mimicking peptide provided herein and one or more additional cancer treatments are provided separately, the administration of a phosphorylation-mimicking peptide provided herein can be in any order relative to the administration of one or more additional cancer treatments. For example, a phosphorylation-mimicking peptide provided herein can be administered to a mammal prior to, concurrent with, or following administration of one or more additional cancer treatments to the mammal. In cases where a phosphorylation-mimicking peptide provided herein is administered to a mammal prior to administration of a chemotherapeutic (e.g., paclitaxel and/or docetaxel) to the mammal, the phosphorylation-mimicking peptide can be administered prior to development of chemotherapeutic resistance.

In some cases, a phosphorylation-mimicking peptide provided herein can be used to decrease expression of GLUT1, LDHA, and/or PKM2. Methods for decreasing expression of GLUT1, LDHA, and/or PKM2 in cells can include contacting the cells with a phosphorylation-mimicking peptide provided herein. Cells can be in vitro or in vivo. Cells can be from any appropriate sources (e.g., mammalian cells such as human cells). The cells can be cancer (e.g., prostate, breast, pancreatic, nasopharyngeal, ovarian, colon, colorectal, blood, lymph, lung, liver, brain, skin, and bone cancer cells). A phosphorylation-mimicking peptide provided herein can be contacted with the cells by any appropriate method. A phosphorylation-mimicking peptide provided herein can be contacted with cells in an amount and at a frequency such that expression of GLUT1, LDHA, and/or PKM2 is decreased. For example, a phosphorylation-mimicking peptide provided herein can be used to decrease expression of GLUT1, LDHA, and/or PKM2 by at least 1.2 fold (e.g., at least 1.3 fold, at least 1.4 fold, at least 1.5 fold, at least 1.6 fold, at least 1.7 fold, at least 1.8 fold, at least 1.9 fold, at least 2.0 fold, at least 2.1 fold, at least 2.2 fold, at least 2.3 fold, at least 2.4 fold, or at least 2.5 fold). For example, a phosphorylation-mimicking peptide provided herein can be used to decrease expression of GLUT1, LDHA, and/or PKM2 by at least 20 percent (e.g., at least 30 percent, at least 40 percent, at least 50 percent, at least 60 percent, at least 70 percent, at least 80 percent, at least 90 percent, at least 100 percent, at least 110 percent, at least 120 percent, at least 130 percent, at least 140 percent, at least 150 percent, at least 160 percent, at least 170 percent, at least 180 percent, at least 190 percent, or at least 200 percent).

In humans, a phosphorylation-mimicking peptide provided herein can be used to decrease expression of a human GLUT1 polypeptide, a human LDHA polypeptide, a human PKM2 polypeptide, or a combination thereof. In some cases, a human GLUT1 polypeptide can have an amino acid sequence set forth in, for example, NCBI Accession No: NP_006507 (see, e.g., Version NP_006507.2; GI:166795299). In some cases, a human LDHA polypeptide can have an amino acid sequence set forth in, for example, NCBI Accession Nos: AAH67223 (see, e.g., Version AAH67223.1; GI:45501322), NP_005557 (see, e.g., Version NP_005557.1; GI:5031857), NP_001128711 (see, e.g., Version NP_001128711.1; GI:207028494), NP_001158886 (see, e.g., Version NP_001158886.1; GI:260099723), NP_001158887 (see, e.g., Version NP_001158887.1; GI:260099725), NP_001158888 (see, e.g., Version NP_001158888.1; GI:260099727), CAG33056 (see, e.g., Version CAG33056.1; GI:48145667), and AIC54695 (see, e.g., Version AIC54695.1; GI:649119719). In some cases, a human PKM2 polypeptide can have an amino acid sequence set forth in, for example, NCBI Accession No: NP_002645 (see, e.g., Version NP_002645.3; GI:33286418).

In some cases, a phosphorylation-mimicking peptide provided herein can be used to inhibit glucose consumption and/or lactate production.

Any appropriate dose of a phosphorylation-mimicking peptide provided herein can be administered to a mammal. For example, an appropriate dose of a phosphorylation-mimicking peptide provided herein can be effective to reduce the number of cancer cells in a mammal (e.g., human), to decrease expression of GLUT1, LDHA, and/or PKM2, and/or to decrease or inhibit glucose consumption and/or lactate production upon administration to a mammal without producing significant toxicity to the mammal. Various factors can influence the actual amount used for a particular application. For example, the frequency of administration, duration of treatment, combination of other agents, site of administration, stage of disease (if present), and the anatomical configuration of the treated area may require an increase or decrease in the actual amount administered.

The frequency of administration of a phosphorylation-mimicking peptide provided herein can be any frequency. For example, the frequency of administration can be from about four times a day to about once a month, or more specifically, from about twice a day to about once a week. In addition, the frequency of administration can remain constant or can be variable during the duration of treatment. As with the amount administered, various factors can influence the actual frequency of administration used for a particular application. For example, the amount (dose), duration of treatment, combination of agents, site of administration, stage of disease (if present), and the anatomical configuration of the treated area may require an increase or decrease in administration frequency.

The duration of administration of a phosphorylation-mimicking peptide provided herein can be any duration. For example, a duration of administration of compositions provided herein can be longer than a week, month, three months, six months, nine months, a year, two years, or three years. In some cases, an effective duration can be any duration that reduces the number of cancer cells in a mammal (e.g., human), decreases expression of GLUT1, LDHA, and/or PKM2, or decreases or inhibits glucose consumption and/or lactate production upon administration to a mammal without producing significant toxicity to the mammal. Such an effective duration can vary from several days to several weeks, months, or years. In general, an effective duration for the treatment of an acute disease can range in duration from several days to several months. Once administration of a phosphorylation-mimicking peptide provided herein is stopped, however, symptoms may return. In such cases, an effective duration for the prevention of certain conditions can last for as long as the individual is alive. Multiple factors can influence the actual duration used for a particular treatment or prevention regimen. For example, an effective duration can vary with the frequency of administration, the amount administered, combination of multiple agents, site of administration, state of disease (if present), and anatomical configuration of the treated area.

The invention will be further described in the following examples, which do not limit the scope of the invention described in the claims.

EXAMPLES

Example 1: Experimental Procedures

Plasmids, Antibodies and Reagents

The mammalian expression vectors Flag-FOXO1, Flag-FOXO1-T24A, S256A, S319A, A3, Flag-FOXO1-537 (in which histidine 215, a key residue for DNA binding is mutated to arginine and the transactivation domain (amino acids 538-655) is deleted), FOXO1-537-A3, NLSm, hemagglutinin (HA)-tagged CA-AKT, HA-FOXO3, HA-FOXO4 were described elsewhere (see, e.g., Gan et al, 2009 Cancer Res 69:8386-8394; Gan et al, 2009 Cell Death Differ. 16:1408-1417; Huang et al, 2006 Science 314:294-297; Huang et al., 2005 Proc. Natl. Acad. Sci. USA 102:1649-54; Liu et al, 2008 Cancer Res 68:10290-10299; Zhang et al, 2011 Cancer Res 71:3257-3267). A HA-tagged small (30 amino acids) FOXO1-derived IQGAP1-binding peptide, 304-NDDFDNWSTFRPRTSSNASTISGRLSPIMT-333 (S319 in bold; SEQ ID NO:1), was cloned into the pCMV vector (HA-FOXO1-IQBP-5319) and further mutated to glutamic acid (E) or aspartic acid (D) to generate two phospho-mimicking mutants HA-FOXO1-IQBP-5319E and HA-FOXO1-IQBP-5319D using site-specific mutagenesis (Agilent). Lenti-virus based HA-FOXO1 IQBP-5319E (or called HA-FOXO1 IQBP(SE)) was cloned into pTsin vector. A Flag-tagged FOXO1 IQBP(SE) was generated by sub-cloning phospho-mimicking FOXO1 IQBP(SE) peptide into SFB vector. Flag-FOXO1-537-S319A, HA-FOXO3-S315A, and HA-FOXO4-S262A were generated by site-specific mutagenesis (Agilent). Using KOD-Plus Mutagenesis Kit (Toyobo) Flag-FOXO1-NESm was generated as reported elsewhere (Matsuzaki et al, 2003 $Proc$ $Natl$ $Acad$ $Sci$ $USA$ 100:11285-11290) by mutating the FOXO1 nuclear export signal motif <u>M</u>ENLL<u>D</u>NLNL (SEQ ID NO:6) to <u>AE</u> <u>N</u>ALDNANA (SEQ ID NO:7). shFOXO1 #1-resistant Flag-tagged FOXO1 (FOXO1$^{S1R}$) and shFOXO1 #2-resistant Flag-tagged FOXO1 (Flag-FOXO1$^{S2R}$) were generated using KOD-Plus Mutagenesis Kit (Toyobo). Plasmids for HA-tagged AKT kinase dead mutant (K179M) (termed AKT-DN) and pcDNA3-Myc-IQGAP1 were purchased from Addgene. A Flag-tagged IQGAP1 was generated by sub-cloning Flag-IQGAP1 into pcDNA3.1 vector. Bacterial expression vectors for various GST-tagged FOXO1 recombinant proteins were generated by sub-cloning the following regions from full-length FOXO1 (amino acids 1-655) into the pGEX-4T-1 vector: FOXO1-1 (amino acids 1-167), FOXO1-2 (amino acids 149-267), FOXO1-3 (amino acids 211-419), FOXO1-4 (amino acids 354-503), FOXO1-5 (amino acids 488-655). GST-FOXO1-3 (211-419) S319A was generated by KOD-Plus Mutagenesis Kit (Toyobo). GST-tagged IQGAP1 recombinant protein constructs were generated by sub-cloning the full-length IQGAP1 (amino acids 1-1657) or the following regions of IQGAP1 into pGEX-4T-1 vectors: IQGAP1-P1 (amino acids 1-185), IQGAP1-P2 (amino acids 166-670), IQGAP1-P3 (amino acids 671-730), IQGAP1-P4 (amino acids 731-860), IQGAP1-P5 (amino acids 861-1250), IQGAP1-P6 (amino acids 1251-1657).

Antibodies used were: anti-IQGAP1, anti-ERK2, anti-Myc tag, anti-p27 (Santa Cruz Biotechnology); anti-FOXO1 (Bethyl); anti-p-ERK1/2, anti-AKT, anti-p473-AKT, anti-p308-AKT, anti-p319-FOXO1, anti-p256-FOXO1 (Cell Signaling Technology); anti-Flag (Sigma-Aldrich) and anti-HA (Covance). The chemicals purchased: trypsin (Thermo Fisher Scientific), cycloheximide (CHX) and paclitaxel (Sigma-Aldrich), MK2206 (Selleckchem), NVP-BEZ235 (LC-Laboratories) and docetaxel (Active Biochem).

Cell Lines, Cell Culture, and Transfection

The prostate cancer cell lines DU145 and LNCaP and human embryonic kidney cell line 293T were purchased from ATCC. DU145 and LNCaP cells were cultured in RPMI1640 medium supplemented with 10% fetal bovine serum (FBS). 293T cells were maintained in Dulbecco modified Eagle medium (Thermo Fisher Scientific) supplemented with 10% FBS. The C4-2 cell line was purchased from UroCorporation and grown in RPMI 1640 supplemented with 10% FBS. Breast cancer cell lines MDA-MB-468 and BT474, and pancreatic cancer cell lines PANC-1 and MIA-PaCa-2 were obtained. MDA-MB-468, PANC-1, and MIA-PaCa-2 cell lines were cultured in DMEM medium supplemented with 10% FBS. BT474 was cultured in RPMI 1640 medium supplemented with 10% FBS. Cells were cultured at 37° C. supplied with 5% $CO_2$. Transfections were performed by electroporation with an Electro Square Porator ECM 830 (BTX) (Chen et al, 2010 $Nat$ $Cell$ $Biol$ 12:1108-1114) or with Lipofectamine 2000 (Thermo Fisher Scientific). Approximately 75% to 95% transfection efficiencies were routinely achieved.

Tandem Affinity Purification of Proteins 293T cells were transfected with SFB backbone vector or SFB-tagged FOXO1. 24 hours after transfection, cells were lysed by NETN buffer (20 mM Tris-HCl, pH8.0, 100 mM NaCl, 1 mM EDTA, 0.5% Nonidet P-40) with 50 mM β-glycerophosphate, 10 mM NaF, and 1 μg/mL pepstatin-A at 4° C. for 3 hours. The supernatants were incubated with streptavidin sepharose beads (GE) at 4° C. overnight. The beads were washed with NETN buffer for three times and then eluted by 2 mM biotin (Sigma) for 1 hour at 4° C. twice. The elution products were incubated with S-protein agarose beads (Novagen) overnight at 4° C. and after three times wash the products bound to S-protein agarose beads were subjected to SDS-PAGE and visualized by silver staining or Code-blue staining.

Protein Sequence Analysis by LC-MS/MS

The identities of eluted proteins from tandem affinity purification were revealed by mass spectrometry performed by the Taplin Biological Mass Spectrometry Facility at Harvard. Briefly, excised gel bands were cut into approximately 1 mm$^3$ pieces. Gel pieces were then subjected to a modified in-gel trypsin digestion procedure (Shevchenko et al, 1996 $Anal$ $Chem$ 68: 850-858). Gel pieces were washed and dehydrated with acetonitrile for 10 minutes followed by removal of acetonitrile. Pieces were then completely dried in a speed-vac. Rehydration of the gel pieces was with 50 mM ammonium bicarbonate solution containing 12.5 ng/μl modified sequencing-grade trypsin (Promega) at 4° C. After 45 minutes, the excess trypsin solution was removed and replaced with 50 mM ammonium bicarbonate solution to just cover the gel pieces. Samples were then placed in a 37° C. room overnight. Peptides were later extracted by removing the ammonium bicarbonate solution, followed by one wash with a solution containing 50% acetonitrile and 1% formic acid. The extracts were then dried in a speed-vac (~1 hour). The samples were then stored at 4° C. until analysis.

On the day of analysis, the samples were reconstituted in 5-10 μl of HPLC solvent A (2.5% acetonitrile, 0.1% formic acid). A nano-scale reverse-phase HPLC capillary column was created by packing 5 μm C18 spherical silica beads into a fused silica capillary (125 μm inner diameter×~20 cm length) with a flame-drawn tip (Peng & Gygi, 2001 $J$ $Mass$ $Spectrom$ 36: 1083-1091). After equilibrating the column each sample was loaded via a Famos auto sampler (LC Packings) onto the column. A gradient was formed and peptides were eluted with increasing concentrations of solvent B (97.5% acetonitrile, 0.1% formic acid).

As peptides eluted they were subjected to electrospray ionization and then entered into an LTQ Velos ion-trap mass spectrometer (Thermo Fisher Scientific). Peptides were detected, isolated, and fragmented to produce a tandem mass spectrum of specific fragment ions for each peptide. Peptide sequences (and hence protein identity) were determined by matching protein databases with the acquired fragmentation pattern by the software program, Sequest (Thermo Fisher Scientific) (Eng et al, 1994 $J$ $Am$ $Soc$ $Mass$ $Spectrom$ 5: 976-989). Spectral matches were manually examined and multiple identified peptides per protein were required.

Co-Immunoprecipitation (Co-IP) and Western Blotting

Immunoprecipitations were performed as described previously (Huang et al, 2006 $Science$ 314:294-297; Wang et al, 2013 $EMBO$ $J$ 32:1584-1597). Cells were harvested and lysed in cell lysis buffer (50 mM Tris-HCl, pH 7.5, 150 mM NaCl, 1% Nonidet P-40, 0.5% sodium deoxycholate, and 1% protease inhibitor cocktails, Sigma-Aldrich). Cell lysates were centrifuged and the supernatant was then incubated with indicated antibodies and protein-G beads (Thermo Fisher Scientific) at 4° C. overnight. The beads were washed more than five times using cell lysis buffer, and the precipitated proteins were used for further analysis. For Western blotting, protein samples were prepared in modified RIPA buffer (1×PBS, 1% NP-40, 0.1% SDS, and 1% protease inhibitor cocktails). Equal amounts of protein (50~100 μg) from cell lysate were denatured in sample buffer (Thermo Fisher Scientific). Proteins were separated by SDS-polyacrylamide gel electrophoresis, and then were transferred to nitrocellulose membranes (Bio-Rad). After the membranes were immunoblotted with specific primary antibodies and horseradish peroxidase-conjugated secondary antibodies, they were visualized by SuperSignal West Pico Stable Peroxide Solution (Thermo Fisher Scientific).

GST Pull-Down Assay Using Cell Lysate

Cells were lysed with cell lysis/protein binding buffer (20 mM Tris-HCl (pH 7.5), 150 mM NaCl, 0.1% Nonidet P40, 1 mM DTT (dithiothreitol), 10% glycerol, 1 mM EDTA, 2.5 mM MgCl2 and 1 μg/ml leupeptin) for 30 min at 4° C. GST fusion proteins and glutathione-sepharose beads (GE Healthcare Life Science) were incubated with cell lysates for 4 hours. The beads were then washed four times with binding buffer and resuspended in sample buffer. The bound proteins were subjected to SDS/PAGE.

In Vitro Transcription and Translation of IQGAP1 Proteins

Plasmid DNA (Flag-IQGAP1) was added to the TNT® T7 Quick Master Mix, and then 1 μl methionine (1 mM) was added, by following the manufacturer's instruction of TNT® Quick Coupled Transcription/Translation Systems (Promega). The in vitro transcribed and translated proteins were subjected to GST pull-down assay.

In Vitro Kinase Assay

C4-2 cells were transfected with expression vector for HA-tagged constitutively active AKT (HA-AKT-CA). 24 hours after transfection, cells were harvested and lysed in cell lysis buffer (50 mM Tris-HCl, pH 7.5, 150 mM NaCl, 1% Nonidet P-40, 0.5% sodium deoxycholate and 1% protease inhibitor cocktails, Sigma-Aldrich).

Cell lysates were centrifuged and the supernatant was incubated with non-specific IgG or anti-HA antibody and protein-G beads (Thermo Fisher Scientific) at 4° C. overnight. The beads were washed five times with cell lysis buffer and then washed with 1× kinase buffer. Immunoprecipitated IgG or HA-AKT were incubated with purified GST or GST-FOXO1 recombinant proteins (GST-FOXO1-3 (211-419) or GST-FOXO1-3 S319A) and ATP in kinase buffer by following the manufacturer's instruction of AKT Kinase Assay Kit (Nonradioactive) (Cell Signaling Technology). The supernatant containing phosphorylated protein were subjected to GST pull down.

GST Pull-Down Assay Using In Vitro Translated Protein

In vitro transcribed and translated Flag-tagged IQGAP1 proteins were incubated with GST or GST-FOXO1 recombinant proteins undergone AKT kinase assay in protein binding buffer (20 mM Tris-HCl (pH 7.5), 150 mM NaCl, 0.1% Nonidet P40, 1 mM DTT (dithiothreitol), 10% glycerol, 1 mM EDTA, 2.5 mM MgCl2 and 1 μg/ml leupeptin). Glutathione-Sepharose beads (GE Healthcare Life Science) were added and further incubated for 4 hours. The beads were then washed four times with binding buffer and resuspended in sample buffer. The bound proteins were subjected to SDS/PAGE.

RNA Interference

Nonspecific control small interfering RNA (siRNA) and siRNAs for human IQGAP1, FOXO1, and FOXO3 were purchased from Thermo Scientific Dharmacon. siRNA transfection of cells was performed following the manufacturer's instruction. Lentivirus-based control and gene-specific shRNAs were purchased from Sigma-Aldrich. siRNA and shRNA sequence information is provided in Table 1.

TABLE 1

Sequences for shRNAs

| Gene | Sequence | SEQ ID NO: |
|---|---|---|
| sh IQGAP1-1 | 5'-CCGGGCCCACATTGTGCCTTTATTTCTCGAGAAATAAAGGCACAATGTGGGCTTTTTG-3' | 8 |
| sh IQGAP1-2 | 5'-CCGGCCTCAGATTCAAGACCTATATCTCGAGATATAGGTCTTGAATCTGAGGTTTTTG-3' | 9 |
| sh FOXO1-1 | 5'-CCGGGCCGGAGTTTAGCCAGTCCAACTCGAGTTGGACTGGCTAAACTCCGGCTTTTTG-3' | 10 |
| sh FOXO1-2 | 5'-CCGGATCTACGAGTGGATGGTCAACTCGAGTTGACCATCCACTCGTAGATCTTTTTG-3' | 11 |
| sh FOXO3-1 | 5'-CCGGCAGACCCTCAAACTGACACAACTCGAGTTGTGTCAGTTTGAGGGTCTGTTTTTG-3' | 12 |
| sh FOXO3-4 | 5'-CCGGGTCACTGCATAGTCGATTCATCTCGAGATGAATCGACTATGCAGTGACTTTTTG-3' | 13 |
| sh PKM2-B8 | 5'-CCGGGCCCGAGGCTTCTTCAAGAAGCTCGAGCTTCTTGAAGAAGCCTCGGGCTTTTTG-3' | 14 |
| sh PKM2-B9 | 5'-CCGGGTTCGGAGGTTTGATGAAATCCTCGAGGATTTCATCAAACCTCCGAACTTTTTG-3' | 15 |
| sh PKM2-C2 | 5'-CCGGCTTTCCTGTGTGTACTCTGTCCTCGAGGACAGAGTACACACAGGAAAGTTTTTG-3' | 16 |

MTS Cell Viability Assay

Cell growth was measured by absorbance using the MTS assay according to manufacturer's instructions (Promega). Cells were plated in 96-well plates at a density of 1,000 cells per well. At the indicated time points, 20 μl of CellTiter 96R AQueous One Solution reagent (Promega) was added to cells; after incubating for 60 minutes at 37° C., cell growth was measured in a microplate reader at 490 nm.

Detection of Apoptosis Using Annexin V Assay and Flow Cytometry

Cells were stained with PE Annexin V and 7-aminoactinomycin following the manufacturer's instruction of PE Annexin V Apoptosis Detection Kit I (BD Biosciences). A minimum of 10,000 stained cells were immediately assayed on a flow cytometer. Data was analyzed with FlowJo analysis software.

Immunofluorescent Cytochemistry

Immunofluorescent cytochemistry was performed as previously described (Huang et al, 2006 Science 314:294-297). Briefly, cells were rinsed in PBS, fixed in 4% paraformaldehyde for 15 minutes and washed in PBS three times. Fixed cells were permeabilized with 0.2% Triton X-100 for 20 minutes, washed in PBS and then blocked in PBS supplemented with 5% goat serum and 10% glycerol. Cells were incubated with indicated primary antibody at 4° C. overnight. Cells were washed three times with PBS and incubated with secondary antibody that was conjugated with Alexa Fluor 488 (Thermo Fisher Scientific) for 1 hour at room temperature. After the final wash, cells were counterstained with Vectashield (Vector Laboratories) containing DAPI (4', 6-diamidino-2-phenylindole). Images were captured using Zeiss laser confocal microscope (LSM780).

Prostate Cancer Tissue Specimens, Immunohistochemistry (IHC), and Staining Scoring Prostate cancer tissue microarrays (TMAs) were purchased from US Biomax, Inc (Cat. #PR2085b and PR803a). TMA specimens were used for antigen retrieval and immunostaining as described previously (Huang et al, 2001 J Biol Chem 276:38830-38836; Zhang et al, 2011 Cancer Res 71:3257-3267). Primary antibodies used were anti-FOXO1 (Bethyl) and anti-pERK (Cell Signaling Technology). Staining intensity was graded/scored in a blinded fashion: 1=weak staining at 100× magnification but little or no staining at 40× magnification; 1.5=weak staining at 40× magnification; 2=medium staining at 40× magnification; 2.5=medium plus staining at 40× magnification; 3=strong staining at 40× magnification and 3.5=very strong staining at 40× magnification. A final staining index was obtained by multiplying values of staining percentage and intensity.

Generation, Treatment and Imaging of Prostate Cancer Xenografts in Mice 6-week-old NOD-SCID IL-2-receptor gamma null (NSG) mice were generated in house and randomly grouped for animal experiments. The animal study was approved by IACUC. All mice were housed in standard conditions with a 12 hours light/dark cycle and access to food and water ad libitum. PC-3-Luc cells ($5 \times 10^6$) infected with lentivirus expressing empty vector (E.V.) or the FOXO1 peptide HA-FOXO1-IQBP(SE) (in 100 µl 1×PBS plus 100 µl Matrigel (BD Biosciences)) were injected subcutaneously into the right flank of mice. After xenografts reached the size of approximately 100 mm$^3$ (7 days after implantation), tumor-positive animals were randomly divided into different treatment groups. Vehicle (0.9% saline/mock treatment) or DTX (10 mg/ml, Sandoz Inc.) at 5 mg/kg was administered by intravenous injection twice a week (first and fourth day of the week). Tumor growth was monitored blindly by living imaging. Generally, luciferin (150 mg/kg) was administrated by intraperitoneal injection 10 minutes before imaging and then mice were anaesthetized with 3% isoflurane and imaged in an IVIS spectrum imaging system (Xenogen). Images were analyzed with Living Image software (Xenogen). Bioluminescent flux (photons $s^{-1}$ $sr^{-1}$ $cm^{-2}$) was determined for the xenograft tumors. Upon the completion of treatment, tumor grafts were harvested. Tumor tissues were divided, and a portion was fast-frozen into OCT for frozen section, a portion was formalin fixed and paraffin embedded and the rest was frozen for protein and RNA extraction.

RT-qPCR

Total RNA was isolated from cells and cDNA was synthesized using the Super-Script kit from Invitrogen. Two-step real-time polymerase chain reaction (PCR) was performed using the SYBR Green Mix (BioRad) and an iCycler iQ™ detection system (Bio-Rad) according to manufacturer's instructions. Both forward and reverse primers were used at a final concentration of 200 nM. The expression of GAPDH gene in each sample was used as an internal control. Information for primers used is provided in Table 2.

TABLE 2

Sequences for primers.

| Gene | RT Forward | SEQ ID NO: | RT Reverse | SEQ ID NO: |
|---|---|---|---|---|
| GLUT1 | GCTGTGCTTATGGGCTTCTC | 17 | CACATACATGGGCACAAAGC | 18 |
| LDHA | TGGAGTGGAATGAATGTTGC | 19 | ATAGCCCAGGATGTGTAGCC | 20 |
| PKM2 | ATTATTTGAGGAACTCCGCCGCCT | 21 | ATTCCGGGTCACAGCAATGATGG | 22 |

Measurements of Glucose Consumption and Lactate Production.

At 24 hours after plasmid transfection or 48 hours after lentivirus infection the spent medium was collected for measurement of glucose and lactate concentrations. Glucose levels were determined using a glucose (GO) assay kit (Sigma-Aldrich). Glucose consumption was the difference in glucose concentration in spent medium when compared with unused cell culture medium. Lactate levels were determined using a lactate assay kit (Eton Bioscience).

Statistical Analysis

Experiments were carried out with two or more replicates unless otherwise stated. Statistical analyses were performed with Student t test unless otherwise indicated. P values <0.05 are considered statistically significant.

Example 2: Phosphorylation of FOXO Activates Tumor Suppressor Functions

Identification of the Scaffold Protein IQGAP1 as a Binding Partner of FOXO1

Figure 2A:
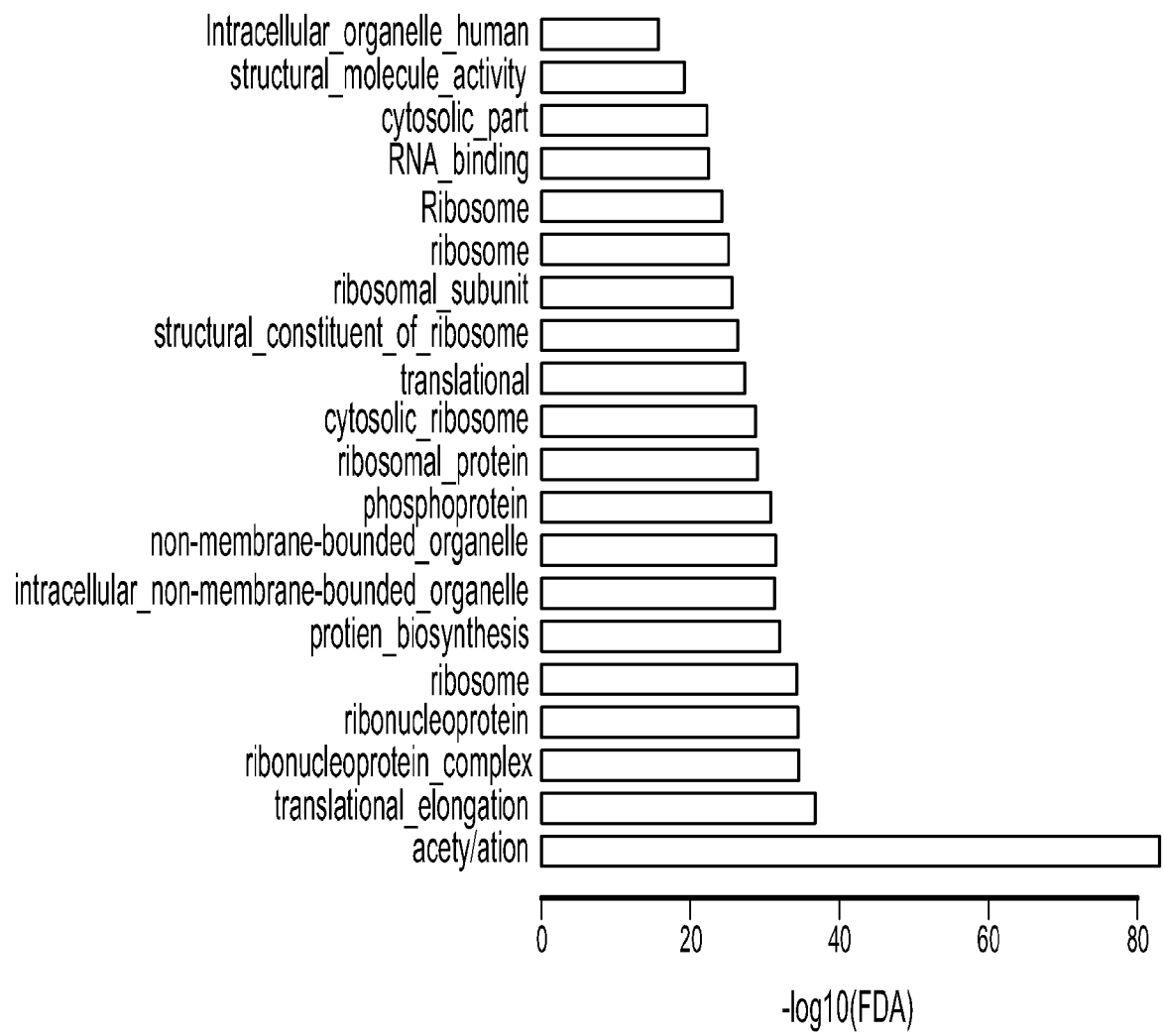
FIG. 2 shows diverse functions of FOXO1 binding proteins, PTEN expression in PCa cell lines, and S319 phosphorylation-enhanced interaction of FOXO1 and IQGAP1. A) Gene ontology analysis reveals the categories ($p<0.05$) of diverse functions of FOXO1 binding proteins identified by tandem affinity purification-coupled mass spectrometry. B) Western blot analysis of PTEN protein expression in DU145 (PTEN-positive) and LNCaP (PTEN-negative) PCa cell lines. ERK2 was used as loading control. C) Two replicates of experiments shown in FIG. 1F. In vitro protein binding assay. GST and GST-FOXO1-3 (amino acids 211-419) purified from bacteria were subjected to AKT kinase assay with IgG or HA-AKT-CA immunoprecipitated from HA-AKT-CA-transfected C4-2 cells before incubating with in vitro translated Flag-IQGAP1 for protein binding assay. D) Western blot bands of IQGAP1 proteins in GST pull down and input samples as shown in FIG. 1F were quantified first. The quantitative value of IQGAP1 in GST pull down samples was then normalized by the value of IQGAP1 in input samples, and normalized value in each group was further normalized to that in the GST-FOXO1-3 plus IgG group. Quantification and normalization were performed in a similar manner for the western blot bands in the two repeated experiments shown in (C). The data from three replicates (n=3) were used to generate the figure shown in this panel.

To search for novel functions of FOXO1, a FOXO1 mammalian expression vector (SFB-FOXO1) was constructed that contains S, Flag, and biotin-binding-protein-(streptavidin)-binding-peptide tags. This plasmid and the backbone vector were transfected separately into 293T cells, and cell extracts were prepared for tandem affinity purification and mass spectrometry. A total of 109 proteins were identified with confidence, which include FOXO1 (bait), known FOXO1-interacting proteins such as USP7/HAUSP, and PLK1 (van der Horst et al, 2006 Nat Cell Biol 8:1064-1073; Yuan et al, 2014 Cell Cycle 13:807-819), and a large number of new binding partners such as IQGAP1 (FIG. 1A and Table 3). Gene Ontology analysis indicates that FOXO1-associated proteins are involved in many biological processes such as protein biosynthesis, translation elongation, and acetylation (FIG. 2A). Because IQGAP1 is a scaffold protein that is important for activation of the Raf-MEK-ERK pathway and tumorigenesis (White et al, 2012 Cellular *Signal* 24:826-834), the molecular basis of the interaction between FOXO1 and IQGAP1 and the biological impact of their interaction on cancer cell growth and therapy resistance was investigated.

TABLE 3

Binding partners.

| Name of Protein Identified | ID | Number of Peptides Identified |
|---|---|---|
| PRKDC | IPI: IPI00296337.2 | 61 |
| XRCC6 | IPI: IPI00644712.4 | 38 |
| FOXO1 | IPI: IPI00289866.6 | 36 |
| XRCC5 | IPI: IPI00220834.8 | 35 |
| YWHAE | IPI: IPI00000816.1 | 26 |
| MYH9 | IPI: IPI00019502.3 | 24 |
| MYH10 | IPI: IPI00397526.3 | 22 |
| HSPA8 | IPI: IPI00003865.1 | 16 |
| DDX21 | IPI: IPI00015953.3 | 16 |
| RPS3_IPI: IPI00011253.3 | IPI: IPI00011253.3 | 16 |
| TUBB2C | IPI: IPI00007752.1 | 12 |
| HSPA9 | IPI: IPI00007765.5 | 12 |
| HNRNPU | IPI: IPI00479217.1 | 11 |
| RPA1 | IPI: IPI00020127.1 | 10 |
| PARP1 | IPI: IPI00449049.5 | 10 |
| YWHAQ | IPI: IPI00018146.1 | 9 |
| ACTB | IPI: IPI00021439.1 | 8 |
| YWHAZ | IPI: IPI00021263.3 | 8 |
| HSPA5 | IPI: IPI00003362.2 | 8 |
| RPL4 | IPI: IPI00003918.6 | 8 |
| ACTA2 | IPI: IPI00008603.1 | 8 |
| SLC25A5 | IPI: IPI00007188.5 | 8 |
| ACACA | IPI: IPI00011569.2 | 8 |
| MYBBP1A | IPI: IPI00005024.3 | 8 |
| NPM1 | IPI: IPI00220740.1 | 7 |
| YWHAH | IPI: IPI00216319.3 | 7 |
| YWHAB | IPI: IPI00216318.5 | 7 |
| DDX5 | IPI: IPI00017617.1 | 7 |
| RPS3A | IPI: IPI00419880.6 | 7 |
| YWHAG | IPI: IPI00220642.7 | 6 |
| RPL3 | IPI: IPI00550021.4 | 6 |
| IQGAP1 | IPI: IPI00009342.1 | 6 |
| RPL7 | IPI: IPI00030179.3 | 6 |
| EPRS | IPI: IPI00013452.9 | 6 |
| RPL6 | IPI: IPI00329389.8 | 6 |
| HNRNPM | IPI: IPI00171903.2 | 6 |
| C1QBP | IPI: IPI00014230.1 | 5 |
| CKAP4 | IPI: IPI00141318.2 | 5 |
| TUBA4A | IPI: IPI00007750.1 | 5 |
| RPS2 | IPI: IPI00013485.3 | 5 |
| RPS6 | IPI: IPI00021840.1 | 5 |
| RPS4X | IPI: IPI00217030.1 | 5 |
| CYFIP1 | IPI: IPI00644231.3 | 5 |
| EEF1A2 | IPI: IPI00014424.1 | 5 |
| ACTBL2 | IPI: IPI00003269.1 | 5 |
| DHX9 | IPI: IPI00844578.1 | 5 |
| TUBB | IPI: IPI00011654.2 | 4 |
| SSBP1 | IPI: IPI00029744.1 | 4 |
| HSPA1A | IPI: IPI00304925.5 | 4 |
| RPS8 | IPI: IPI00216587.9 | 4 |
| SPTAN1 | IPI: IPI00744706.2 | 4 |
| TUBA1C | IPI: IPI00166768.3 | 4 |
| RSL1D1 | IPI: IPI00008708.5 | 4 |
| RPL18 | IPI: IPI00215719.6 | 4 |
| HIST1H4J | IPI: IPI00453473.6 | 4 |
| RPL13P12 | IPI: IPI00397611.2 | 4 |
| VIM | IPI: IPI00418471.6 | 4 |
| RPL8 | IPI: IPI00012772.8 | 4 |
| RPS16 | IPI: IPI00221092.8 | 4 |
| HNRNPF | IPI: IPI00003881.5 | 3 |
| HNRNPH1 | IPI: IPI00013881.6 | 3 |

TABLE 3-continued

Binding partners.

| Name of Protein Identified | ID | Number of Peptides Identified |
|---|---|---|
| RPL7A | IPI: IPI00299573.1 | 3 |
| RPS14 | IPI: IPI00026271.5 | 3 |
| EEF1A1 | IPI: IPI00025447.8 | 3 |
| GNL3 | IPI: IPI00003886.3 | 3 |
| KPNA2 | IPI: IPI00002214.1 | 3 |
| SYNCRIP | IPI: IPI00018140.3 | 3 |
| DDX3X | IPI: IPI00215637.5 | 3 |
| HIST2H2BE | IPI: IPI00003935.6 | 3 |
| FLNA | IPI: IPI00302592.2 | 3 |
| HIST1H1C | IPI: IPI00217465.5 | 3 |
| RPS9 | IPI: IPI00221088.5 | 3 |
| DDX17 | IPI: IPI00023785.7 | 3 |
| PTCD3 | IPI: IPI00783302.1 | 3 |
| RPS13 | IPI: IPI00221089.5 | 3 |
| SFN | IPI: IPI00013890.2 | 3 |
| RPA2 | IPI: IPI00013939.3 | 3 |
| SERBP1 | IPI: IPI00410693.3 | 2 |
| AP2B1 | IPI: IPI00784156.1 | 2 |
| SETD7 | IPI: IPI00028366.2 | 2 |
| DHX30 | IPI: IPI00411733.4 | 2 |
| DNAJA1 | IPI: IPI00012535.1 | 2 |
| MRPS9 | IPI: IPI00641924.2 | 2 |
| PTBP1 | IPI: IPI00179964.5 | 2 |
| SLC25A13 | IPI: IPI00007084.3 | 2 |
| PTPLAD1 | IPI: IPI00008998.3 | 2 |
| ILF2 | IPI: IPI00005198.2 | 2 |
| DBT | IPI: IPI00003944.1 | 2 |
| USP7 | IPI: IPI00003965.5 | 2 |
| MATR3 | IPI: IPI00017297.1 | 2 |
| RAD50 | IPI: IPI00107531.1 | 2 |
| EP300 | IPI: IPI00020985.4 | 2 |
| HNRNPA3 | IPI: IPI00419373.1 | 2 |
| RPL21P19 | IPI: IPI00247583.5 | 2 |
| HSPA7 | IPI: IPI00011134.2 | 2 |
| RPL11 | IPI: IPI00376798.3 | 2 |
| NAP1L1 | IPI: IPI00023860.1 | 2 |
| TUBB1 | IPI: IPI00006510.1 | 2 |
| RPL27 | IPI: IPI00219155.5 | 2 |
| GTPBP4 | IPI: IPI00385042.4 | 2 |
| HSPA1L | IPI: IPI00301277.1 | 2 |
| SPTBN1 | IPI: IPI00005614.6 | 2 |
| NCL | IPI: IPI00444262.3 | 2 |
| LRPPRC | IPI: IPI00783271.1 | 2 |
| PC | IPI: IPI00299402.1 | 2 |
| RPL13A | IPI: IPI00304612.9 | 2 |
| RPS18 | IPI: IPI00013296.3 | 2 |
| ABCF2 | IPI: IPI00005045.1 | 2 |
| KCTD12 | IPI: IPI00060715.1 | 2 |

Figure 1B:
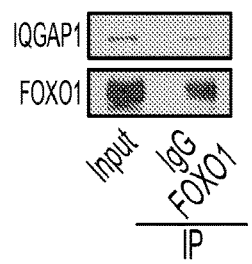
Figure 1C:
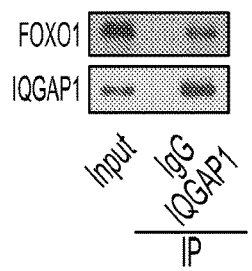
Figure 1D:
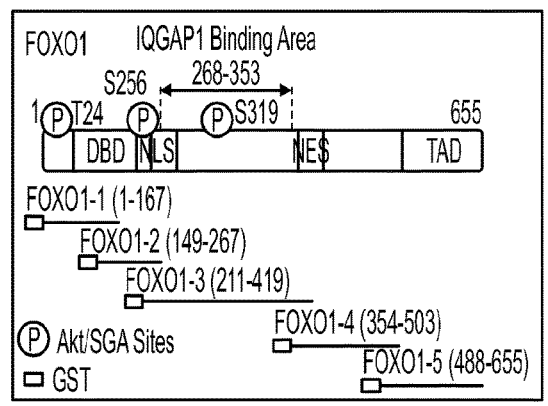
Figure 1E:
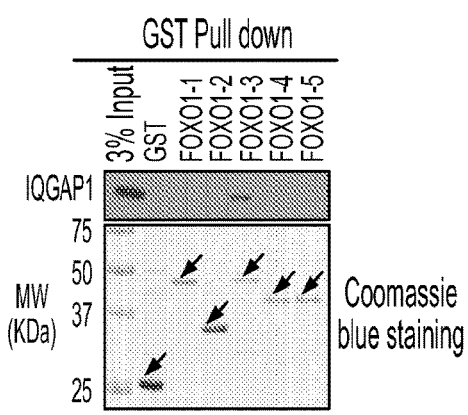
Figure 2B:
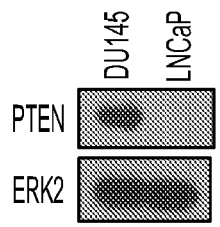

* Proteins with two or more peptides detected are considered confidently identified Co-immunoprecipitation (co-IP) assay confirmed that endogenous FOXO1 and IQGAP1 proteins associated with each other in PTEN-null LNCaP prostate cancer cells (FIGS. 1B and C, and FIG. 2B). To define which region in FOXO1 mediates its interaction with IQGAP1, glutathione-S-transferase (GST)-FOXO1 constructs (FIG. 1D) were generated, purified recombinant proteins from bacteria (FIG. 1E, lower panel) were generated, and GST pull-down assays were performed. It was demonstrated that GST-FOXO1-3 (amino acids 211-419), but not GST and other GST-FOXO1 recombinant proteins, interacted with IQGAP1 (FIG. 1E, upper panel), although the binding was relatively weak (see more data below). Nonetheless, these data suggested that the central portion (amino acids 268-353) of FOXO1 is important for its binding to IQGAP1.

Serine-319 Phosphorylation of FOXO1 is Important for FOXO1-IQGAP1 Interaction

Figure 3A:
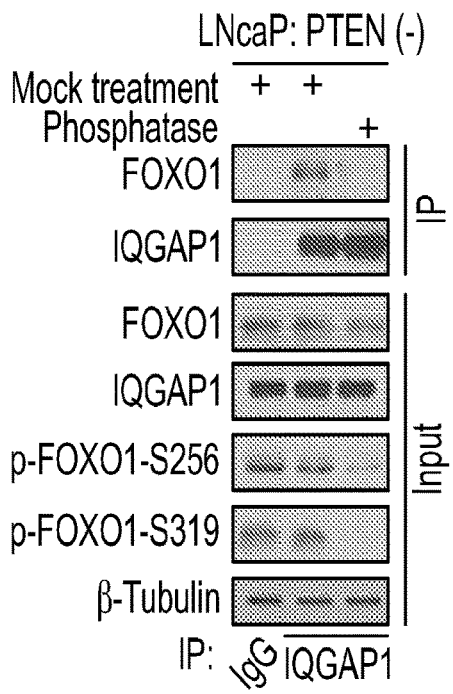
FIG. 3 shows that AKT phosphorylation of FOXO1 at serine 319 is critical for FOXO1 binding to IQGAP1. A) Western blot analysis of LNCaP whole cell lysates (WCL) and co-IP samples. Cell lysates were treated with or without λ phosphatase before IP. B) Western blot analysis of WCL and co-IP samples in DU145 cells 24 hours after transfected with indicated plasmids. C) Western blot analysis of WCL and co-IP samples in DU145 cells 48 hours after transfected with indicated siRNAs. D) Western blot analysis of WCL and co-IP samples in LNCaP cells. Cells were treated with 30 μM of LY294002 for 6 hours before IP. E and F) Western blot analysis of WCL and co-IP samples in LNCaP cells 24 hours after transfected with indicated plasmids.
Figure 3B:
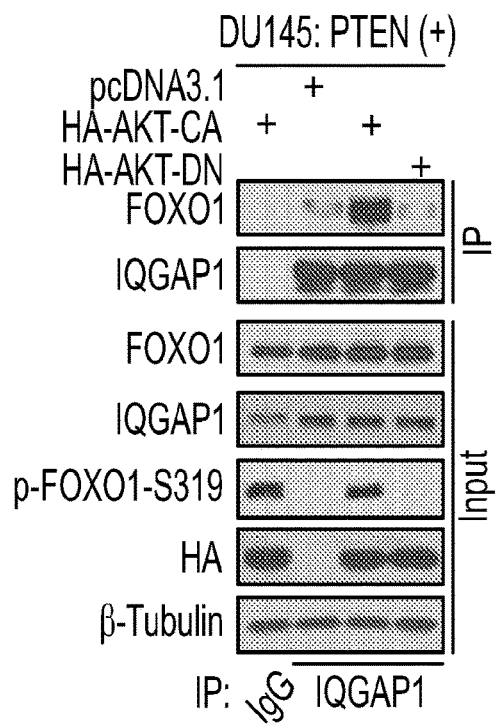
Figure 3C:
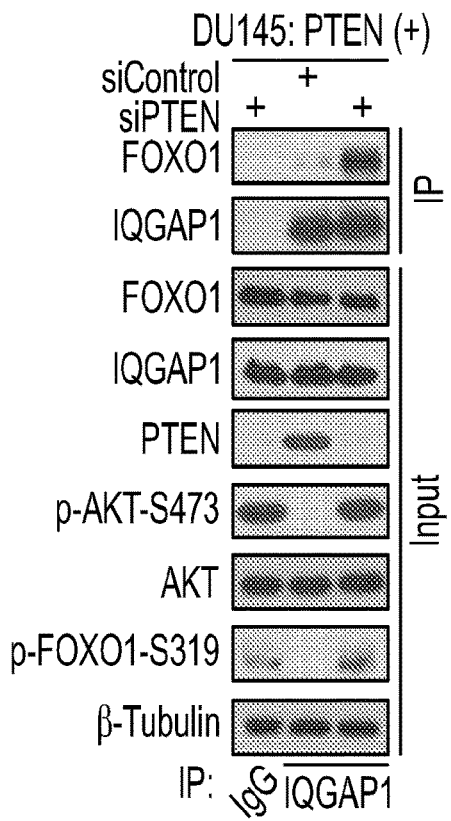
Figure 3D:
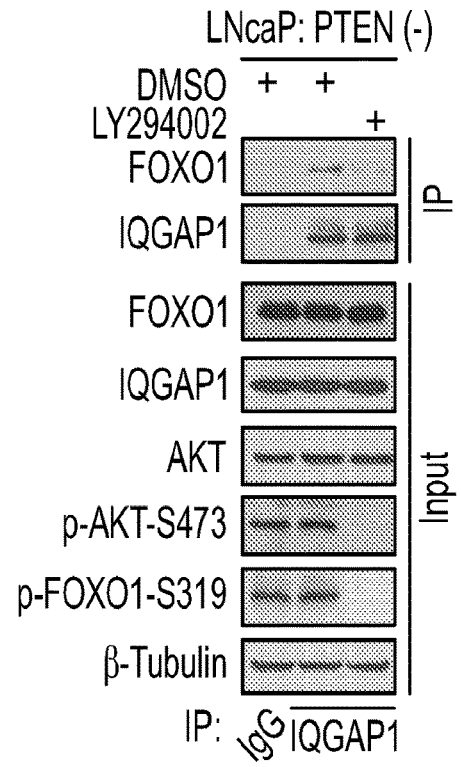
Figure 4A:
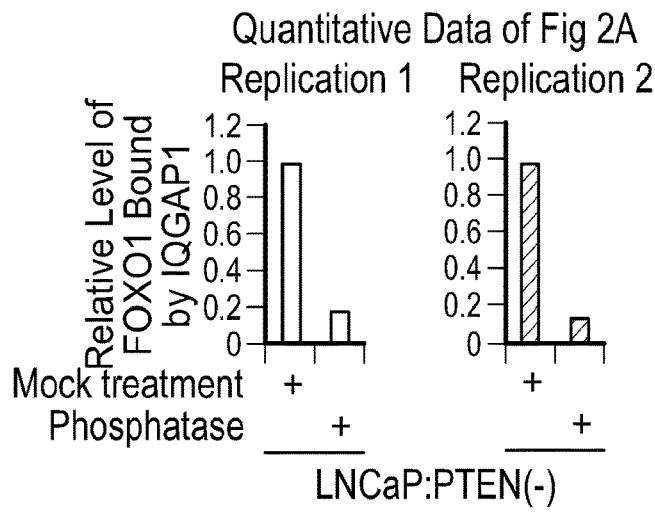
FIG. 4 shows quantitative data of the western blots shown in FIG. 3. A) FOXO1 proteins co-IP by IQGAP1 from cell lysates mock treated or treated with λ protein phosphatase as shown in FIG. 3A and the repeated experiment (replication 2) were quantified and normalized to the quantified value of IP-ed IQGAP1. The normalized values were further normalized to the value in mock treated group. The data from two replicates (n=2) were used to generate the figure shown in this panel. B) FOXO1 proteins co-IP by IQGAP1 from cells transfected with control vector pcDNA3.1, constitutively active HA-AKT-CA and kinase dead HA-AKT-DN as shown in FIG. 3B and the repeated experiment (replication 2) were quantified and normalized to the quantified value of IP-ed IQGAP1. The normalized values were further normalized to the value in cells transfected with the control vector pcDNA3.1. The data from two replicates (n=2) were used to generate the figure shown in this panel. C) FOXO1 proteins co-IP by IQGAP1 from cells transfected with control siRNA (siControl) and PTEN-specific siRNA (siPTEN) as shown in FIG. 3C and the repeated experiment (replication 2) were quantified and normalized to the quantified value of IP-ed IQGAP1. The normalized values were further normalized to the value in cells transfected with siControl. The data from two replicates (n=2) were used to generate the figure shown in this panel. D) FOXO1 proteins co-IP by IQGAP1 from cells mock treated (DMSO) or treated with the PI3K inhibitor LY294002 as shown in FIG. 3D and the repeated experiment (replication 2) were quantified and normalized to the quantified value of IP-ed IQGAP1. The normalized values were further normalized to the value in cells treated with DMSO. The data from two replicates (n=2) were used to generate the figure shown in this panel. E) IQGAP1 proteins co-IP by Flag-tagged FOXO1 proteins from cells transfected with Flag-FOXO1-WT, T24A, S256A, S319A and T24A/S256A/S319A (or A3) as shown in FIG. 3E and the repeated experiment (replication 2) were quantified and normalized to the quantified value of IP-ed Flag-FOXO1 proteins. The normalized values were further normalized to the value in cells transfected with FOXO1-WT. The data from two replicates (n=2) were used to generate the figure shown in this panel. F) IQGAP1 proteins co-IP by Flag-FOXO1 proteins from cells transfected with Flag-tagged, transcription-deficient Flag-FOXO1-537 (can be phosphorylated by AKT) and Flag-FOXO1-537-A3 (resistant to AKT phosphorylation) as shown in FIG. 3F and the repeated experiment (replication 2) were quantified and normalized to the quantified value of IP-ed Flag-FOXO1 proteins. The normalized values were further normalized to the value in cells transfected with FOXO1-537. The data from two replicates (n=2) were used to generate the figure shown in this panel.
Figure 4B:
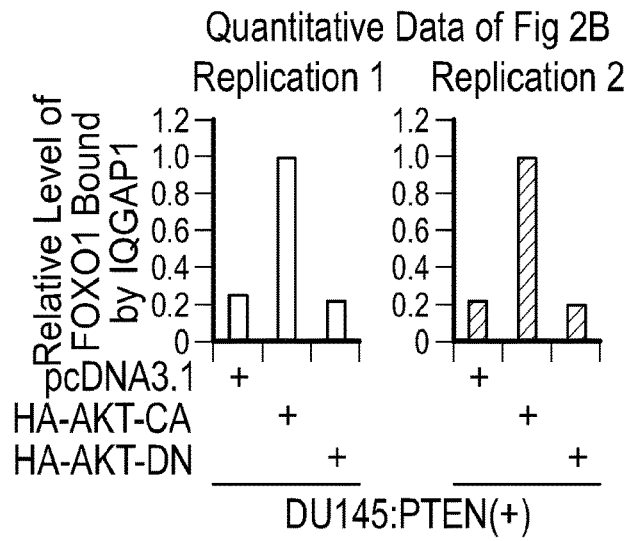
Figure 4C:
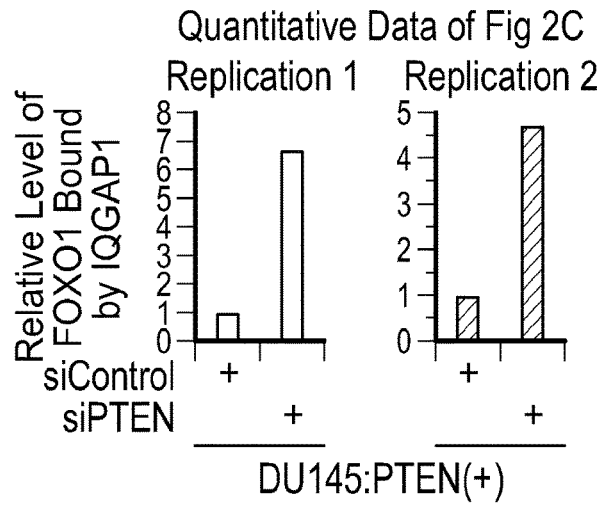
Figure 4D:
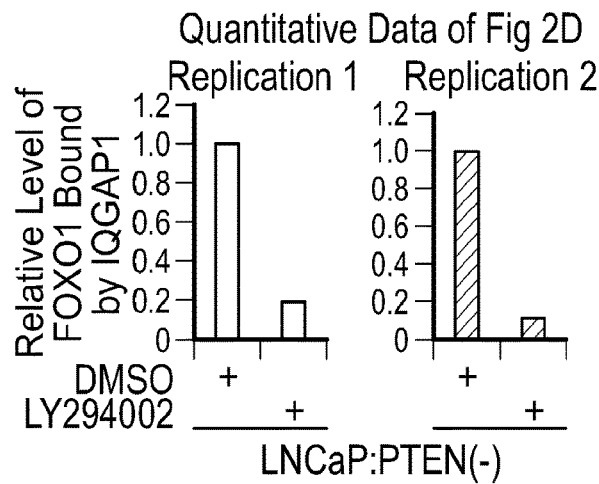

Given that the interaction between recombinant FOXO1 from bacteria and cellular IQGAP1 was much weaker than the input (FIG. 1E), the importance of FOXO1 binding to IQGAP1 posttranslational modification, such as phosphorylation of FOXO1, was examined. LNCaP cell (PTEN-negative) lysate was treated with X, protein phosphatase before co-IP assays. Threonine 24, serine 256, and serine 319 (T24, S256, and S319) residues in FOXO1 are readily phosphorylated by AKT in PTEN-negative cells (Biggs et al, 1999 *Proc Natl Acad Sci USA* 96:7421-7426; Tang et al, 1999 *J Biol Chem* 274:16741-16746). The effectiveness of phosphatase treatment was evident by reduction or depletion of FOXO1 phosphorylation at S256 and S319, respectively (FIG. 3A). Phosphatase treatment largely abrogated FOXO1-IQGAP1 interaction (FIG. 3A and FIG. 4A), an indication of the importance of phosphorylation for their interaction. In contrast, ectopic expression of a constitutively active AKT (AKT-CA), but not the kinase-dead mutant (AKT-DN), substantially enhanced FOXO1-IQGAP1 interaction in DU145 (PTEN-positive) prostate cancer cells (FIG. 2B, FIG. 3B, and FIG. 4B). Similarly, knockdown of endogenous PTEN in DU145 cells also markedly increased FOXO1-IQGAP1 interaction (FIG. 3C, and FIG. 4C). Conversely, inhibition of AKT by the PI3K inhibitor LY294002 decreased the FOXO1-IQGAP1 interaction to the background level in PTEN-null LNCaP cells (FIG. 3D, and FIG. 4D). These data indicated that FOXO1-IQGAP1 interaction is regulated by the PI3K-AKT pathway.

Figure 3E:
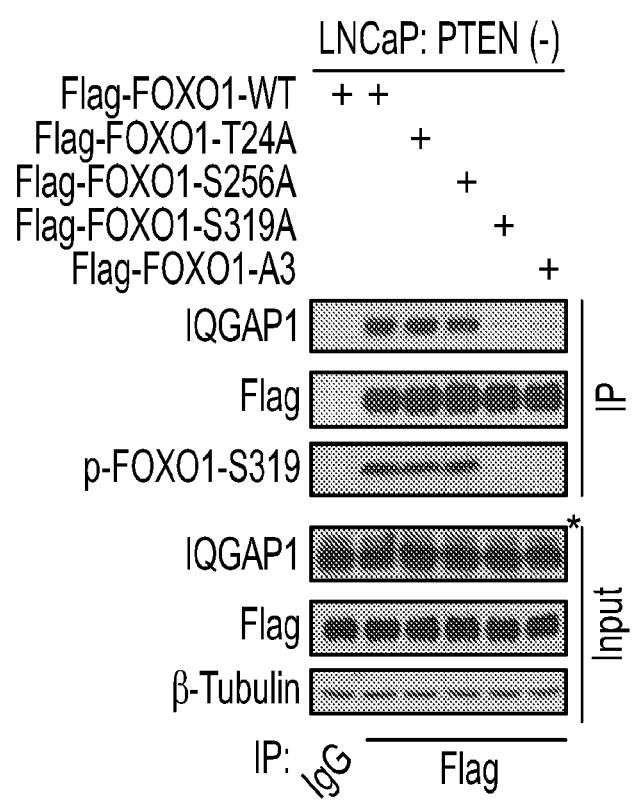
Figure 3F:
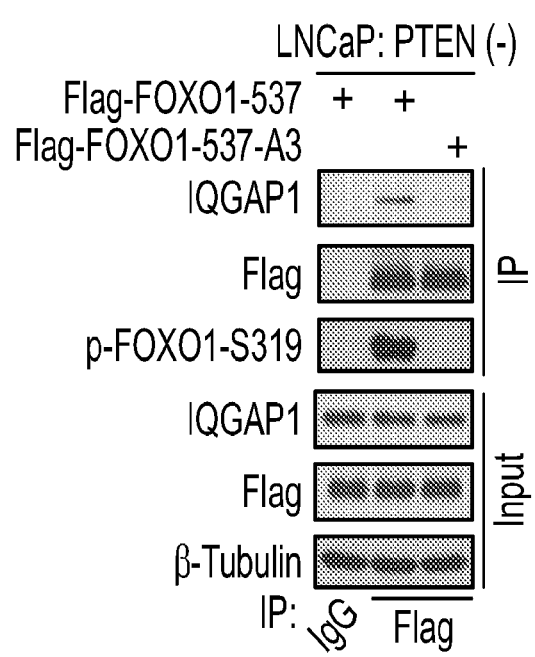
Figure 4E:
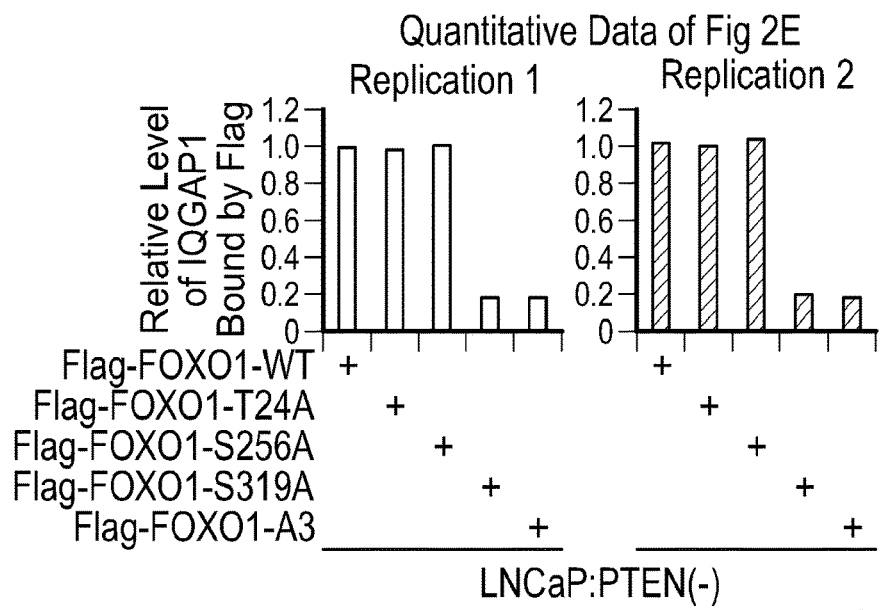
Figure 4F:
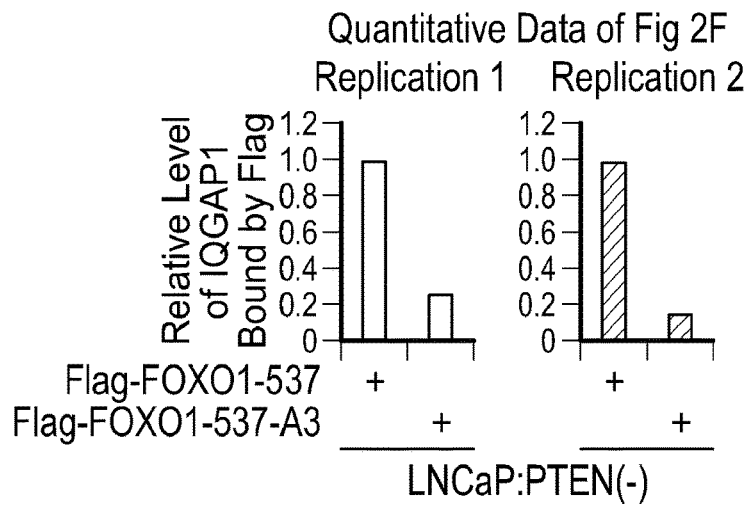

To determine whether AKT phosphorylation of FOXO1 is involved in FOXO1-IQGAP1 interaction, three AKT phosphorylation sites were mutated to alanine individually or together. Interaction of IQGAP1 with S319A and triple mutant (A3), but not T24A and S256A mutants, was decreased to the background level (FIG. 3E and FIG. 4E). FOXO1-A3 and S319A are two transcriptionally active mutants. Next, the possibility that the inhibition of FOXO1-IQGAP1 interaction caused by these two mutants was mediated indirectly through their downstream transcription targets was examined. FOXO1-537 is a transcription-deficient mutant of FOXO1, in which histidine 215, a key residue for DNA binding, is mutated to arginine and the transactivation domain (amino acids 538-655) is deleted (Liu et al, 2008 *Cancer Res* 68:10290-10299). Similar to the results shown in FIG. 3E, binding of the AKT phosphorylation-resistant mutant (FOXO1-537-A3) to IQGAP1 was lower compared with the "wild-type" counterpart FOXO1-537 (FIG. 3F and FIG. 4F).

Figure 1F:
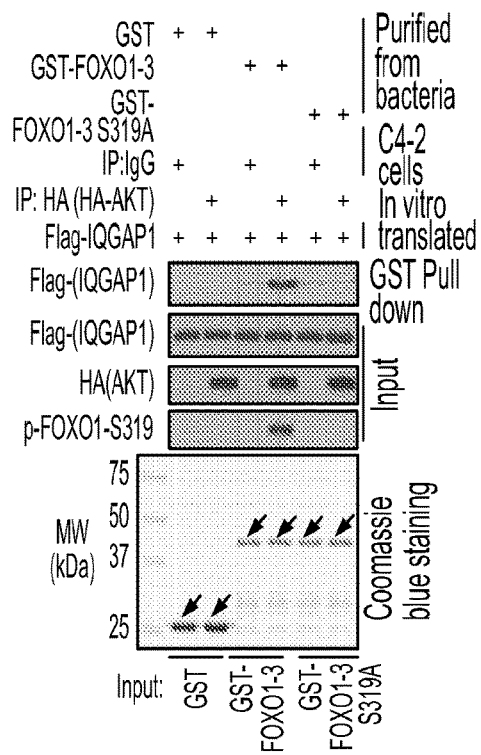
Figure 2C:
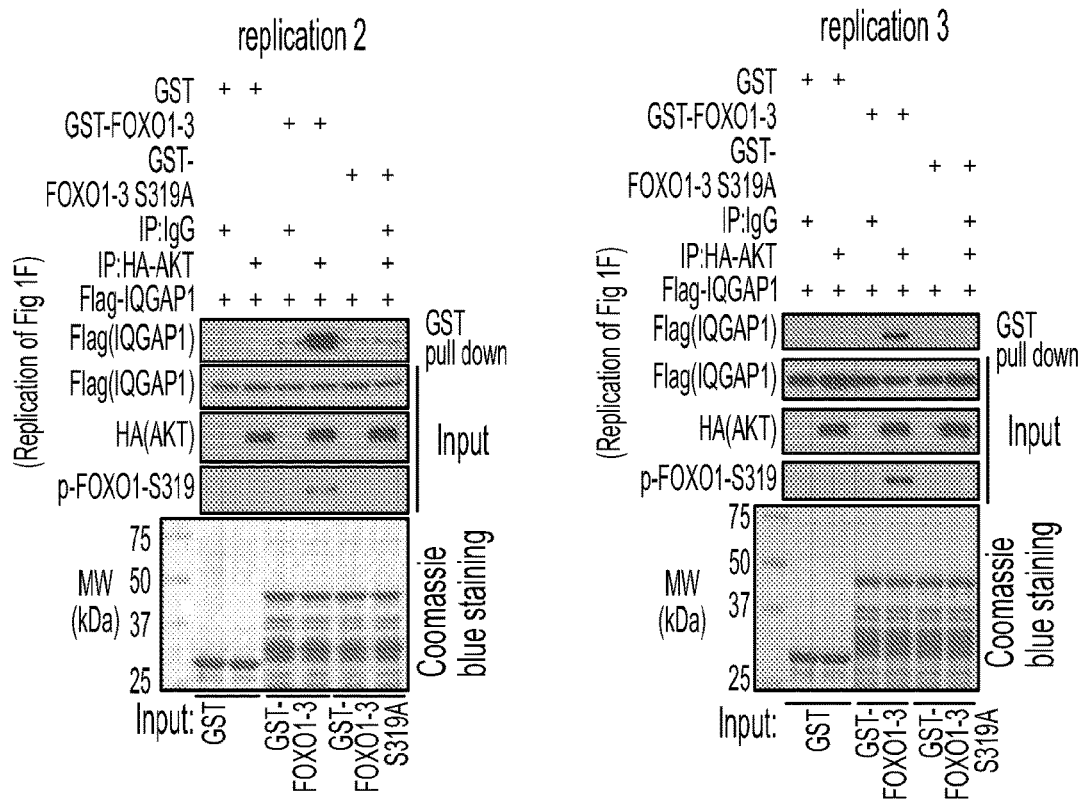
Figure 2D:
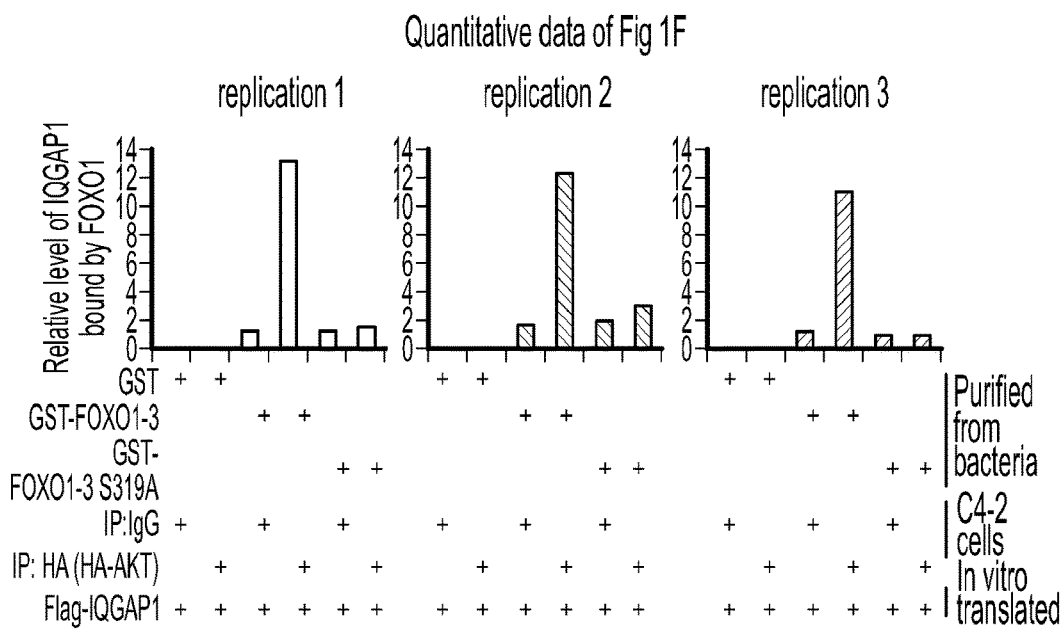

To further test the role of AKT phosphorylation of FOXO1 at S319 in mediating FOXO1-IQGAP1 interaction, HA-AKT was immunoprecipitated from C4-2 cells and in vitro kinase assays were performed using bacterially purified GST-FOXO1-3 (amino acids 211-419) and GST-FOXO1-3 S319A as substrates. In vitro protein binding assays were then carried out using AKT-phosphorylated GST-FOXO1-3 and in vitro transcribed and translated Flag-tagged IQGAP1. GST-FOXO1-3 had a basal-level interaction with IQGAP1 (FIG. 1F, and FIGS. 2C and D), which is consistent with the GST pull-down result using cellular IQGAP1 proteins (FIG. 1E). The interaction of IQGAP1 with GST-FOXO1-3, but not S319A mutant was substantially enhanced by AKT-mediated S319 phosphorylation of FOXO1 (FIG. 1F, and FIGS. 2C and D). Together, these data suggested that S319 phosphorylation of FOXO1 is important for FOXO1-IQGAP1 interaction and their interaction is unlikely mediated indirectly by its downstream transcription targets.

Figure 5A:
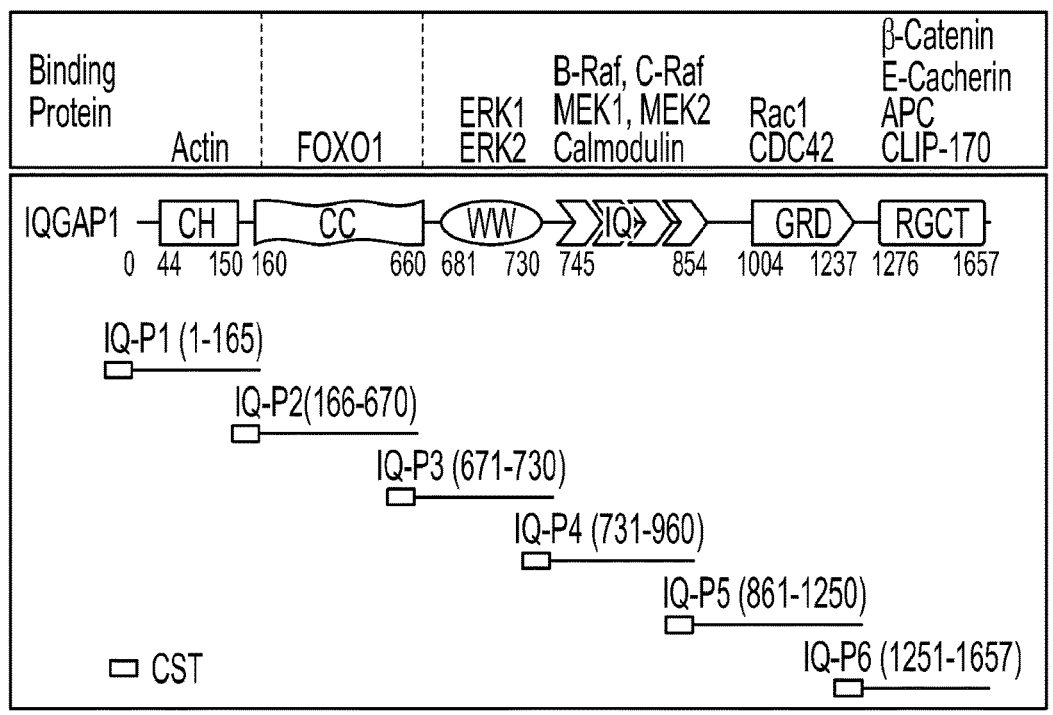
FIG. 5 shows that AKT-phosphorylated FOXO1 binds to IQGAP1 and inhibits IQGAP1 interaction with Raf, MEK, and ERK proteins. (A) Schematic diagram depicting the domain structure of IQGAP1 and 6 GST-IQGAP1 constructs. CC, coiled-coil domain. (B) LNCaP whole cell lysates (WCL) were subjected to GST pull-down by GST or GST-IQGAP1 recombinant proteins and Western blot analysis of FOXO1 proteins. (C) Western blot analysis of WCL and co-IP samples in LNCaP cells 48 hours after infected with lentivirus expressing control or FOXO1-specific shRNA. (D-F) Western blot analysis of WCL and co-IP samples in LNCaP cells 24 hours transfected with indicated plasmids. E.V., empty vector.
Figure 5B:
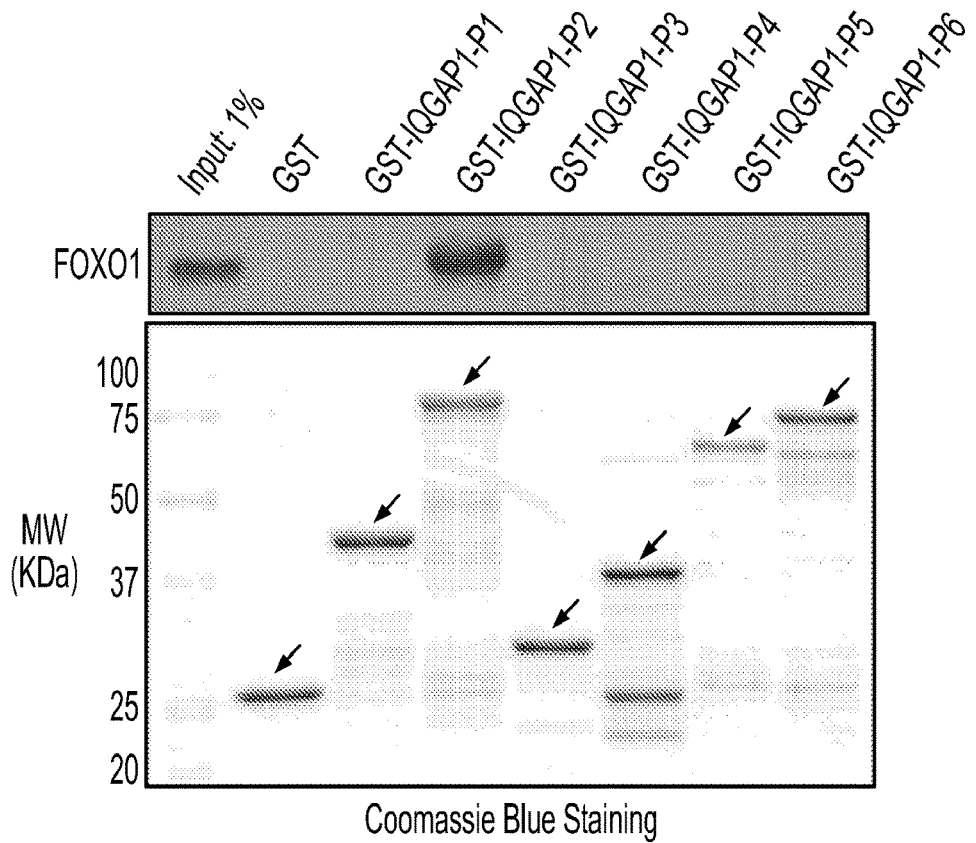
Figure 6A:
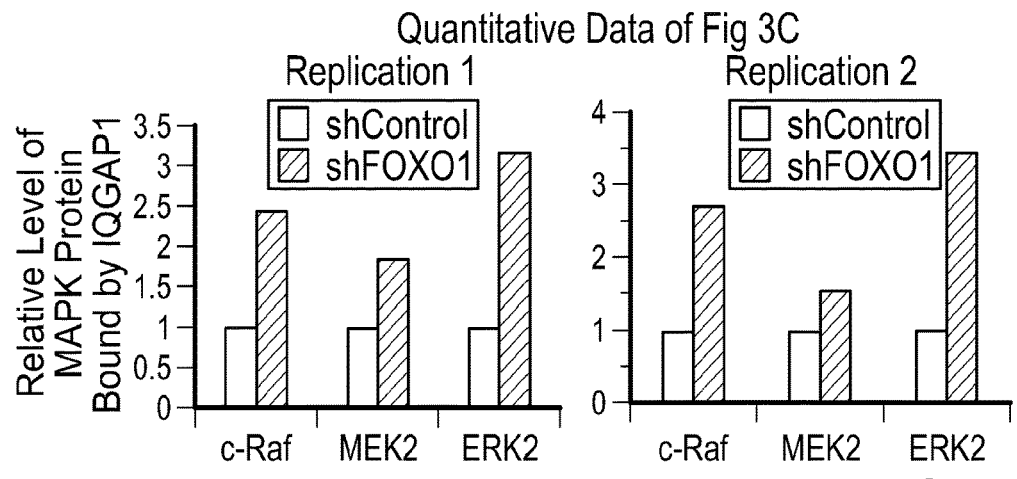
FIG. 6 shows quantitative data of the western blots shown in FIG. 5. A) MAPK pathway protein (c-Raf, MEK2 or ERK2) co-IP by IQGAP1 from cells infected with lentivirus expressing control shRNA (shControl) and FOXO1-specific shRNA (shFOXO1) as shown in FIG. 5C and the repeated experiment (replication 2) were quantified and normalized to the quantified value of IP-ed IQGAP1. The normalized values were further normalized to the value in cells infected with shControl. The data from two replicates (n=2) were used to generate the figure shown in this panel. B) MAPK pathway protein (c-Raf, MEK2 or ERK2) co-IP by IQGAP1 proteins, from cells transfected with control vector (pcDNA3.1), Flag-tagged transcription-deficient Flag-FOXO1-537 (can be phosphorylated by AKT) and Flag-FOXO1-537-A3 (resistant to AKT phosphorylation) as shown in FIG. 5D and the repeated experiment (replication 2), were quantified and normalized to the quantified value of IP-ed IQGAP1. The normalized values were further normalized to the value in cells transfected with pcDNA3.1. The data from two replicates (n=2) were used to generate the figure shown in this panel. C) MAPK pathway protein (c-Raf, MEK2 or ERK2) co-IP by IQGAP1 proteins, from cells transfected with control vector (pcDNA3.1), Flag-FOXO1-WT, Flag-FOXO1-NESm (primarily in the nucleus) and Flag-FOXO1-NLSm (cytoplasmic form) as shown in FIG. 5E and the repeated experiment (replication 2), were quantified and normalized to the quantified value of IP-ed IQGAP1. The normalized values were further normalized to the value in cells transfected with pcDNA3.1. The data from two replicates (n=2) were used to generate the figure shown in this panel. D) Two replicates of experiments shown in FIG. 5F. Western blot analysis of whole cell lysate and co-IP samples in LNCaP cells 24 hours transfected with indicated plasmids. E.V., empty vector. E) MAPK pathway protein (c-Raf, MEK2 or ERK2) co-IP by IQGAP1 proteins, from cells transfected with empty vector (EV, pcDNA3.1), HA-tagged FOXO1 peptide FOXO1-S319, phospho-mimicking peptide HA-FOXO1-IQBP-S319E and non-phosphorylatable peptide HAFOXO1-S319A as shown in FIG. 5F, were quantified and normalized to the quantified value of IP-ed IQGAP1. The normalized values were further normalized to the value in cells transfected with EV. Quantification and normalization were performed in a similar manner for the western blot bands in the two repeated experiments shown in (D). The data from three replicates (n=3) were used to generate the figure shown in this panel.
Figure 6B:
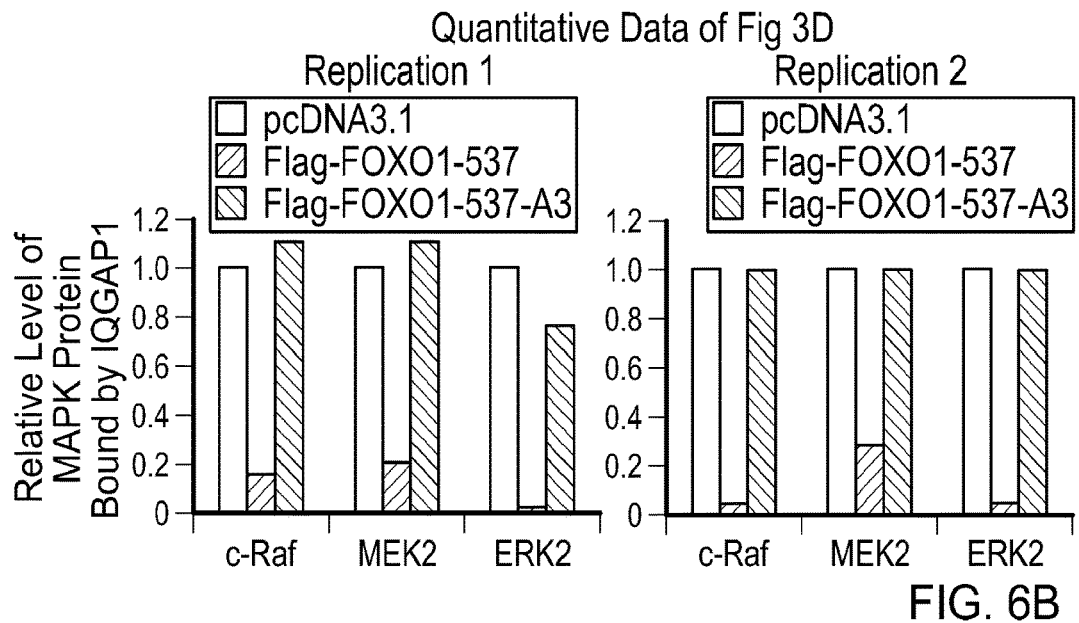

AKT-Phosphorylated FOXO1 Inhibits IQGAP1 Binding to c-Raf, MEK, and ERK Proteins To determine which domain of IQGAP1 is involved in FOXO1 binding, we generated six GST-IQGAP1 recombinant proteins corresponding to six well-studied functional domains of IQGAP1 (FIG. 5A). GST pull-down assays showed that the coiled-coil domain of IQGAP1 specifically interacted with FOXO1 proteins in LNCaP cells (FIG. 5B). Similar to the findings in other cell types (Jameson et al, 2013 *Nat Med* 19:626-630; Ren et al, 2007 *Proc Natl Acad Sci USA* 104:10465-10469; Roy et al, 2004 *J Biol Chem* 279:17329-17337; Roy et al, 2005 *Mol Cell Biol* 25:7940-7952), IQGAP1 interaction with c-Raf, MEK2, and ERK2 was readily detected in LNCaP cells (FIG. 5C). Although knockdown of endogenous FOXO1 had no effect on the steady-state levels of ERK2 and other MAPK proteins, it markedly increased their interaction with IQGAP1 (FIG. 5C, and FIG. 6A). Moreover, expression of FOXO1-537 diminished IQGAP1 interaction with c-Raf, MEK2, and ERK2, whereas almost no inhibitory effect was observed for FOXO1-537-A3 (FIG. 5D, and FIG. 6B). This result was in agreement with the difference in the capacity of FOXO1-537 and the A3 mutant to bind to IQGAP1 (FIG. 3F).

Figure 6C:
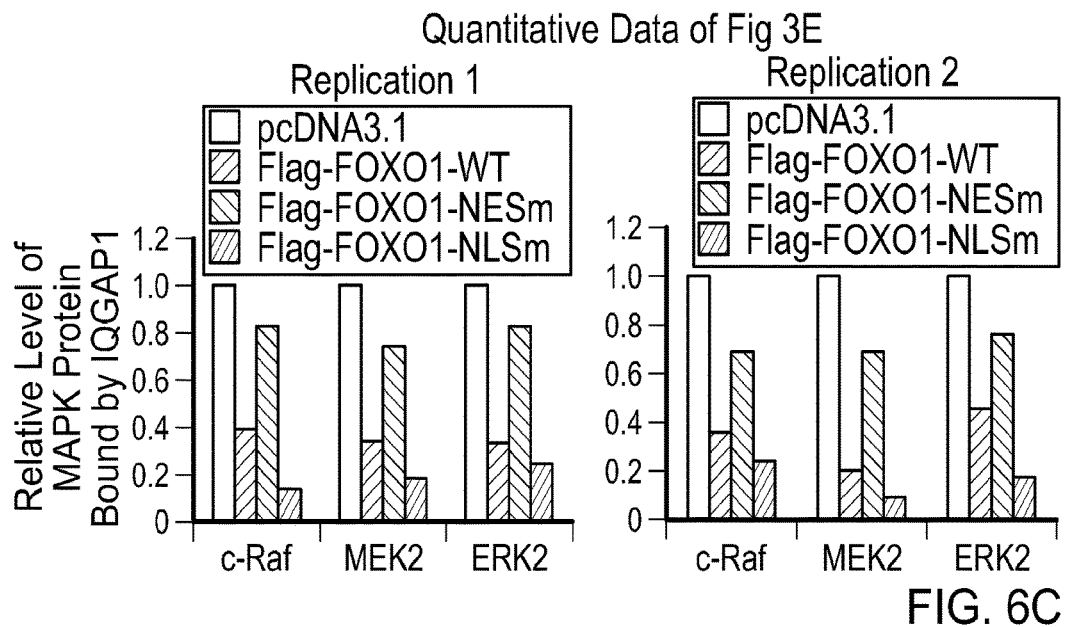
Figure 6D:
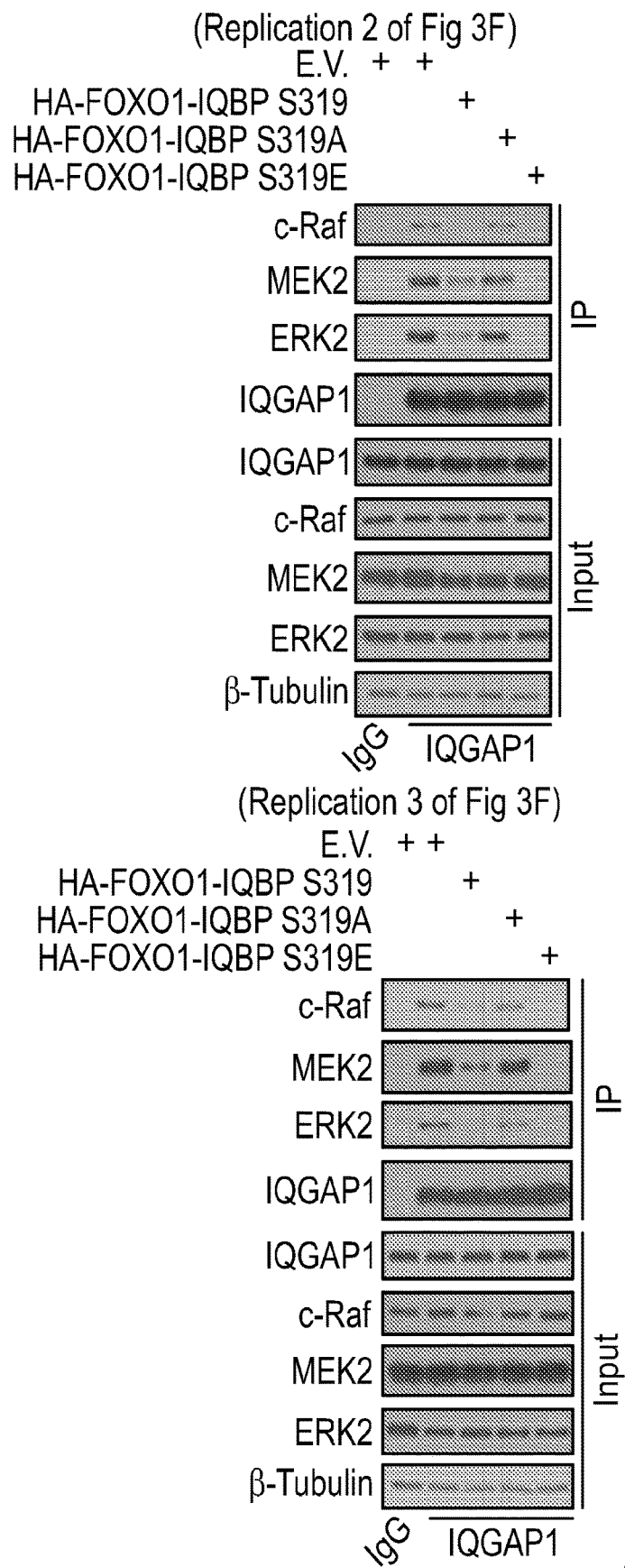
Figure 6E:
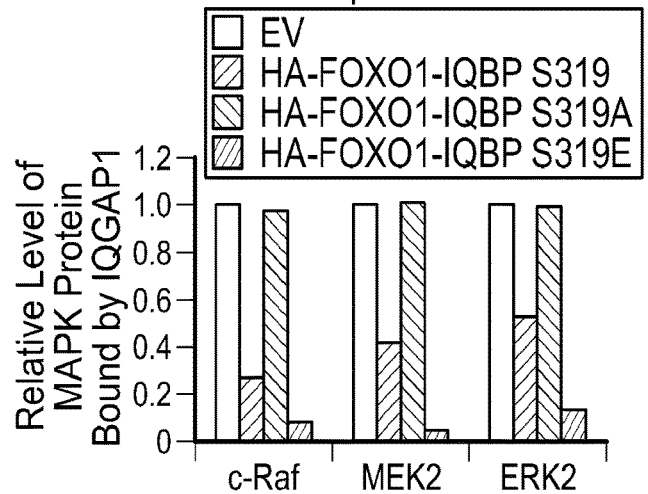
Figure 6E:
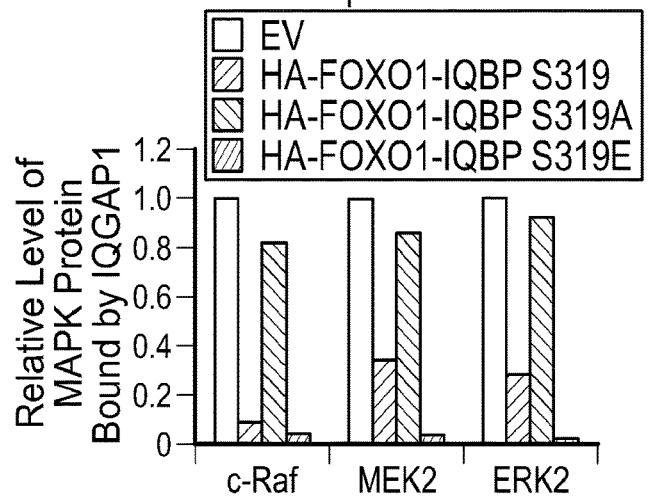
Figure 6E:
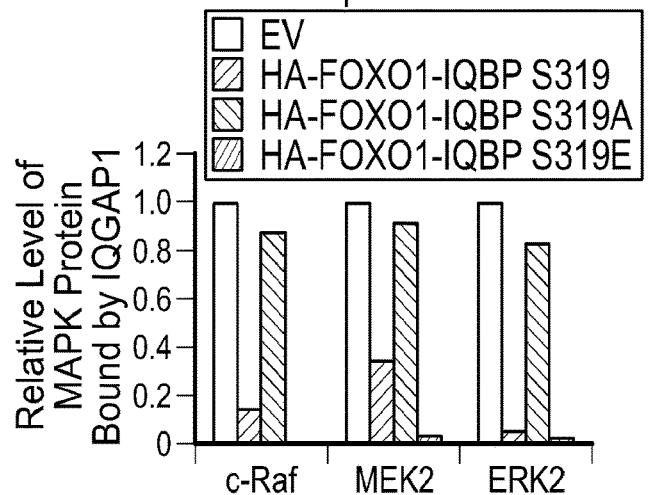
Figure 7A:
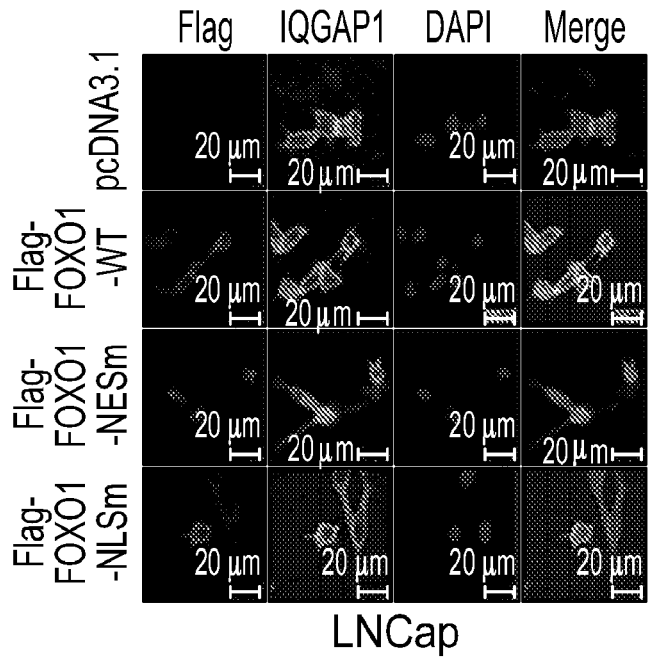
FIG. 7 shows an assessment of cellular localization of FOXO1 and phospho-mimicking FOXO1 peptide HA-FOXO1-IQBP S319E and its "wild-type" (S319) and non-phosphorylatable (S319A) counterparts in PCa cells. A and B) Immunofluorescent cytochemistry using antibodies for anti-Flag and IQGAP1 in LNCaP cells transfected with control vector (pcDNA3.1) and plasmids for Flag-FOXO1-WT, Flag-FOXO1-NESm and Flag-FOXO1-NLSm. Cellular localization (nuclear, cytoplasm or both) was photographed (A) and analyzed in >100 cells in each experimental condition (B). The experiment was repeated at least once and similar results were obtained. C) Immunofluorescent cytochemistry using antibodies for anti-HA and IQGAP1 in LNCaP cells transfected with empty vector (E.V.) pcDNA3.1 and plasmids for phospho-mimicking FOXO1 peptide HA-FOXO1-IQBP S319E and its "wild-type" (S319) and non-phosphorylatable (S319A) counterparts. >100 cells in each experimental condition were analyzed. The experiment was repeated at least once and similar results were obtained. D) LNCaP cells were transfected with SFB-tagged empty vector (SFB-EV) and SFB-tagged plasmids for phospho-mimicking FOXO1 peptide SFB-FOXO1-IQBP S319E and its "wild-type" (S319) and non-phosphorylatable (S319A) counterparts. 24 hours after transfection, cells were harvested and lysed for co-IP with IgG or anti-Flag antibodies and immunoprecipitated proteins were analyzed by western blotting. SFB tags are S, Flag and Biotin-binding protein (streptavidin) binding peptide tags. These three tags encode an approximately 12-kDa peptide (119 amino acids). E) LNCaP cells were transfected with SFB-tagged plasmids for phospho-mimicking FOXO1 peptides SFB-FOXO1-IQBP S319E and S319D and the non-phosphorylatable counterpart S319A. 24 hours after transfection, cells were harvested and lysed for co-IP with IgG or anti-Flag antibodies and immunoprecipitated proteins were analyzed by western blotting. F) LNCaP cells were transfected with SFB-tagged empty vector (EV) and SFB-tagged plasmids for SFB-FOXO1-IQBP S319E and its "wild-type"
Figure 7B:
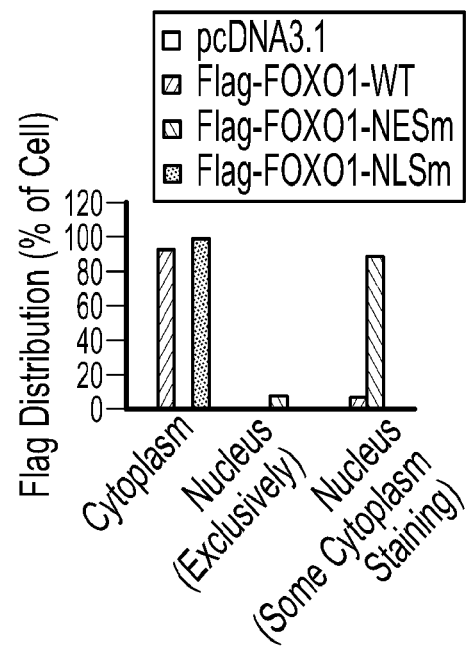
Figure 7C:
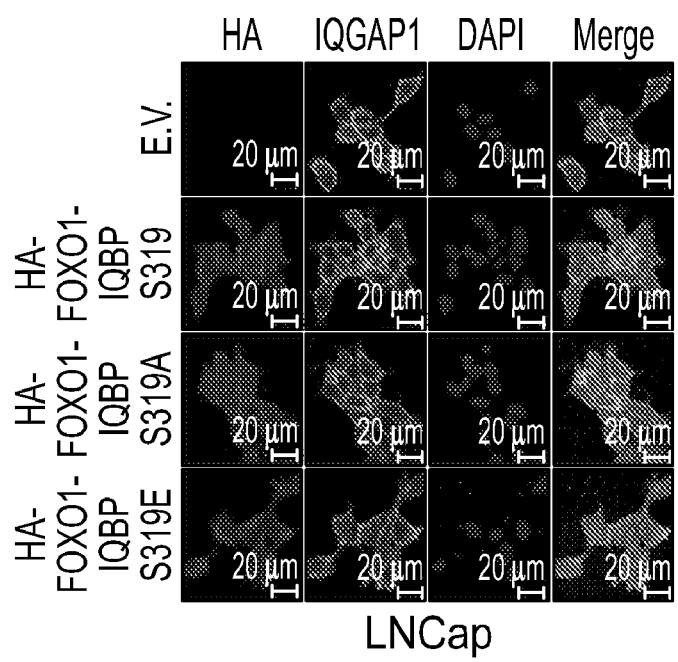
Figure 7D:
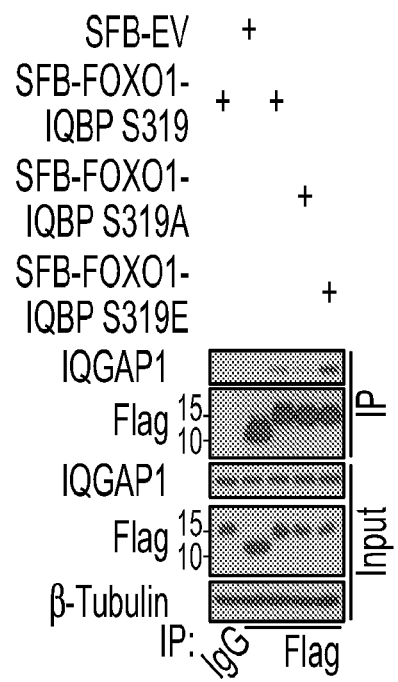
Figure 7E:
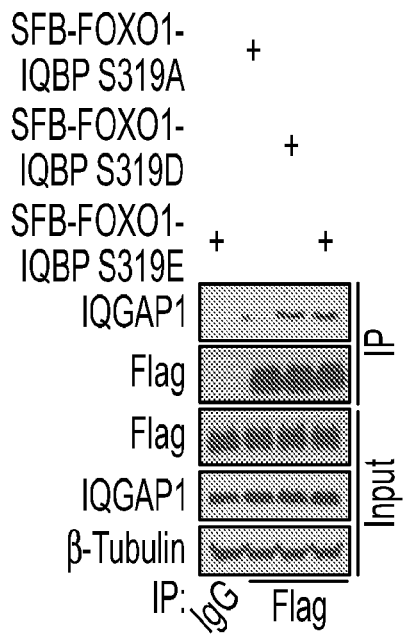
Figure 7F:
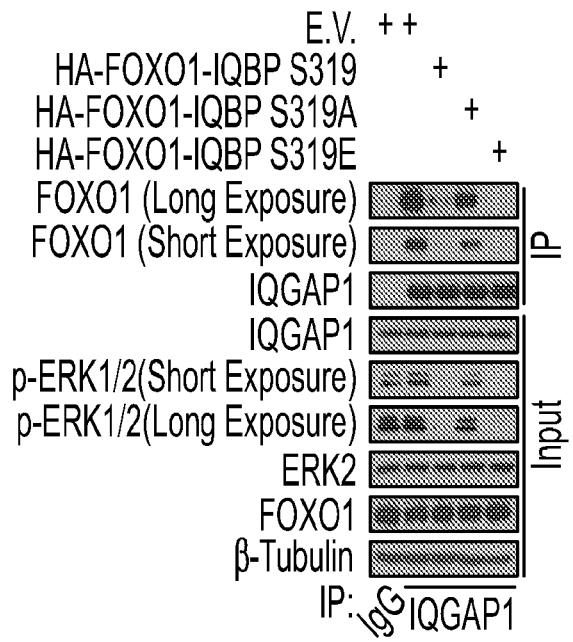

Given that AKT phosphorylation induces cytoplasm localization of FOXO proteins, we examined the impact of FOXO1 cellular localization on IQGAP1 interaction with MAPK proteins. Similar to previous findings (Brunet et al, 2002 *J Cell Biol* 156:817-828; Matsuzaki et al, 2003 *Proc Natl Acad Sci USA* 100:11285-11290), FOXO1-NESm and FOXO1-NLSm, in which the nuclear exportation signal (NES) or the nuclear localization signal (NLS) is mutated, were primarily localized in the nucleus and the cytoplasm, respectively (FIGS. 7A and B). Consistent with a previous report (Nakamura et al, 2000 *Mol Cell Biol* 20:8969-8982), FOXO1-WT was mainly localized in the cytoplasm in PTEN-null LNCaP cells (FIGS. 7A and B). Co-IP assays demonstrated that ectopic expression of FOXO1-WT and cytoplasmic FOXO1-NLSm largely inhibited IQGAP1 binding to MAPK proteins in these cells (FIG. 5E, and FIG. 6C). In contrast, the inhibitory effect of the nuclear mutant FOXO1-NESm on IQGAP1-MAPK interaction was much less than FOXO1-NLSm and FOXO1-WT (FIG. 5E, and FIG. 6C). Furthermore, a small (30 amino acids) S319 phospho-mimicking IQGAP1-binding peptide of FOXO1 was generated, termed FOXO1-IQBP (S319E) or FOXO1-IQBP (SE), by mutating the serine 319 residue to glutamic acid (E). This peptide and the "wild-type" (S319) and S319A counterparts were ubiquitously expressed in both cytoplasm and nucleus (FIG. 7C). Compared with S319, the S319E mutant had higher affinity of binding to IQGAP1, and a similar result was obtained with another phospho-mimicking mutant S319D in which S319 was mutated to aspartic acid (D) (FIGS. 7D and E). Moreover, in comparison with S319, S319E had much greater inhibitory effect on the interaction between endogenous FOXO1 and IQGAP1 (FIG. 7F). In contrast, IQGAP1-binding affinity of the non-phosphorylatable mutant S319A and its inhibitory effect on FOXO1-IQGAP1 interaction was much lower in comparison with S319 (FIGS. 7D and F). In line with these findings, expression of the S319E peptide had the greatest inhibitory effect on IQGAP1-MAPK interaction, whereas the inhibitory effect of S319A was much smaller (FIG. 5F, and FIGS. 6D and E). Together, AKT-phosphorylated FOXO1 binds to the coiled-coil domain of IQGAP1 and impedes IQGAP1 interaction with MAPK kinase proteins in cells. The observation that c-Raf, MEK and ERK all bind to separate sites downstream of the coiled-coil domain prompted us to test the hypothesis that binding of the short S319E peptide to the coiled-coil region causes conformation changes in IQGAP1, which in turn impair the binding of MAPK proteins to IQGAP1. Limited proteolysis assay is often used to monitor protein conformation changes (Varne et al, 2002 *FEBS Lett*

Figure 7G:
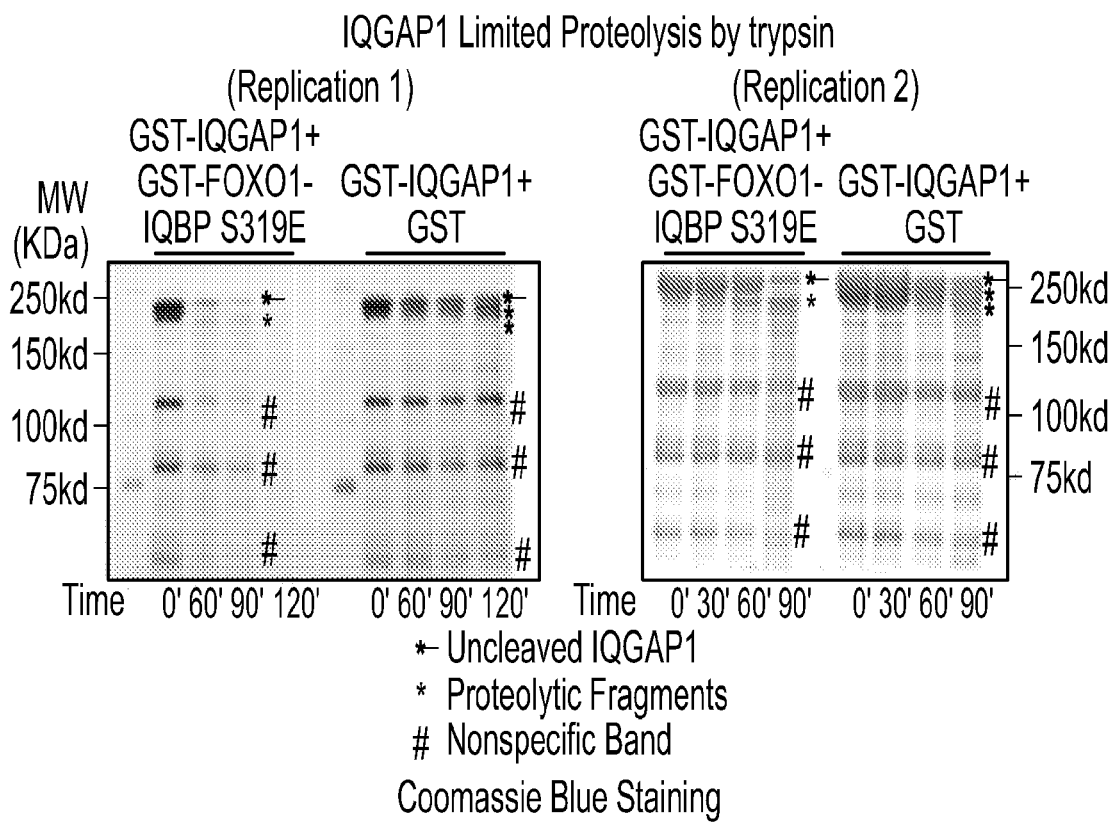

516:129-132). Recombinant IQGAP1 proteins were incubated with GST-FOXO1-IQBP S319E or GST alone and partial digestion of proteins were performed using trypsin. As shown in FIG. 7G, there were two major proteolytic bands migrated slightly faster than the uncleaved IQGAP1 in the control (GST alone) group whereas there was only one major band migrated slightly faster than the uncleaved IQGAP1 in the GST-FOXO1-IQBP S319E group. These data suggested that binding of the short S319E peptide causes conformation changes in IQGAP1 which therefore provide a plausible explanation for the inhibitory effect of this peptide on the binding of c-Raf, MEK and ERK to IQGAP1.

AKT-Phosphorylated FOXO1 Inhibits IQGAP1-Augmented Phosphorylation of ERK1/2

Given that AKT-phosphorylated FOXO1 dampens IQGAP1-MAPK protein interaction, whether FOXO1 regulates phosphorylation and activation of ERK1/2 was determined. Expression of AKT phosphorylation (pAKT) and ERK1/2 phosphorylation (pERK1/2) was examined in a panel of prostate cancer cell lines. As shown in FIG. 8A, pERK1/2 was high in pAKT-undetectable cell lines 22Rv1 and DU145, whereas pERK1/2 was hardly detectable in pAKT-high cell lines LNCaP, C4-2, PC-3, and LAPC-4; thus, there was an inverse relationship between pAKT and pERK1/2 in the cell lines surveyed.

To determine the causal role of FOXO proteins in regulation of pERK1/2, FOXO proteins were overexpressed in DU145, a cell line with high pERK1/2. Similar to FOXO1, FOXO3 and FOXO4 (FOXO6 was not examined because it is primarily expressed in neurons) were also able to interact with IQGAP1 (FIGS. 8B and C), and their interaction with IQGAP1 also depends on AKT phosphorylation at S315 in FOXO3 and S262 in FOXO4, which are homologous to S319 in FOXO1 (FIG. 8D-F). Moreover, ectopic expression of these proteins abrogated pERK1/2 in DU145 cells (FIG. 8G).

Figure 9A:
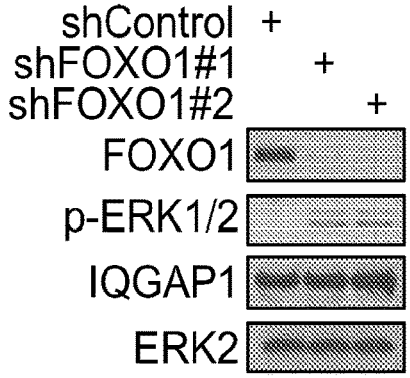
Figure 9B:
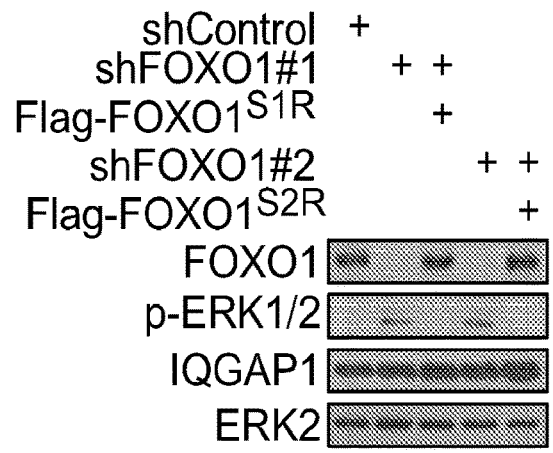
Figure 9C:
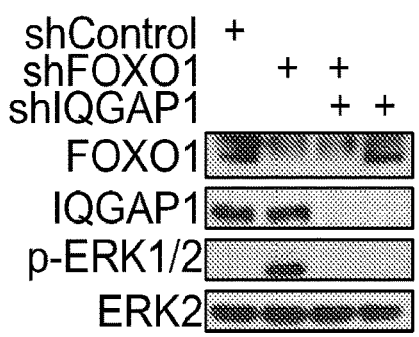
Figure 9D:
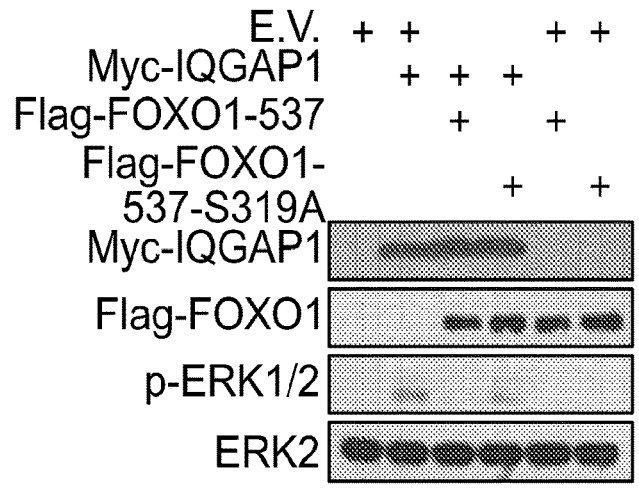
Figure 9E:
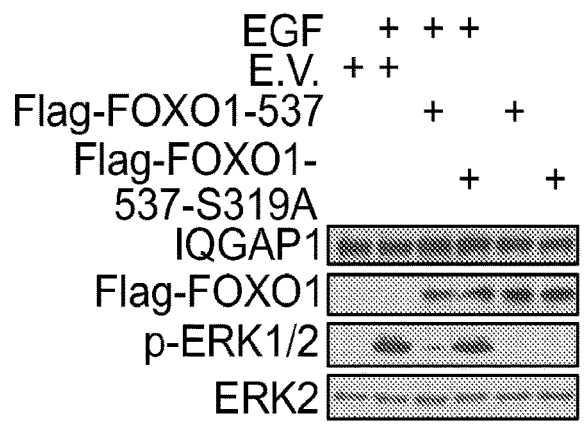
Figure 10A:
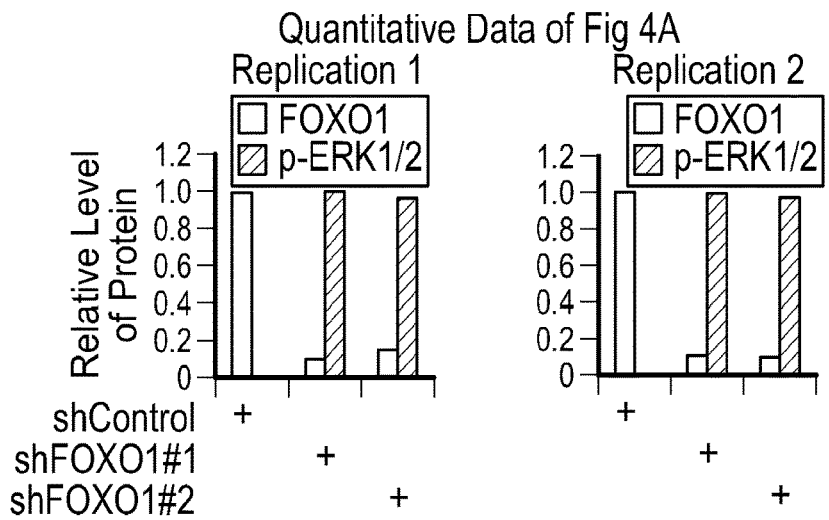
Figure 10B:
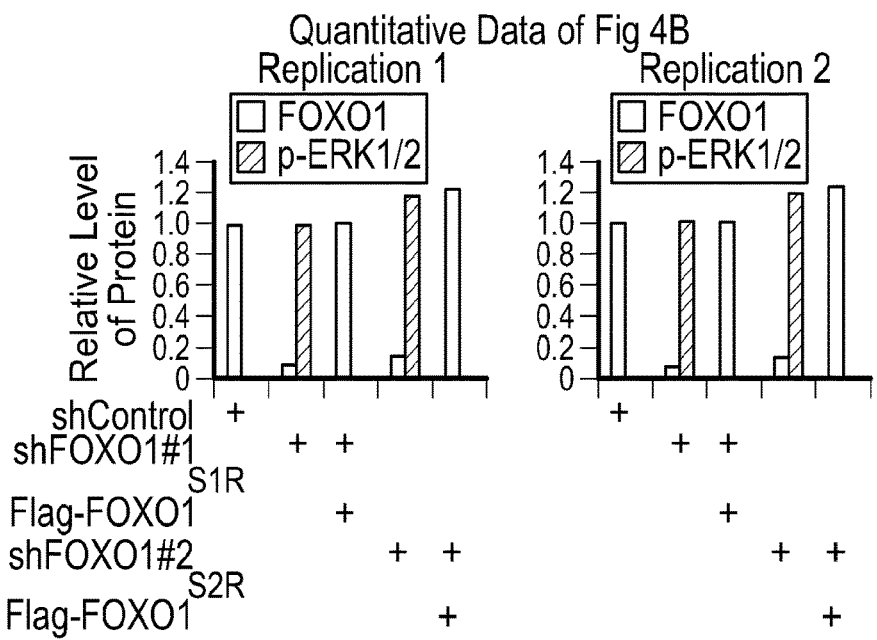
Figure 10C:
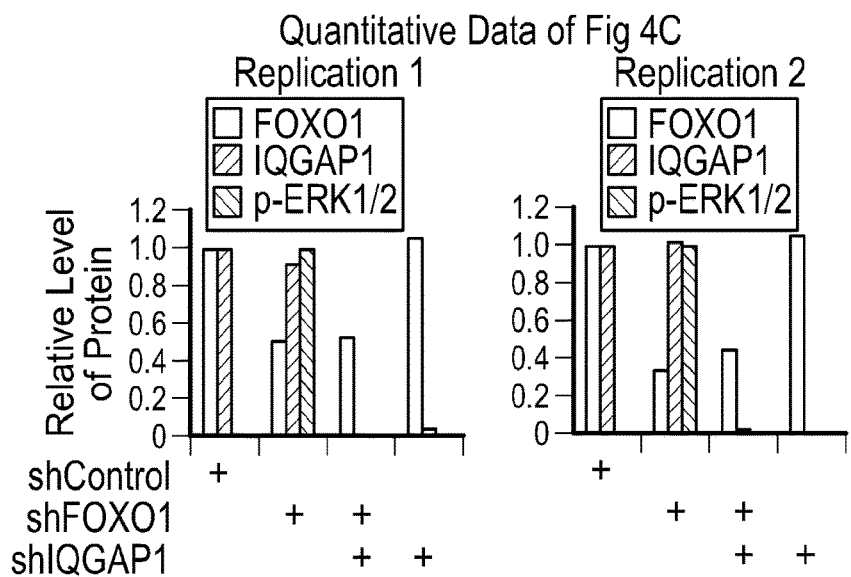
Figure 10D:
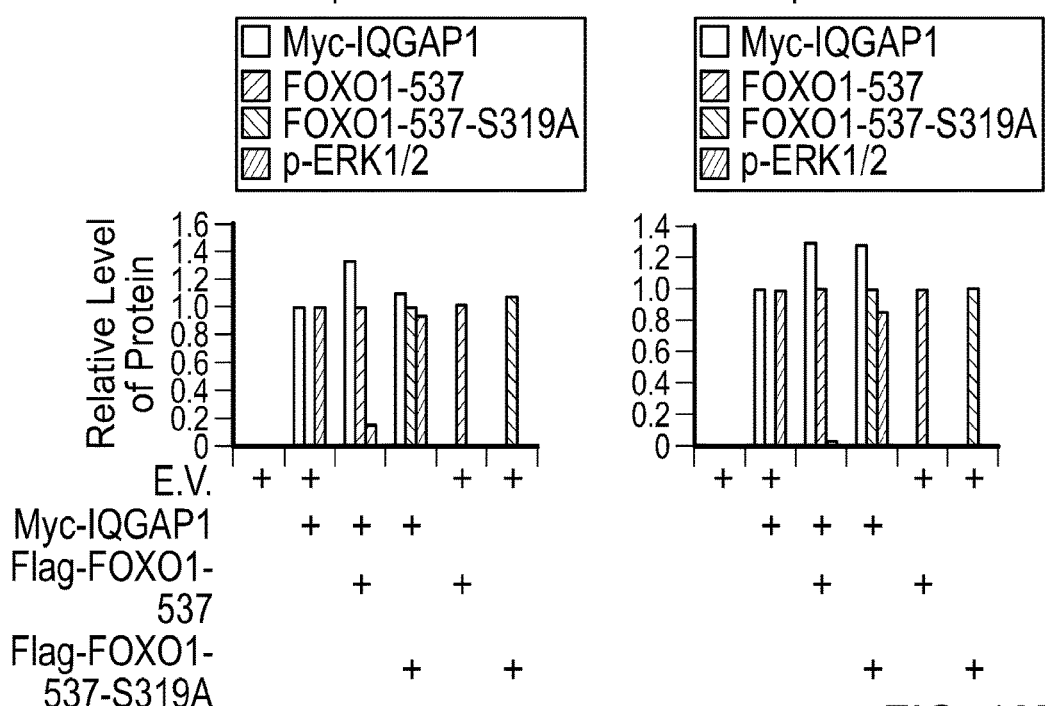
Figure 10E:
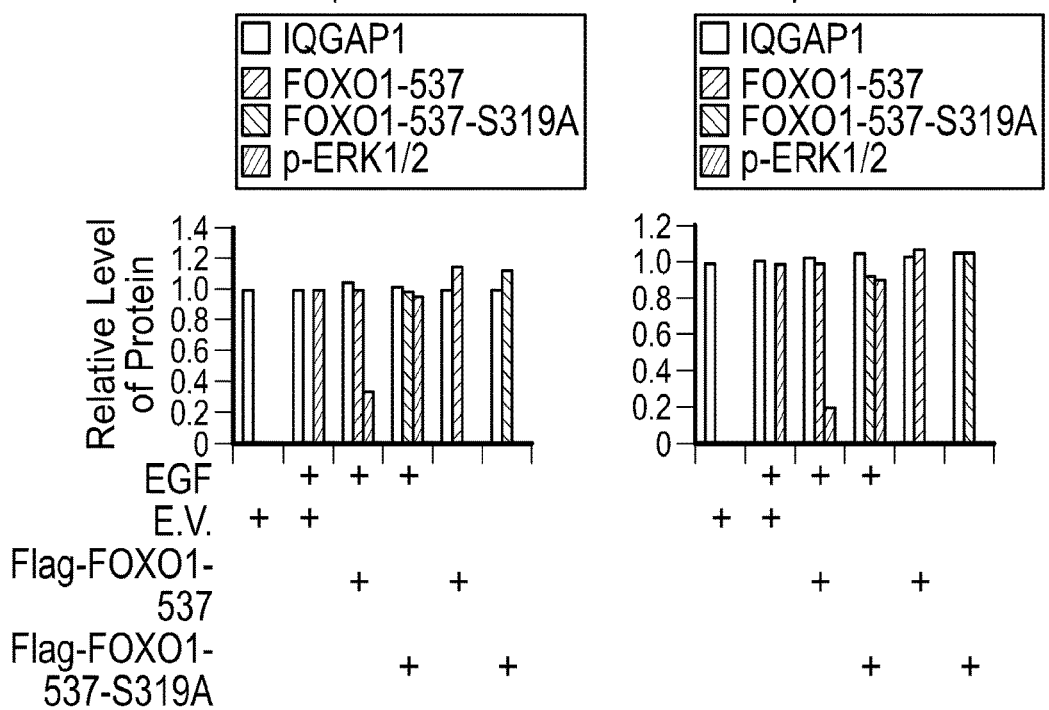

Next, the effect of knockdown of FOXOs in LNCaP, a cell line with little or no basal level of pERK1/2, was examined. Because the expression level of endogenous FOXO4 is extremely low in human prostate cancer cell lines (Huang et al, 2006 Science 314:294-297; Modur et al, 2002 J Biol Chem 277:47928-47937), only FOXO1 and FOXO3 were focused on. Knocking down endogenous FOXO1 by two independent gene-specific short hairpin RNAs (shRNAs) markedly increased pERK1/2 in LNCaP cells, and this was completely reversed by restored expression of shRNA-resistant FOXO1 (FIGS. 9A and B, and FIGS. 10A and B). Knockdown of FOXO3 by two independent shRNAs also increased pERK1/2 (FIG. 8H). Notably, co-knockdown of FOXO1 and FOXO3 resulted in a much greater induction of pERK1/2 in comparison to each individual knockdown alone (FIG. 8I), an indication of a collaborative rather than redundant role of different FOXO factors in regulating pERK1/2. A plausible explanation for this observation is that IQGAP1 is a highly abundant protein and there are likely enough IQGAP1 molecules in cells for FOXO1 and FOXO3 binding. This notion is further supported by the finding that while cytoplasmic FOXO1 proteins in LNCaP cell lysate were completely pulled down by anti-FOXO1 antibody used, approximately 70% of IQGAP1 was pulled down by the same antibody (FIG. 8J). Importantly, FOXO1 knockdown-induced increase in pERK1/2 was completely reversed by concomitant knockdown of endogenous IQGAP1 (FIG. 9C, and FIG. 10C). Similar results were obtained in other cancer types such as pancreatic cancer cell lines PANC-1 and MIA-PaCa-2 (FIG. 8K). These data suggested that the effect of FOXO1 on pERK1/2 is mediated through IQGAP1. Conversely, overexpression of IQGAP1 increased pERK1/2 in C4-2 cells (FIG. 9D, and FIG. 10D). This effect was largely diminished in cells transfected with FOXO1-537 but not the non-phosphorylatable mutant FOXO1-537 S319A (FIG. 9D, and FIG. 10D), a finding highlighting the importance of S319 phosphorylation in FOXO1 regulation of pERK1/2. Finally, epidermal growth factor treatment induced pERK1/2 in C4-2 cells, whereas this effect was largely abolished by ectopic expression of FOXO1-537 but not the S319A mutant (FIG. 9E, and FIG. 10E). Together, these findings demonstrated that AKT-phosphorylated FOXO1 inhibits pERK1/2 in a transactivation-independent manner and this effect is mediated through IQGAP1.

Figure 9F:
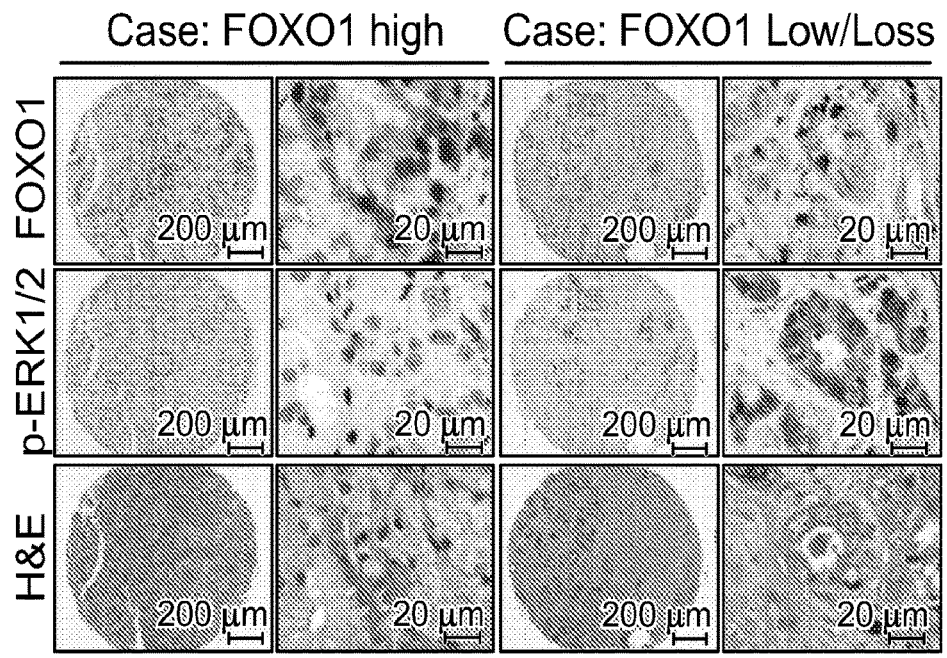
Figure 9G:
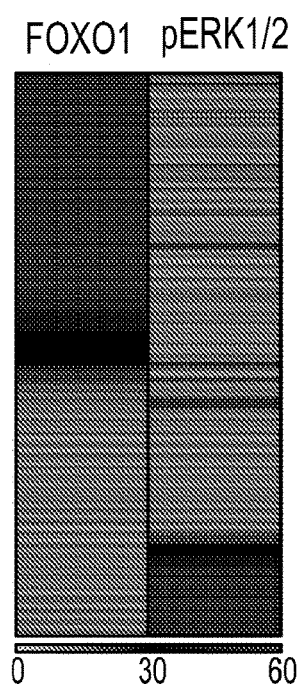
Figure 9H:
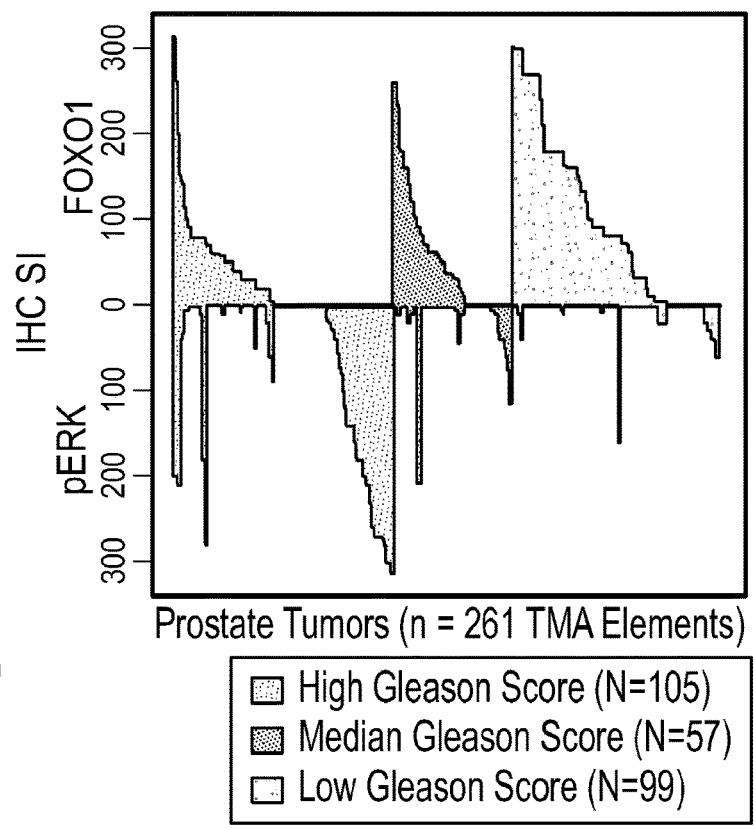

Expression of FOXO1 and pERK1/2 Inversely Correlates in Prostate Cancer Specimens FOXO1 is partially deleted or transcriptionally downregulated in approximately 35% of human prostate cancer cell lines and patient samples (Dong et al, 2006 Cancer Res 66:6998-7006; Haflidadottir et al, 2013 PLoS One 8:e72400; Modur et al, 2002 J Biol Chem 277:47928-47937). To explore the clinical relevance of FOXO1-mediated inhibition of pERK1/2, whether expression of FOXO1 and pERK1/2 correlate in human prostate cancer specimens was determined. The expression of these two proteins was examined immunohistochemically on a tissue microarray (TMA) containing a cohort of prostate cancer samples (n=261 TMA specimens) obtained from 167 patients. Immunohistochemical staining was evaluated by measuring both percentage of positive cells and staining intensity. Representative images of high and low/no staining of FOXO1 and pERK1/2 and corresponding hematoxylin-eosin staining are shown in FIG. 9F. FOXO1 was inversely correlated with pERK1/2 expression in this cohort of patients (Spearman $\rho=-0.29$, $P=2.6\times 10-6$) (FIG. 9G). Further analysis indicated that tumors with lower Gleason scores have high FOXO1 expression and FOXO1 expression was negatively associated with Gleason score (Spearman $\rho=-0.35$, $P=1.0\times 10-8$). In contrast, tumors with higher Gleason scores had high pERK1/2 levels, which were positively associated with Gleason score (Spearman $p=0.32$, $P=1.4\times 10-7$) (FIG. 9H). These data indicate that loss or reduced expression of FOXO1 correlates with pERK1/2 and prostate cancer progression, at least in a subset of patients.

Nuclear Localization of FOXO1 Promotes PI3K/AKT Inhibition-Induced pERK1/2

Figure 11A:
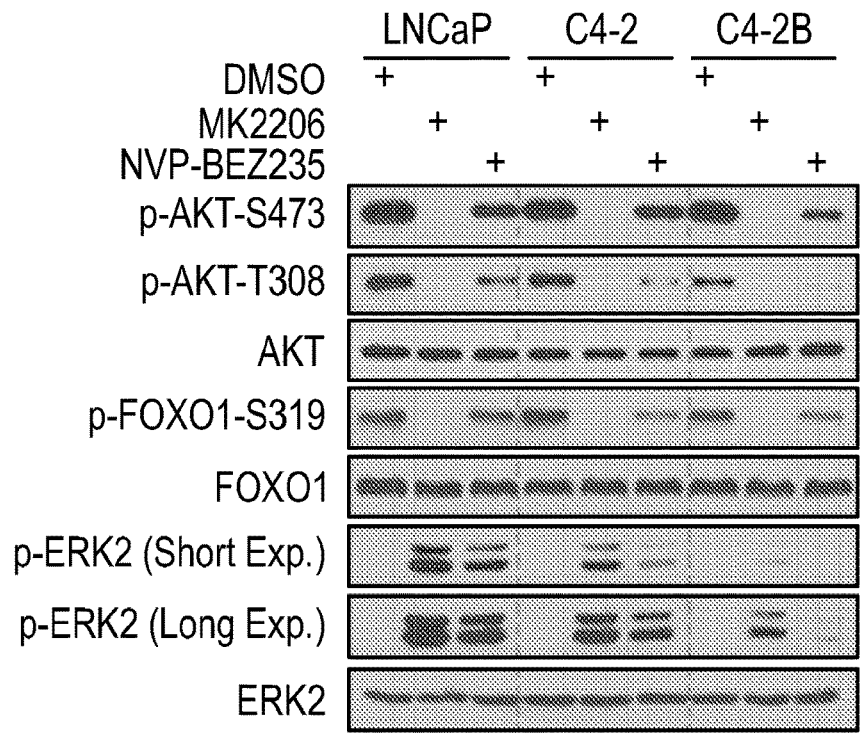
Figure 12A:
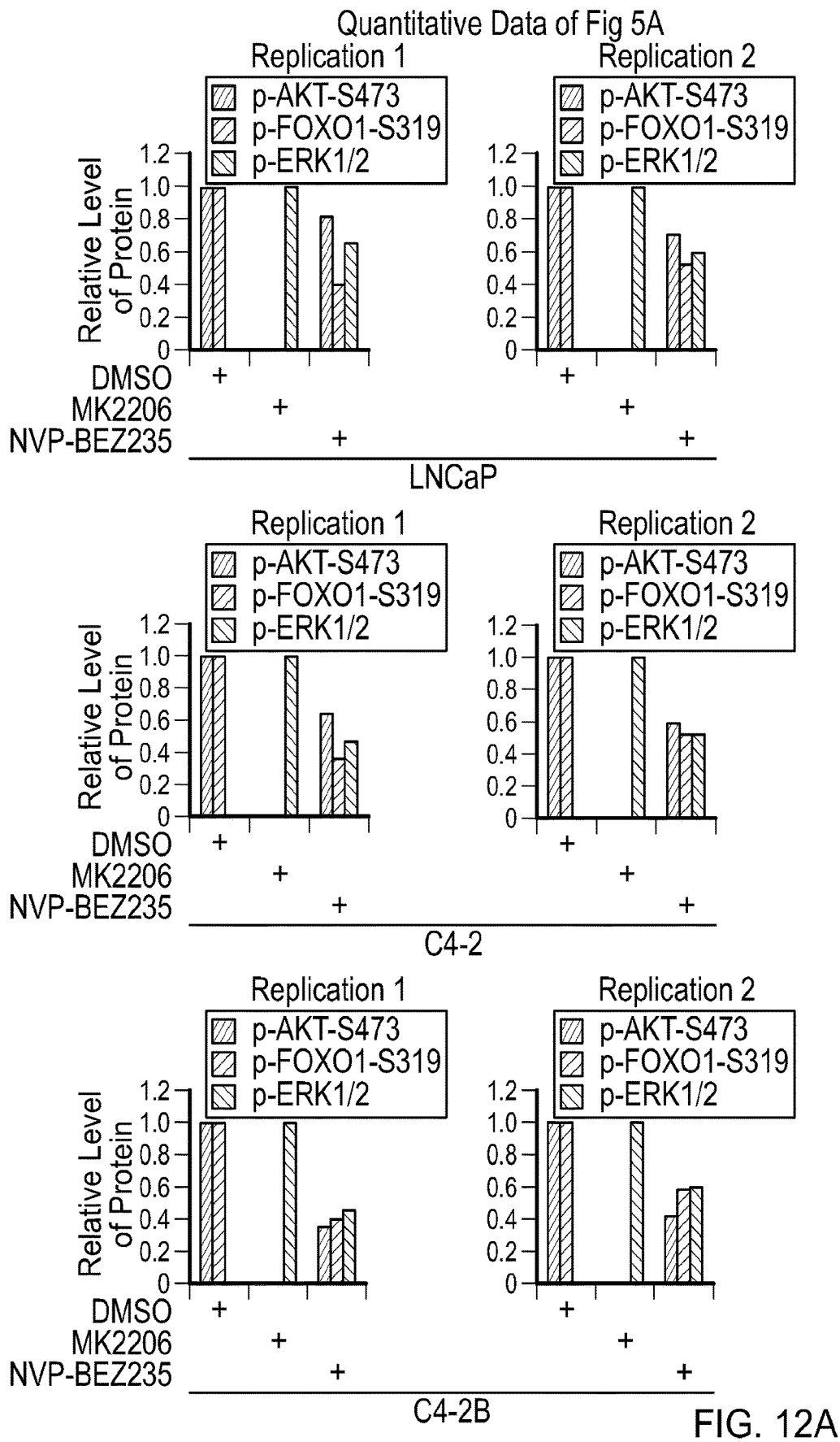

As demonstrated in other cancer types such as breast, pancreatic, and nasopharyngeal, among others, inhibition of the PI3K-AKT pathway often results in an increase in pERK1/2 (Chandarlapaty et al, 2011 Cancer Cell 19:58-71; Moelling et al, 2002 J Biol Chem 277:31099-31106; Robertson et al, 2010 Mol Cancer 9:260; Serra et al, 2011 Oncogene 30:2547-2557). That inhibition of pAKT by the AKT inhibitor MK2206 increased pERK1/2 was demonstrated in PTEN-null prostate cancer cell lines LNCaP, C4-2, and C4-2B (FIG. 11A and FIG. 12A). A similar result was obtained by administering the PI3K/mTOR dual inhibitor NVP-BEZ235 in LNCaP cells, but its effect was very limited in C4-2 and almost none in C4-2B cells. The different effects of NVP-BEZ235 in these cell lines were not due to the differences in IQGAP1 expression (FIG. 13A), and the precise underlying mechanism warrants further investigation.

Figure 11B:
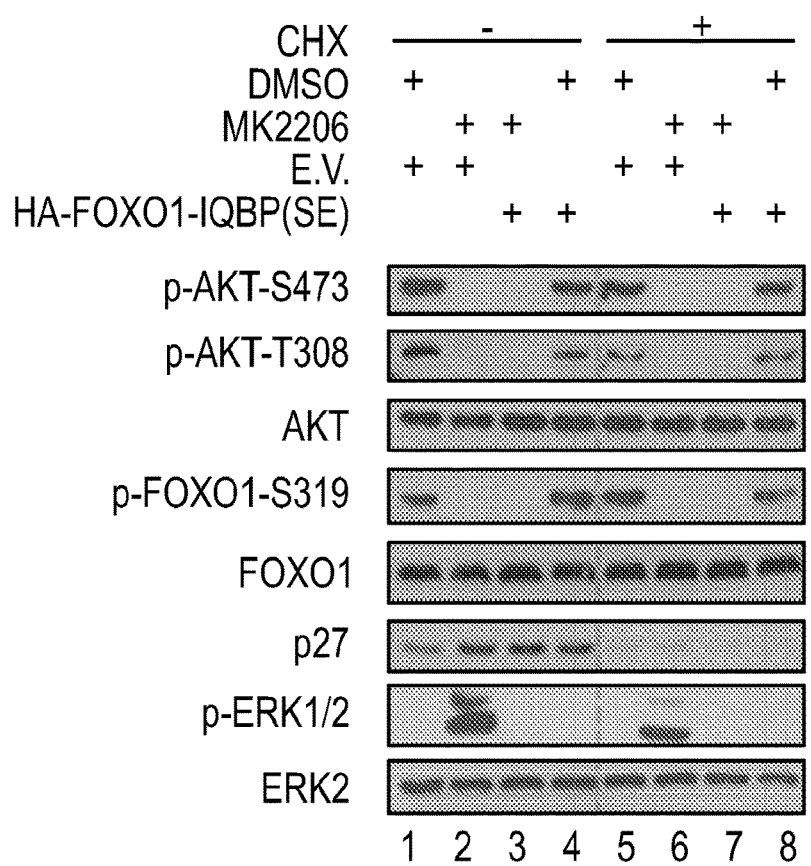
Figure 12B:
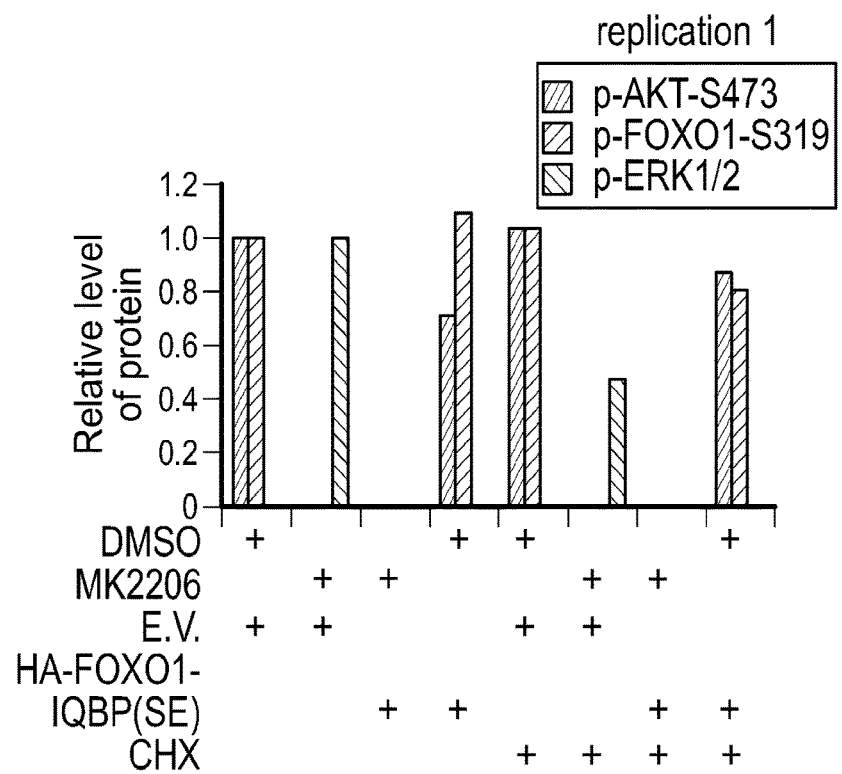
Figure 12B:
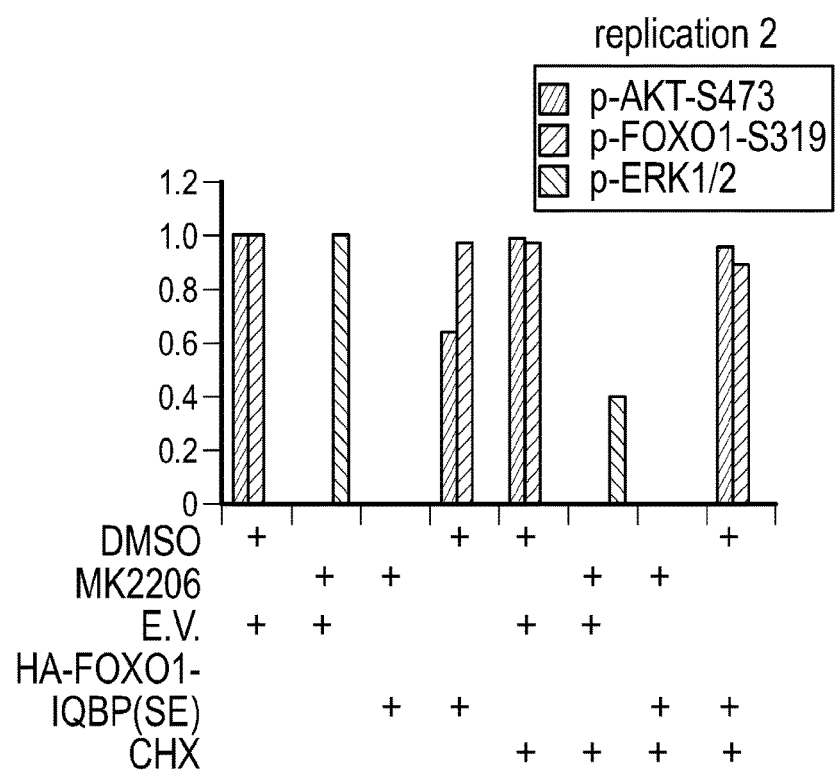
Figure 13B:
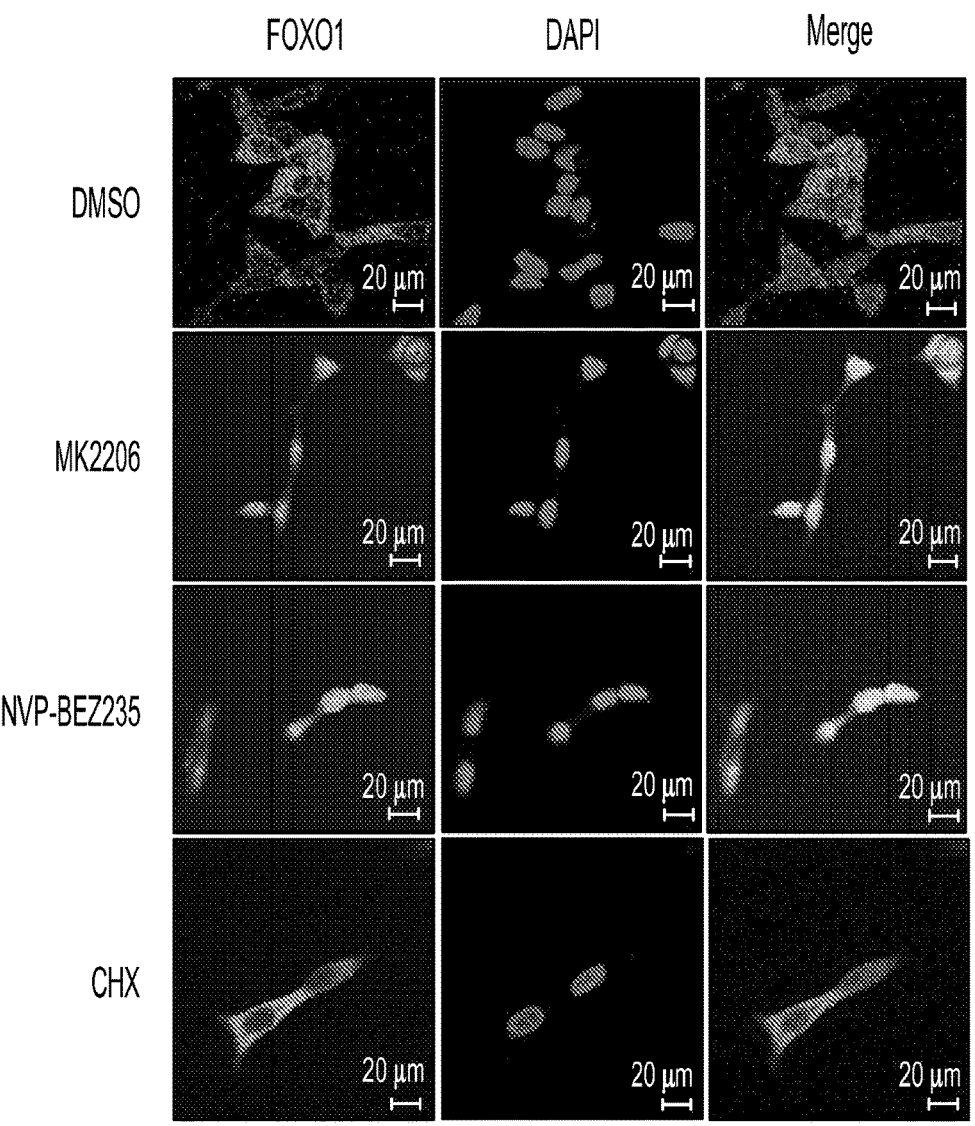

In breast cancer cells, treatment with PI3K or AKT inhibitor increases pERK1/2 by inducing nuclear localization of FOXO and FOXO-dependent transcription of receptor tyrosine kinase genes such as HER3 (Chandarlapaty et al, 2011 Cancer Cell 19:58-71; Serra et al, 2011 Oncogene 30:2547-2557). As expected, MK2206 or NVP-BEZ2235 also induced nuclear localization of FOXO1 in LNCaP cells (FIG. 13B). Surprisingly, treating LNCaP cells with the protein synthesis inhibitor cycloheximide (CHX) resulted in only approximately 50% reduction in MK2206-induced pERK1/2 (FIG. 11B, lane 2 versus 6, and FIG. 12B). The effectiveness of CHX was evident by the blockage of induction of p27KIP1, a well-studied FOXO transactivation target (FIG. 11B, lane 1, 2 versus 5, 6). No effect of CHX treatment alone on pERK1/2 and FOXO1 nuclear localization was detected (FIG. 11B, lane 1 versus 5, FIG. 13B, and FIG. 12B). These data indicated the existence of FOXO transcription-independent pathways responsible for PI3K/AKT inhibition-induced pERK1/2.

Figure 11C:
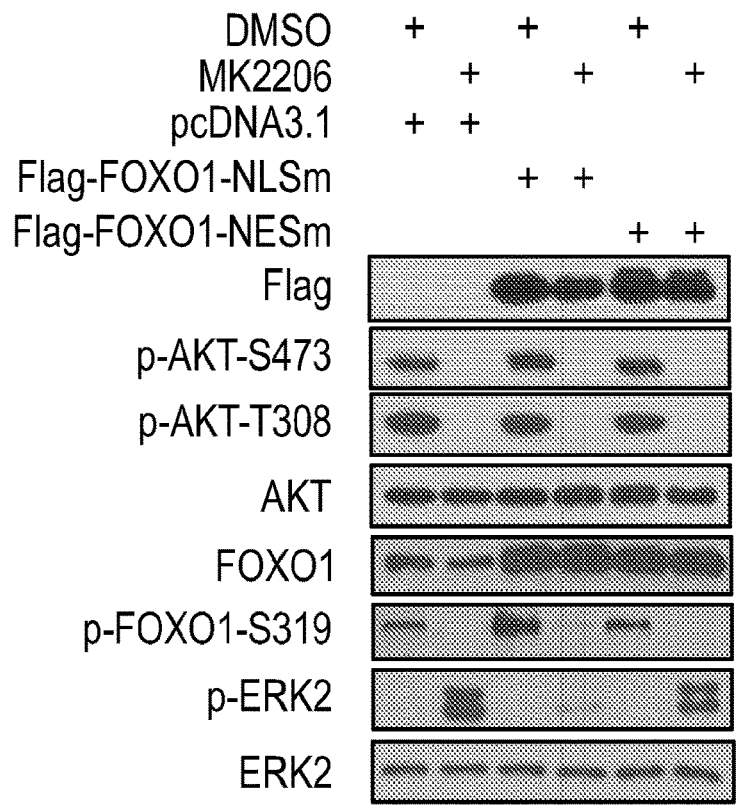
Figure 12C:
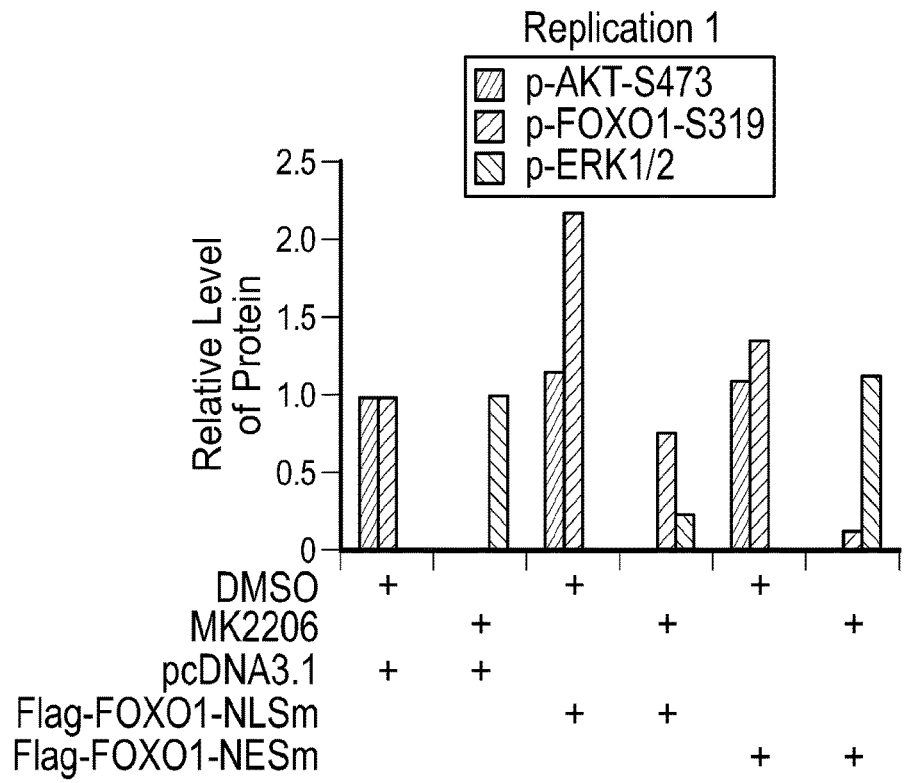
Figure 12C:
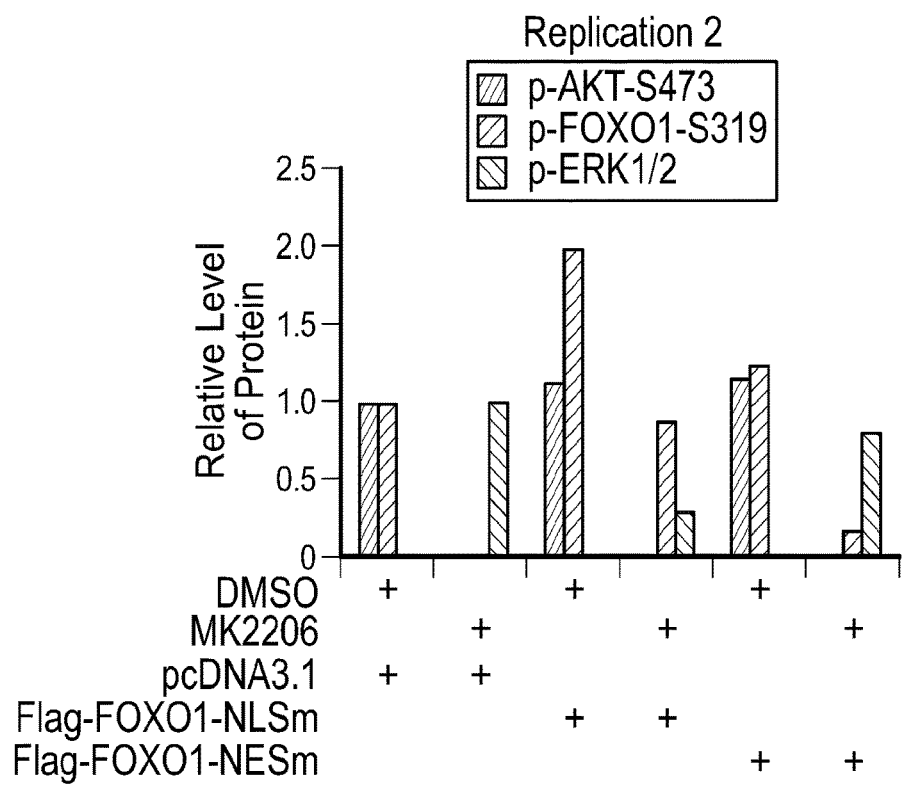

These results prompted us to test if AKT inhibition promotes FOXO1 nuclear localization, which in turn results in dismissal of FOXO1-mediated inhibition of IQGAP1 in the cytoplasm and subsequent IQGAP1-dependent hyperactivation of ERK1/2. This possibility is supported by the finding that forced expression of FOXO1-NLSm, a cytoplasmic mutant, but not the nuclear mutant FOXO1-NESm, largely inhibited MK2206-induced pERK1/2 in LNCaP cells (FIG. 11C, FIGS. 7A and B, and FIG. 12C). Thus, loss of inhibition of IQGAP1 by cytosolic FOXO1 represents a crucial mechanism that drives PI3K/AKT inhibitor-induced ERK1/2 activation.

Figure 11D:
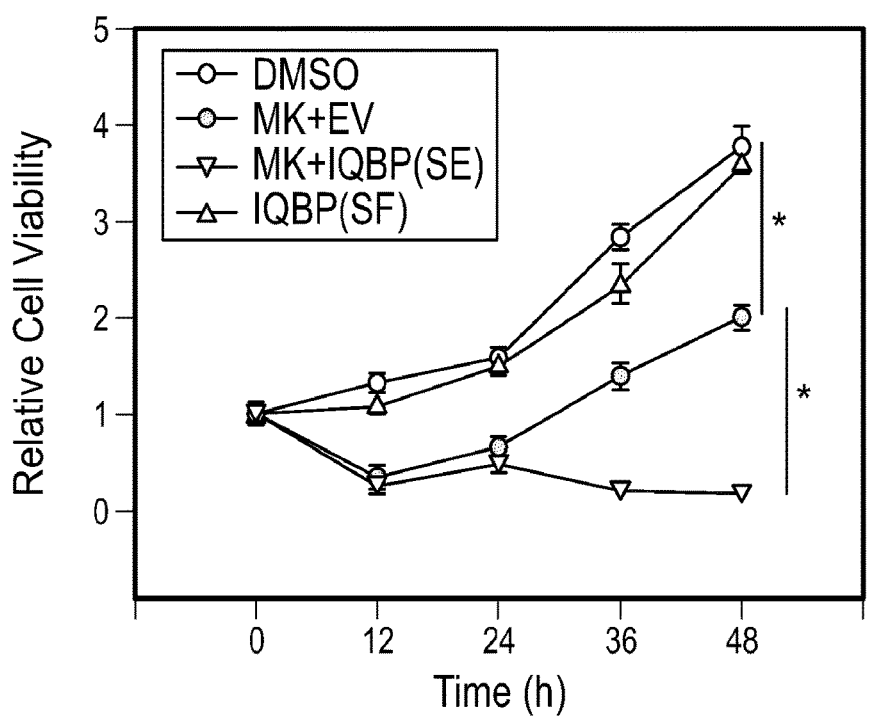
Figure 14A:
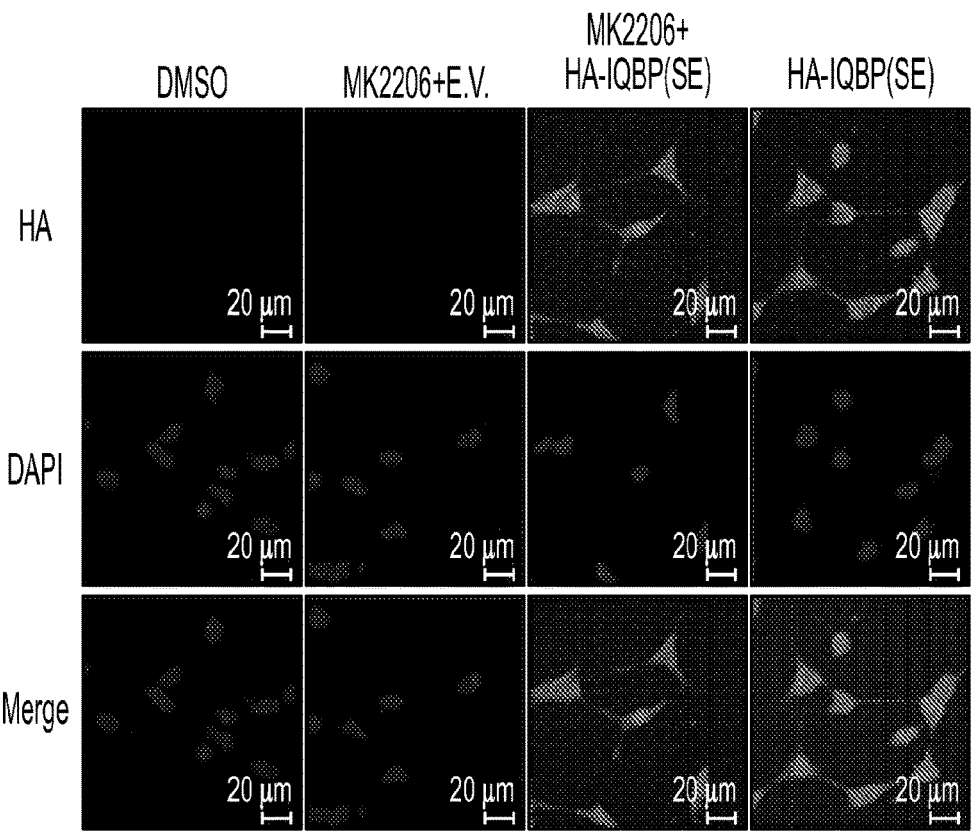
Figure 14B:
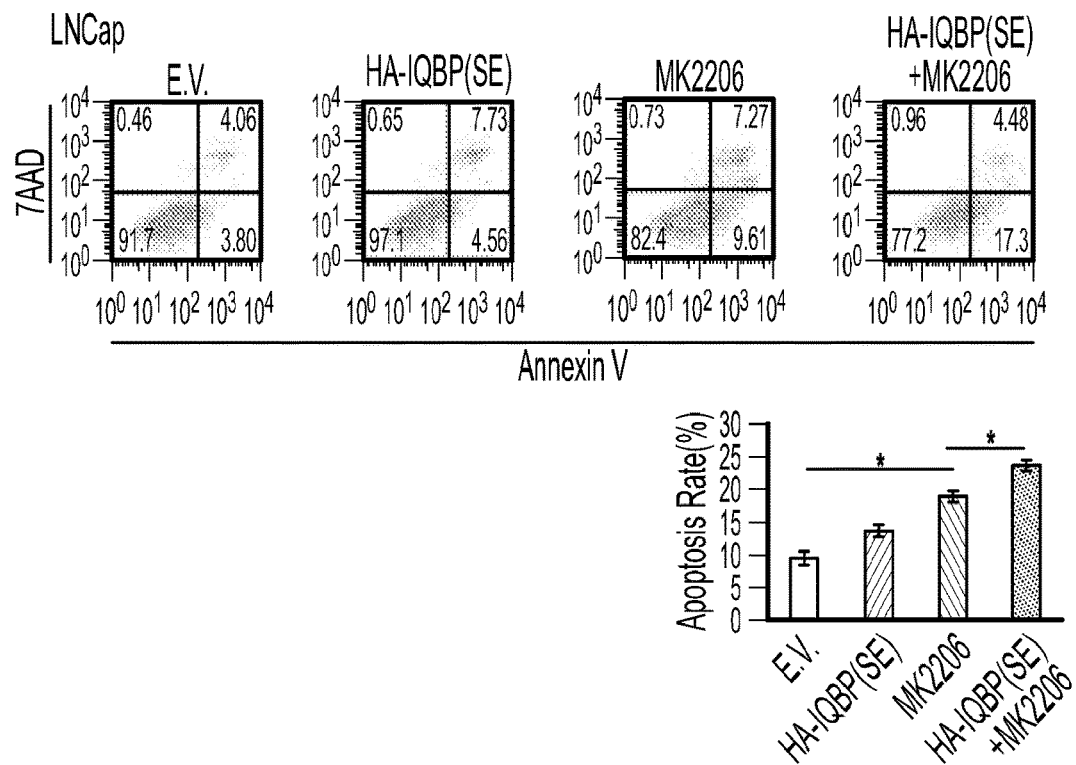
Figure 14C:
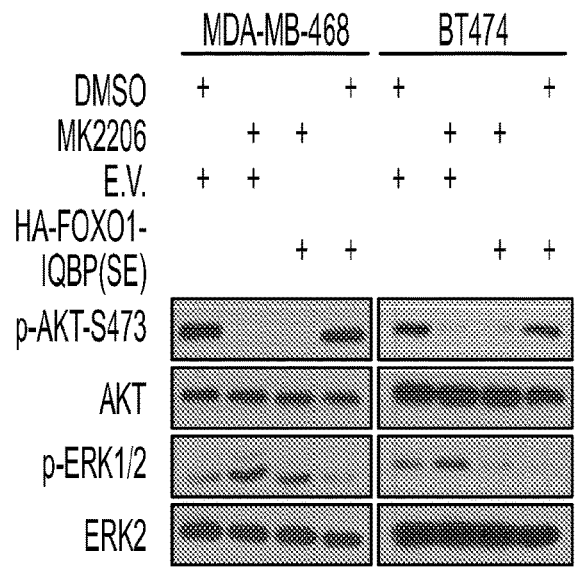

As demonstrated in FIG. 5F, expression of FOXO1-IQBP (S319E or SE), a FOXO1-derived phospho-mimicking peptide, impairs the IQGAP1-MAPK interaction. The extent to which expression of this peptide affects IQGAP1-dependent activation of ERK1/2 was examined in PI3K/AKT inhibitor-treated cells. Ectopic expression of FOXO1-IQBP(SE) completely abolished MK2206-induced increase in pERK1/2 in LNCaP cells (FIG. 11B, lane 2 versus 3; 6 versus 7, FIG. 14A, and FIG. 12B). Accordingly, MTS cell viability assays demonstrated that, whereas MK2206 treatment alone only transiently decreased LNCaP cell growth, MK2206 and FOXO1-IQBP(SE) co-treatment completely inhibited cell growth (FIG. 11D). Annexin V staining showed that more cells underwent apoptosis when treated with both MK2206 and FOXO1-IQBP(SE) compared with cells treated with each agent alone (FIG. 14B). Expression of FOXO1-IQBP (SE) also diminished MK2206-induced increase in pERK1/2 in breast cancer cell lines MDA-MB-468 and BT474 (FIG. 14C). These data indicated that a small FOXO1-derived phospho-mimicking peptide can enhance AKT inhibitor-induced cell death by overcoming acquired ERK1/2 activation.

Figure 11E:
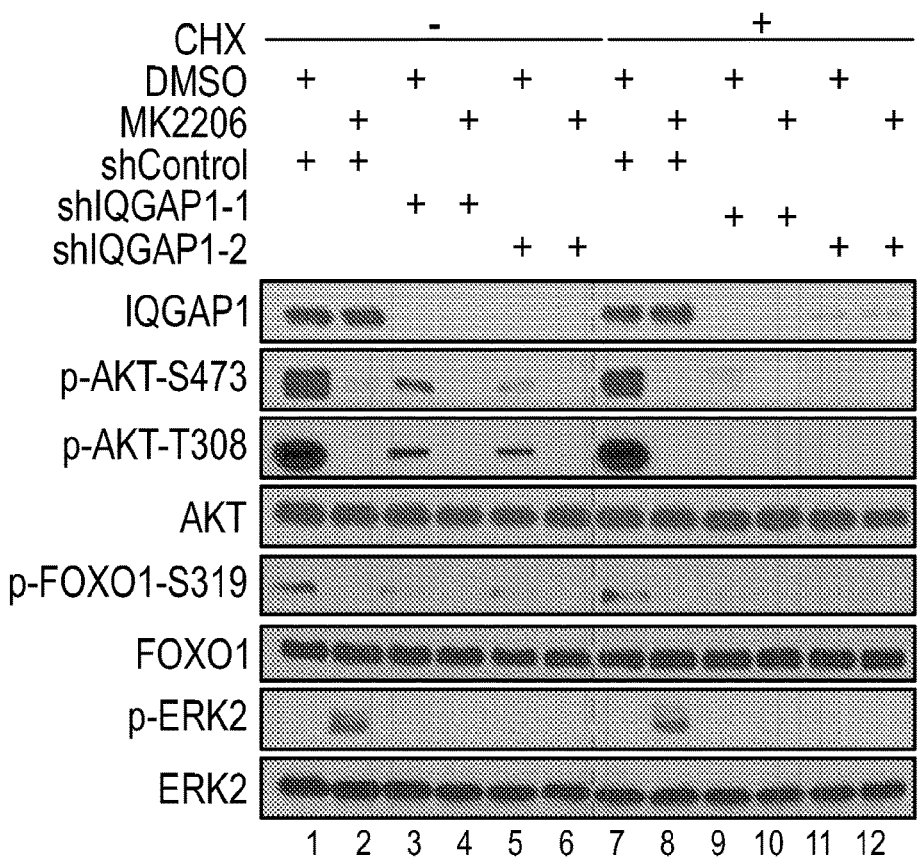
Figure 11F:
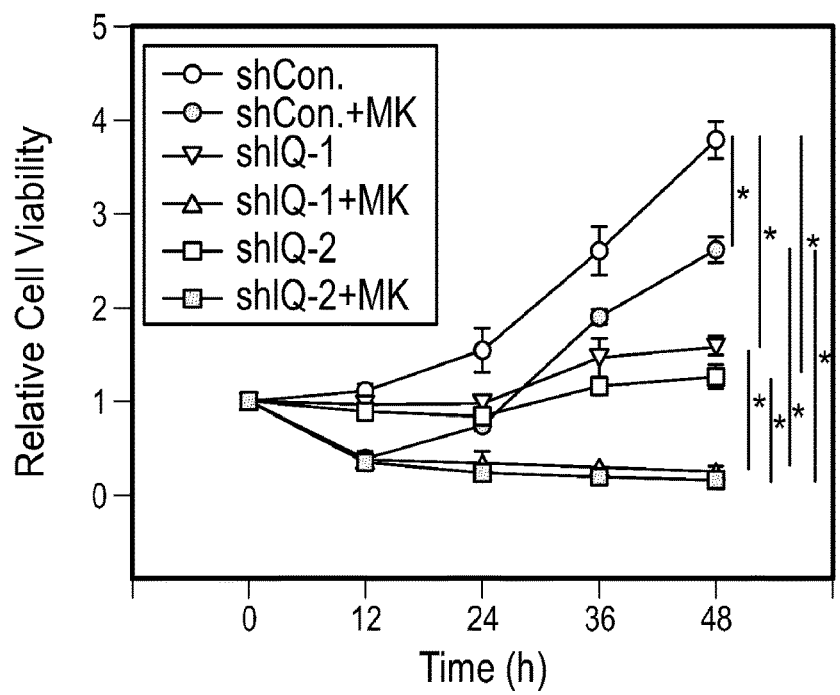
Figure 12D:
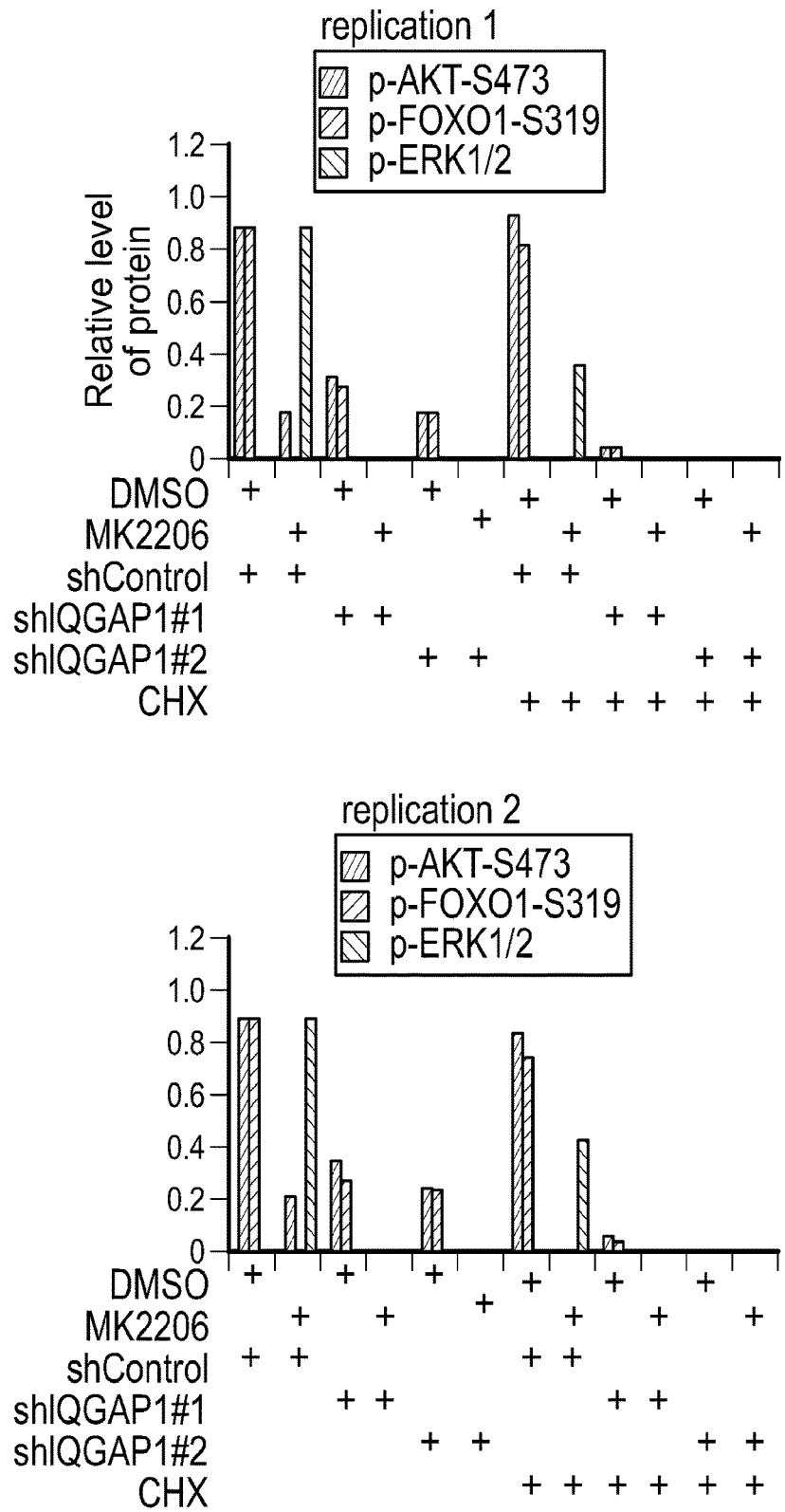
Figure 14D:
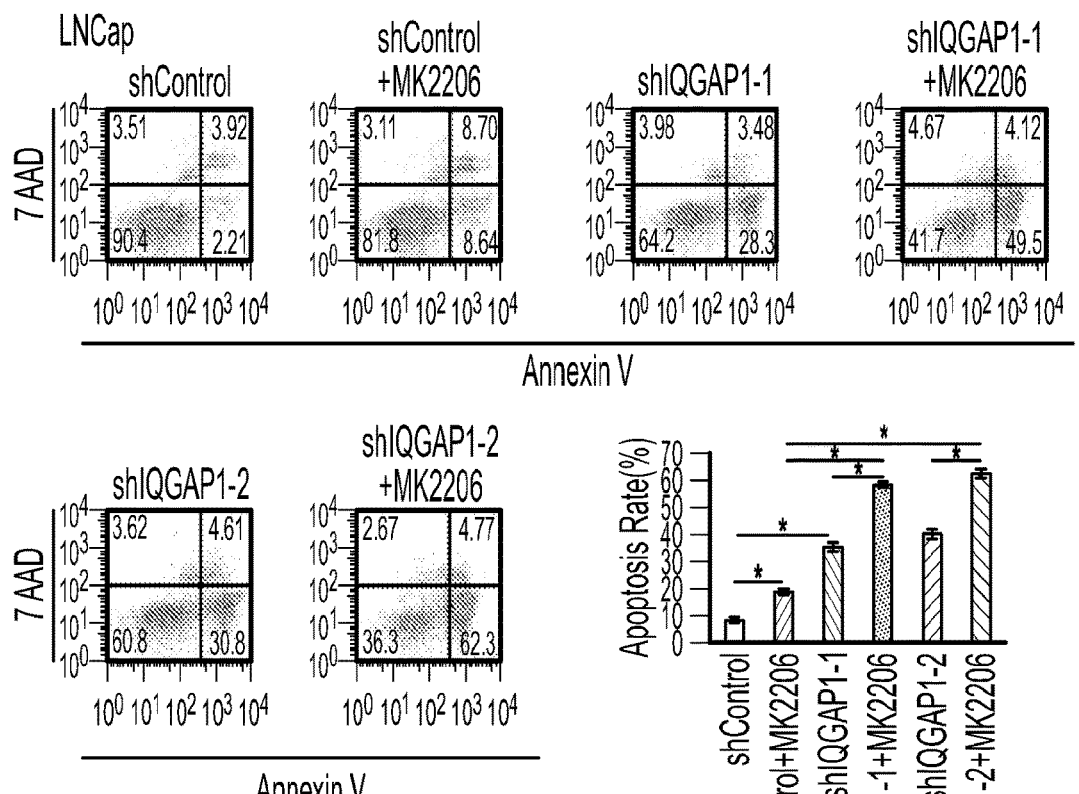

To examine the causal role of IQGAP1 in AKT inhibition-mediated ERK activation, endogenous IQGAP1 was knocked down using two independent shRNAs before MK2206 treatment. IQGAP1 knockdown decreased pAKT at both serine 308 and 473 in LNCaP cells (FIG. 11E, lane 3, 5, 9, 11, and FIG. 12D), which is consistent with the previous report in other cell types (Chen et al, 2010 Exp Mol Med 42:477-483). Different from the treatment of MK2066 alone, however, IQGAP1 knockdown did not trigger the elevation of pERK1/2 while decreasing pAKT (FIG. 11E, and FIG. 12D). This result further indicated the importance of IQGAP1 in AKT inhibition-caused ERK1/2 activation. Depletion of IQGAP1 completely abolished MK2206-induced pERK1/2 regardless of treatment with CHX (FIG. 11E, lane 2 versus 4 and 6; lane 8 versus 10 and 12, and FIG. 12D). Accordingly, co-treatment of LNCaP cells with MK2066 and IQGAP1 shRNAs resulted in greater inhibition of cell growth than MK2066 alone (FIG. 11F). As demonstrated by Annexin V staining, MK2206 treatment plus IQGAP1 knockdown induced a much higher percentage of apoptosis than each agent alone (FIG. 14D). Collectively, these data suggested that the FOXO1-IQGAP1 signaling axis plays an essential role in regulating AKT inhibition-induced activation of ERK and drug resistance in cells.

Figure 16F:
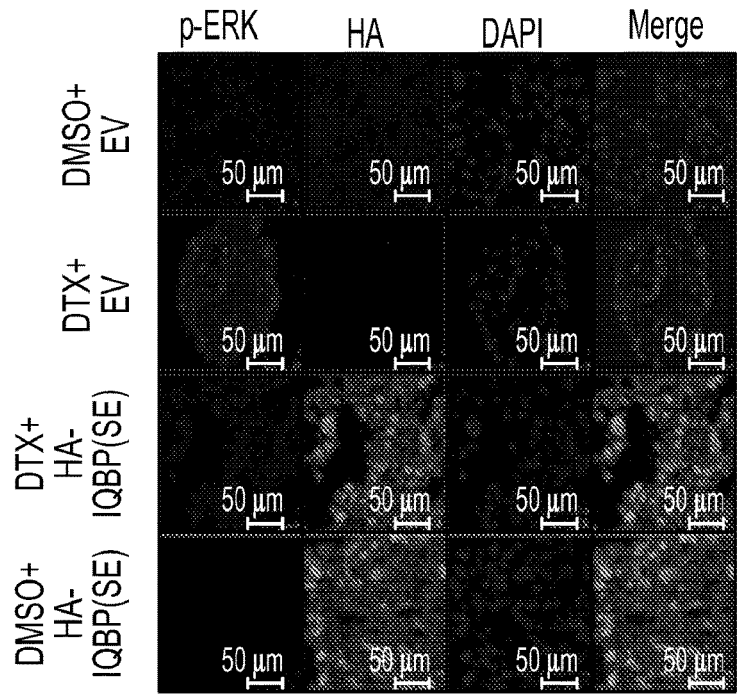
Figure 16G:
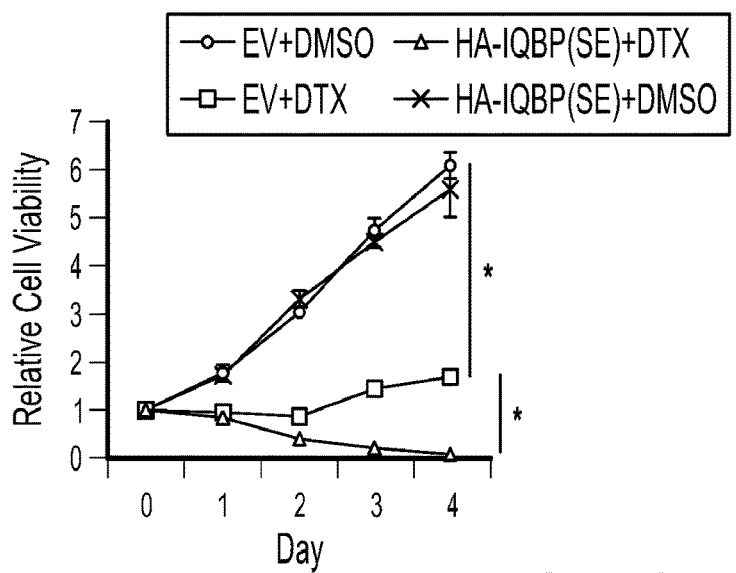
Figure 17A:
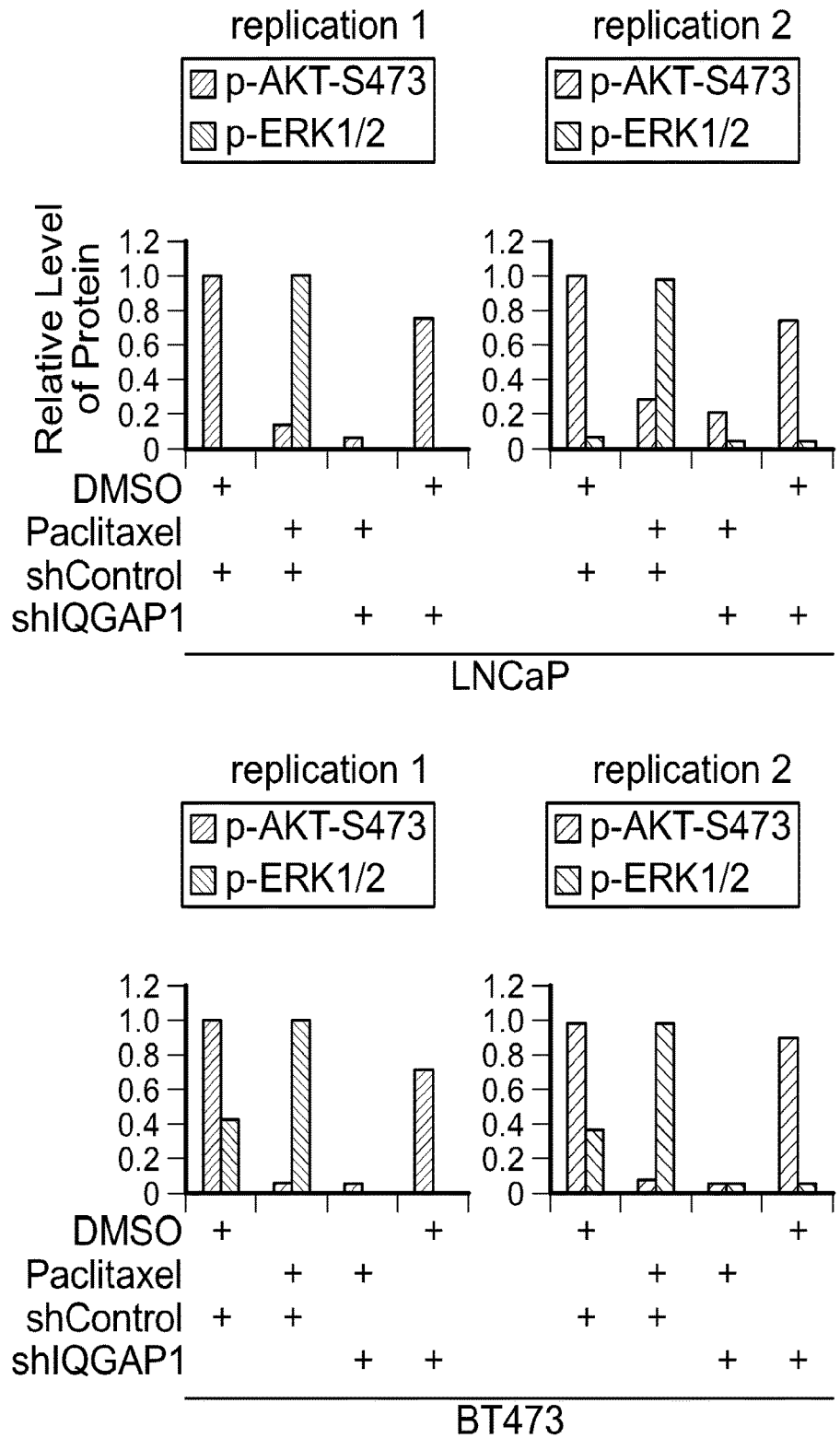
Figure 17B:
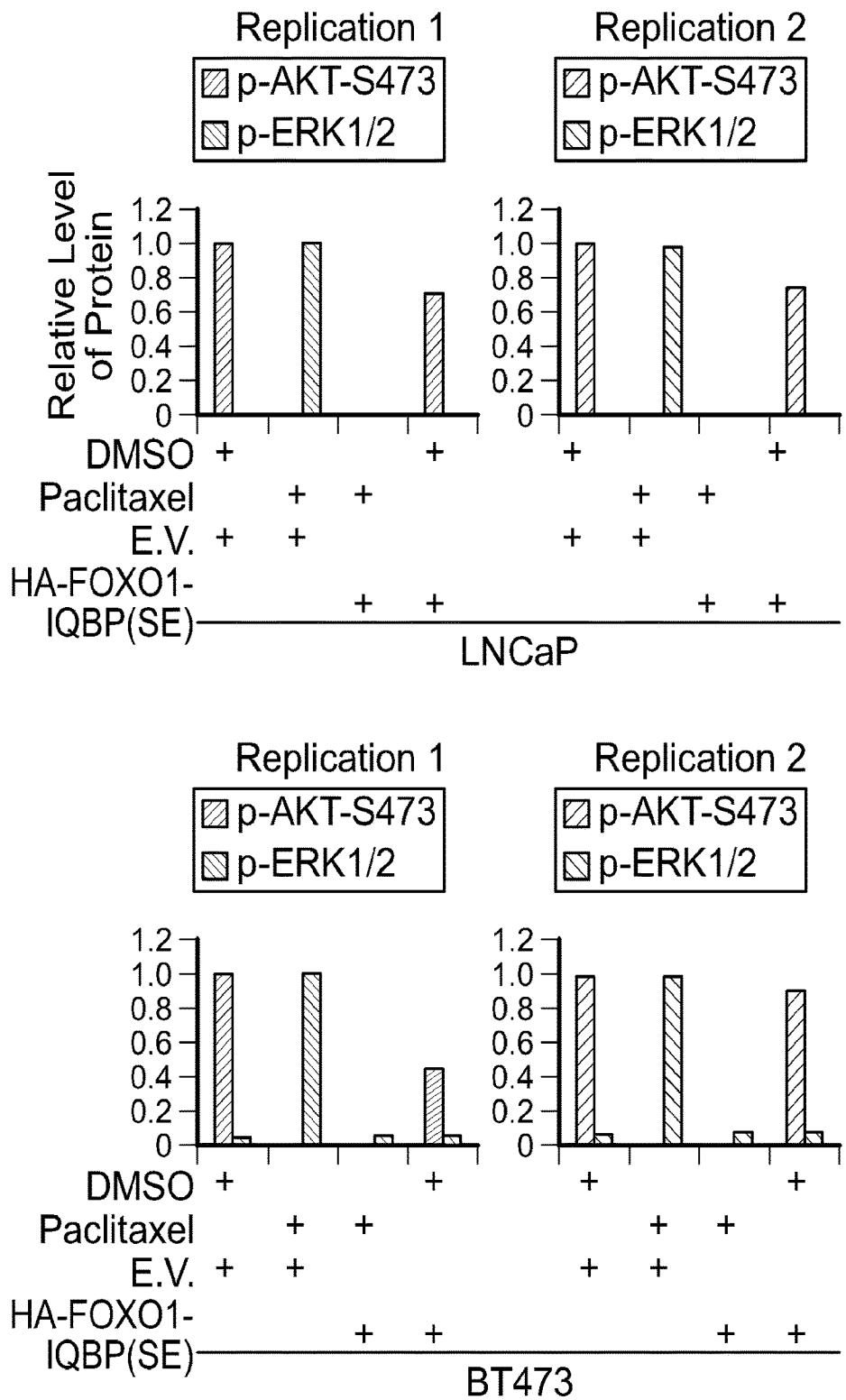

A Small FOXO1-Derived Phospho-Mimicking Peptide Inhibitor Impedes Taxane-Induced ERK Activation and Chemoresistance Paclitaxel and its semisynthetic analogue docetaxel (DTX) are widely used chemotherapeutic agents for treatment of solid tumors. In both preclinical and clinical settings, paclitaxel treatment is well documented to result in activation of the Ras-Raf-MAPK pathway, which confers resistance to paclitaxel (Mehnert et al, 2011 Mol Cancer Ther 10:1509-1519; Okano & Rustgi, 2001 J Biol Chem 276:19555-19564; Sunters et al, 2006 Cancer Res 66:212-220). However, the mechanism underlying paclitaxel-induced MAPK kinase activation remains poorly understood. Paclitaxel induces nuclear localization of FOXO proteins in various types of human cancer (Gan et al, 2009 Cancer Res 69:8386-8394; Goto et al, 2008 Br J Cancer 98:1068-1075; Sunters et al, 2006 Cancer Res 66:212-220). If taxane promotes pERK was tested by inducing nuclear localization of FOXO1 and thereby abolishing FOXO1-mediated inhibition of IQGAP1-dependent activation of MAPK kinases in the cytoplasm. In agreement with the finding in MCF-7 breast cancer cell line (Sunters et al, 2006 Cancer Res 66:212-220), paclitaxel treatment alone induced inhibition of pAKT, decreased phosphorylation of the 14-3-3 binding sites (T24 and S256) responsible for cytoplasmic retention of FOXO1, nuclear localization of FOXO1, and transactivation of p27KIP1 in PTEN-mutated LNCaP prostate cancer and PIK3α-mutated BT474 breast cancer cells (FIG. 15A, FIGS. 16A and B, and FIG. 17A). Paclitaxel treatment also resulted in an increase in pERK1/2 in these cell lines (FIG. 15A, and FIG. 17A). Similar results were obtained in LNCaP and PC-3 cells treated with DTX (FIGS. 16C and D). Moreover, knockdown of endogenous IQGAP1 completely abolished paclitaxel-induced pERK1/2 in both LNCaP and BT474 cell lines without an overt impact on p27KIP1 expression (FIG. 15A, lane 2 versus 3; 6 versus 7, and FIG. 17A). These data suggested that exclusion of FOXO1 in the cytoplasm and subsequent ablation of FOXO1-mediated suppression of IQGAP1-MAPK kinase interaction are responsible for paclitaxel-induced ERK1/2 activation. Given that expression of the small FOXO1-derived peptide FOXO1-IQBP1(SE) antagonizes AKT inhibition-induced ERK1/2 activation (FIG. 11B), whether it can overcome taxane-resistance was examined in vitro and in vivo. Expression of FOXO1-IQBP1(SE) blocked taxane-induced ERK1/2 activation in LNCaP, PC-3, and BT474 cells without affecting pAKT and p27KIP1 expression (FIG. 15B, FIGS. 16C and D, and FIG. 17B). Similar to the results in PC-3 cells cultured in vitro (FIG. 16D), DTX treatment increased pERK1/2 in PC-3 xenografts in mice (FIG. 16F). This result was consistent with the observation that DTX treatment failed to completely block tumor growth in vitro and in vivo (FIGS. 15C-E, and FIG. 16G). In contrast, co-treatment with DTX and FOXO1-IQBP(SE) not only blocked pERK1/2 but also inhibited cancer cell growth in culture and in mice (FIG. 15C-E, and FIG. 16G). Thus, a small bioactive FOXO1-derived peptide inhibitor that overcomes chemoresistance in cancer cells by blocking taxane-induced ERK1/2 activation was identified.

Figure 18A:
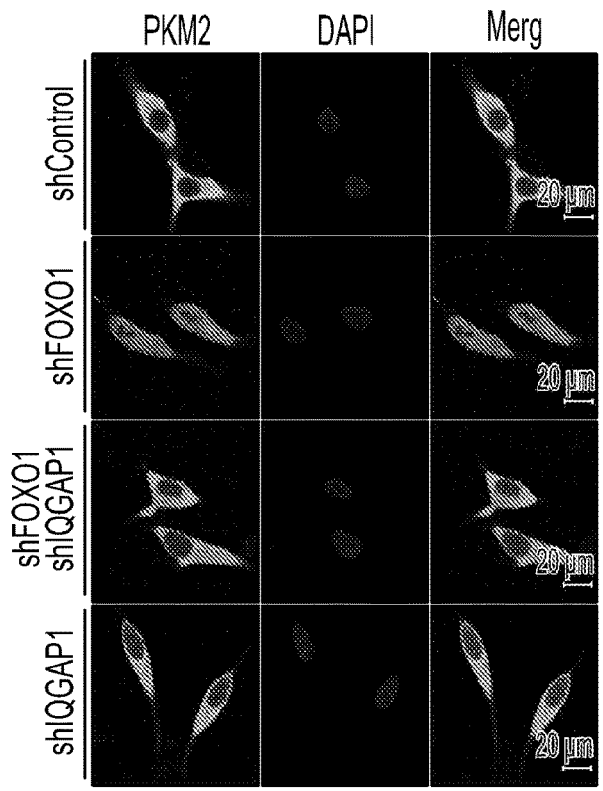
Figure 18B:
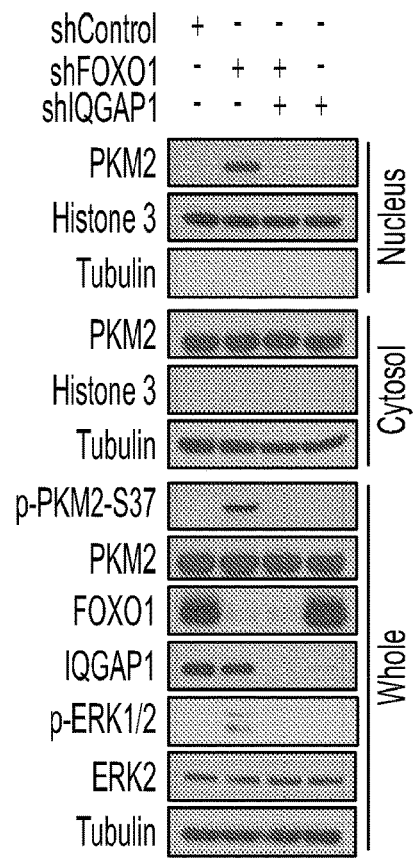
Figure 19B:
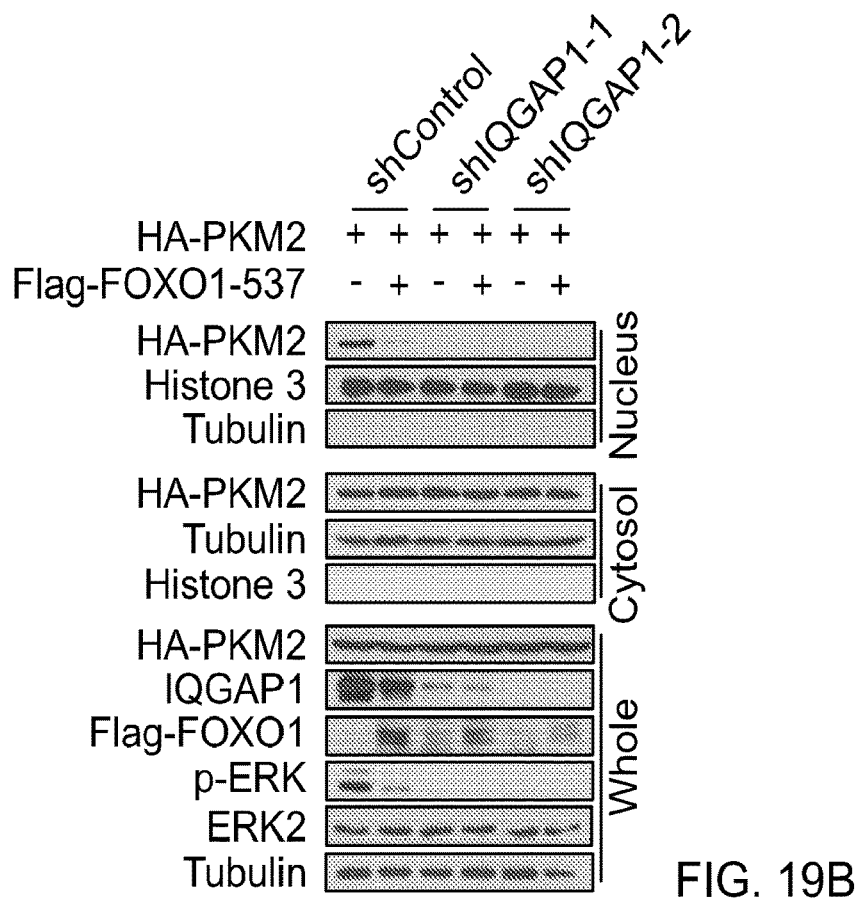

Example 3: AKT-Phosphorylated FOXO1 Inhibits PKM2 Nuclear Localization and the Warburg Effect Elevated glucose uptake and lactate production in the availability of oxygen, a phenomenon called the Warburg effect, is important for cancer cell growth (Vander Heiden et al., 2009 *Science* 324:1029-33). Expression of FOXO1 and IQGAP1 regulate PKM2 phosphorylation, nuclear localization, glucose consumption and lactate production was determined. Both immunofluorescent cytochemistry (IFC) and cellular fractionation assays demonstrated that no PKM2 protein was found in the nucleus of LNCaP cells infected control shRNAs (FIGS. 18A and B). Knockdown of endogenous FOXO1 induced nuclear localization of PKM2, but this effect was completely reversed by knockdown of endogenous IQGAP1 (FIGS. 18A and B). FOXO1 knockdown induced a parallel increase in phosphorylation of ERK1/2 and PKM2 at serine 37 in LNCaP cells (FIG. 18B). However, these effects were abrogated by IQGAP1 knockdown (FIG. 18B). In accordance with these results, overexpression of IQGAP1 increased ERK2 phosphorylation and PKM2 nuclear localization in C4-2 cells (FIG. 19B). Forced expression of transactivation-deficient FOXO1-537 abrogated IQGAP1-induced ERK1/2 phosphorylation and PKM2 nuclear localization (FIG. 19B). Moreover, PKM2 was detected in the nucleus in ERK1/2 phosphorylation-positive DU145 cells (FIG. 8A, 19B). Both knockdown of endogenous IQGAP1 and overexpression of FOXO1-537 inhibited ERK1/2 phosphorylation and PKM2 nuclear localization (FIG. 19B). These data suggest that FOXO1 is an important upstream regulator of ERK1/2-mediated phosphorylation and nuclear localization of PKM2 in prostate cancer cells.

Figure 18C:
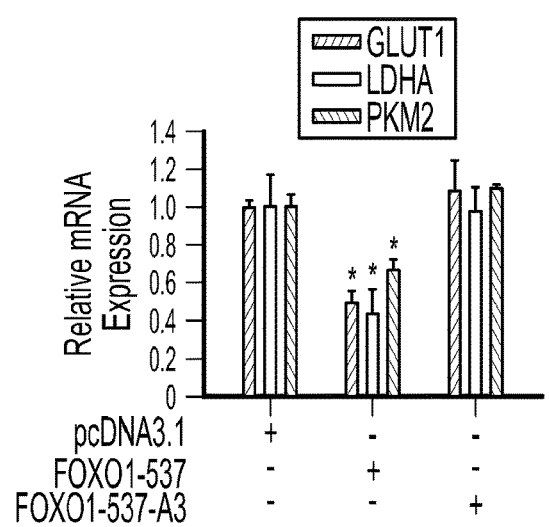
Figure 18D:
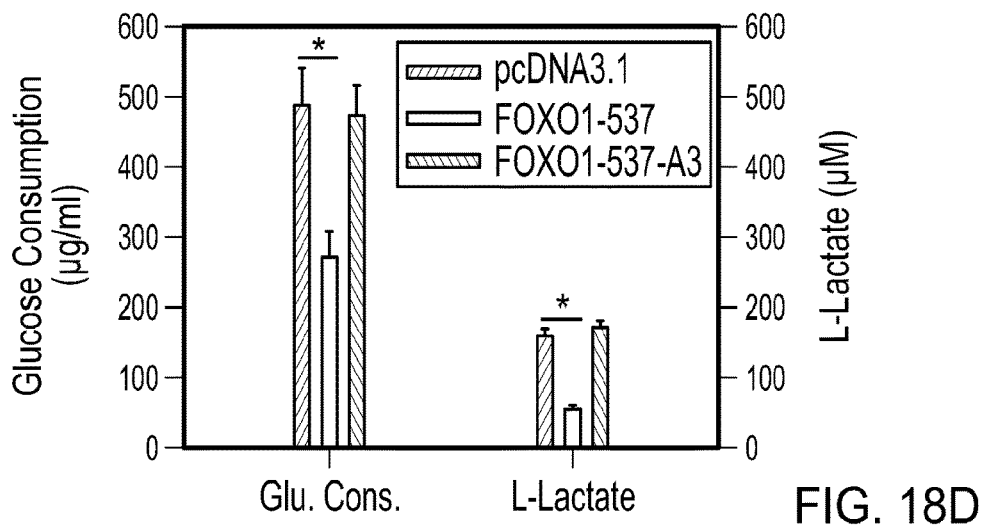
Figure 18E:
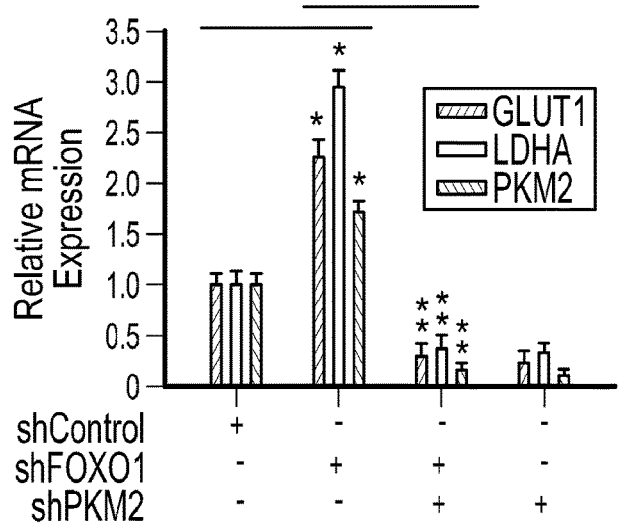
Figure 18F:
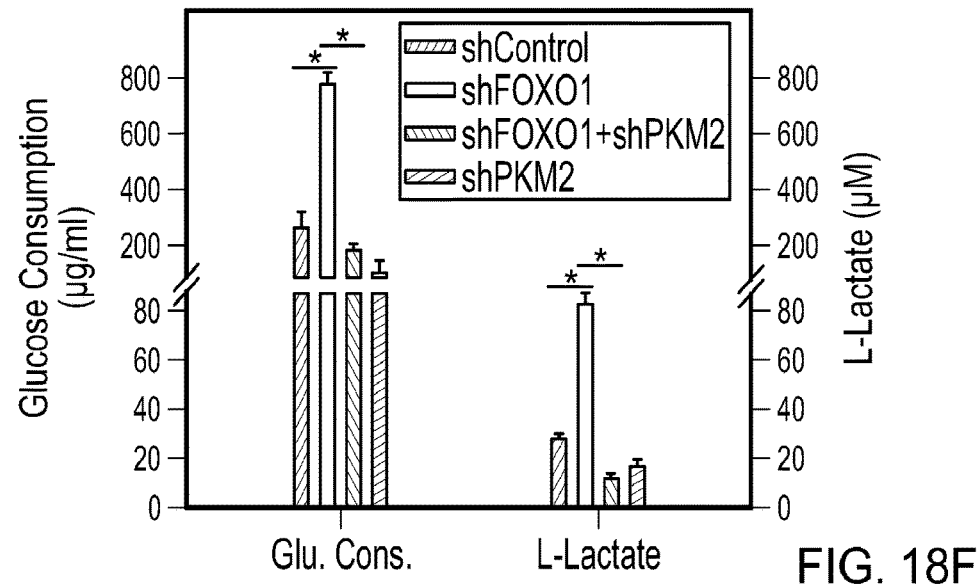
Figure 20A:
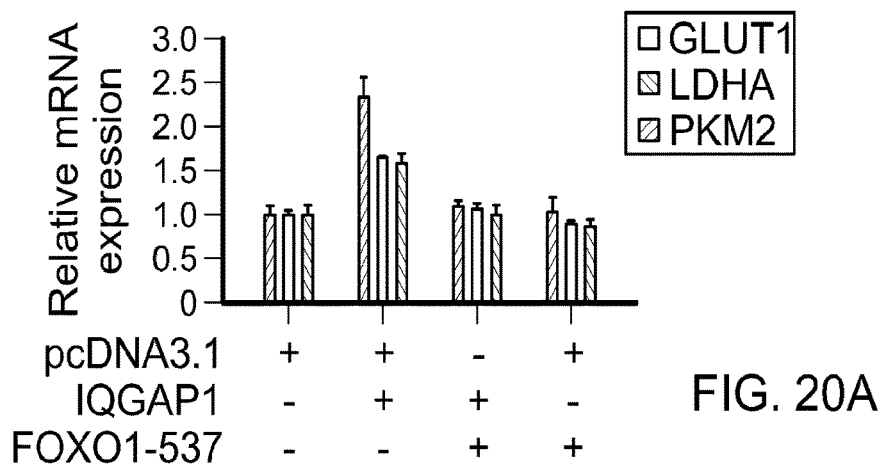
Figure 20B:
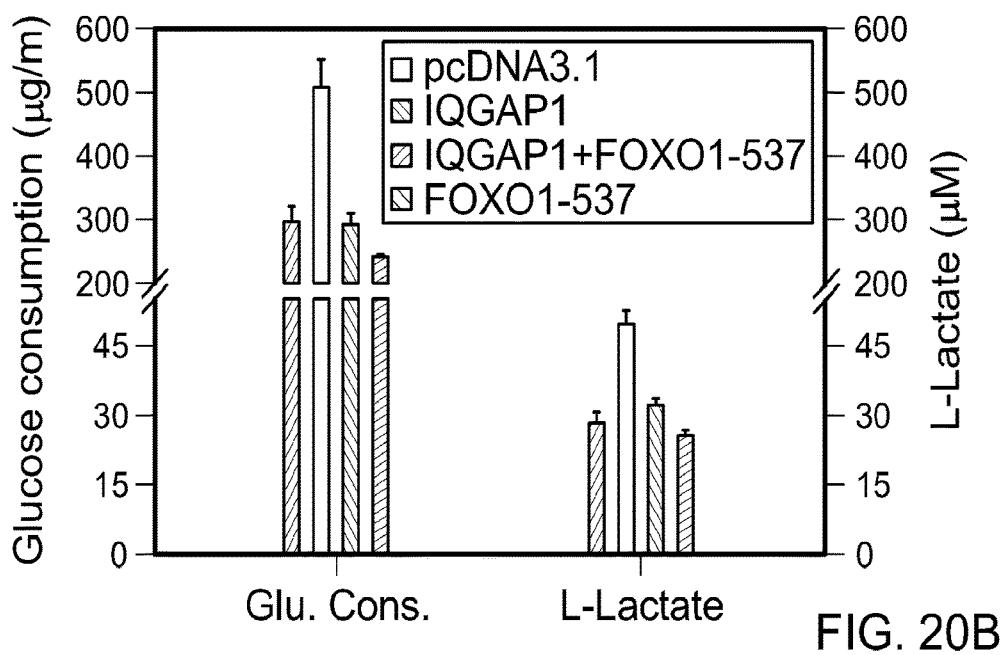
Figure 20C:
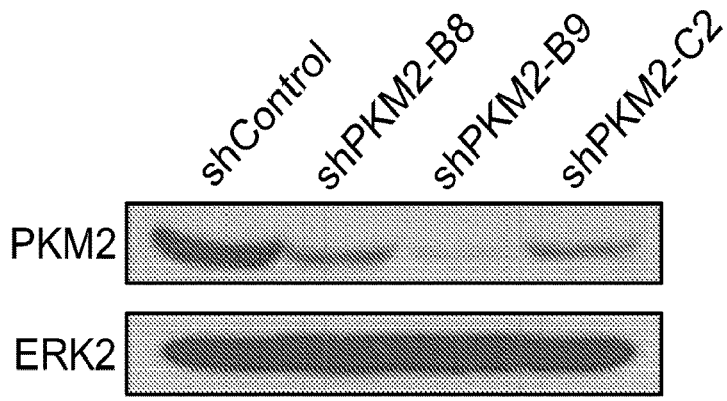
Figure 20D:
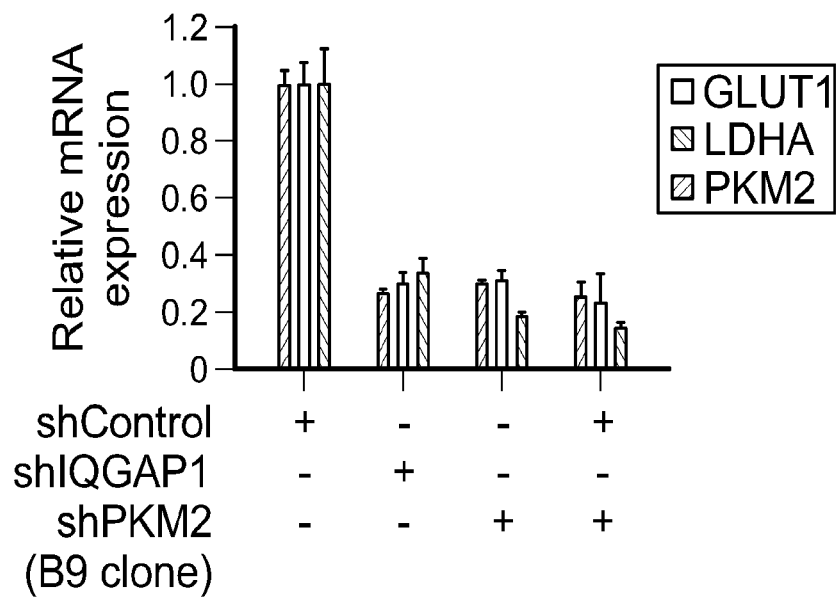
Figure 20E:
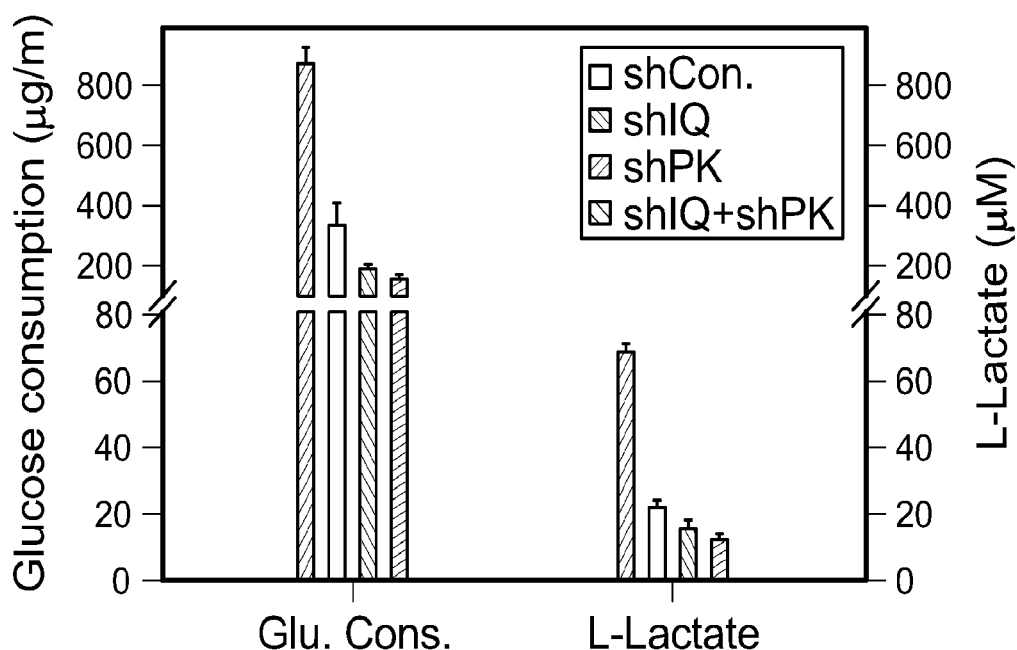

Ectopic expression of FOXO1-537 inhibited ERK1/2 phosphorylation and PKM2 nuclear localization (FIG. 19A), but also decreased GLUT1, LDHA and PKM2 expression and inhibited glucose consumption and lactate production (FIGS. 18C and D). In contrast, expression of AKT phosphorylation-resistant mutant FOXO1-537-A3, which had no effect on IQGAP1 interaction with MAPK proteins (FIG. 5D), failed to affect these gene expression, glucose consumption and lactate production (FIGS. 18C and D). Moreover, ectopic expression of IQGAP1 increased expression of these genes, glucose consumption and lactate production and these effects were reversed by co-expression of FOXO1-537 (FIGS. 20A and B). Conversely, knockdown of endogenous FOXO1 significantly upregulated expression of GLUT1, LDHA and PKM2 and increased glucose consumption and lactate production, and these effects were completely reversed by PKM2 knockdown (FIGS. 18E and F). In contrast, knockdown of endogenous IQGAP1 decreased expression of these metabolic genes, glucose consumption and lactate production, but no further reduction was observed in IQGAP1 and PKM2 co-knockdown cells (FIG. 20C-E). Together, these data suggest that AKT-phosphorylated FOXO1 inhibits the Warburg effect by negatively modulating the IQGAP1-ERK1/2-PKM2 signaling cascade in cancer cells.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A phosphorylation-mimicking FOXO1 derived peptide comprising SEQ ID NO:2.

2. The phosphorylation-mimicking FOXO1 derived peptide of claim 1, wherein said phosphorylation-mimicking FOXO1 derived peptide further comprises an epitope tag.

3. The phosphorylation-mimicking FOXO1 derived peptide of claim 2, wherein said epitope tag is a hemagglutinin (HA) tag.

4. The phosphorylation-mimicking FOXO1 derived peptide of claim 1, wherein said phosphorylation-mimicking FOXO1 derived peptide further comprises a cell-penetrating peptide.

5. The phosphorylation-mimicking FOXO1 derived peptide of claim 4, wherein said cell-penetrating peptide comprises 8 arginine residues.

6. The phosphorylation-mimicking FOXO1 derived peptide of claim 5, wherein said arginine residues are D-arginine residues.

7. The phosphorylation-mimicking FOXO1 derived peptide of claim 1, wherein said phosphorylation-mimicking FOXO1 derived peptide comprises SEQ ID NO:4.

* * * * *